US011851630B2

(12) United States Patent
Segura et al.

(10) Patent No.: US 11,851,630 B2
(45) Date of Patent: Dec. 26, 2023

(54) POLYPEPTIDES HAVING PHOSPHOLIPASE C ACTIVITY AND POLYNUCLEOTIDES ENCODING SAME

(71) Applicant: Novozymes A/S, Bagsvaerd (DK)

(72) Inventors: Dorotea Raventos Segura, Rungsted (DK); Robert Piotr Olinski, Vaerlose (DK); Kim Borch, Birkerod (DK); Allan Noergaard, Lyngby (DK); Jesper Brask, Vaerlose (DK); Rune Falkenberg Haller, Roskilde (DK); Marianne Linde Damstrup, Gentofte (DK)

(73) Assignee: Novozymes A/S, Bagsvaerd (DK)

( * ) Notice: Subject to any disclaimer, the term of this patent is extended or adjusted under 35 U.S.C. 154(b) by 98 days.

(21) Appl. No.: 17/177,349

(22) Filed: Feb. 17, 2021

(65) Prior Publication Data

US 2021/0171860 A1    Jun. 10, 2021

Related U.S. Application Data

(62) Division of application No. 16/423,748, filed on May 28, 2019, now Pat. No. 10,954,469, which is a division of application No. 15/126,098, filed as application No. PCT/EP2015/055856 on Mar. 19, 2015, now Pat. No. 10,351,795.

(30) Foreign Application Priority Data

Mar. 19, 2014   (EP) .................................... 14160698

(51) Int. Cl.
  *C12N 9/16*   (2006.01)
  *C11B 3/00*   (2006.01)
  *C12P 7/6445*   (2022.01)
  *C12N 9/20*   (2006.01)

(52) U.S. Cl.
  CPC ............... *C11B 3/003* (2013.01); *C12N 9/16* (2013.01); *C12N 9/20* (2013.01); *C12P 7/6445* (2013.01); *C12Y 301/04003* (2013.01); *C12Y 301/04011* (2013.01)

(58) Field of Classification Search
  CPC ...... C12N 9/16; C12N 9/20; C12Y 301/04011
  See application file for complete search history.

(56) References Cited

U.S. PATENT DOCUMENTS

| 10,351,795 | B2* | 7/2019 | Segura ..................... C11B 3/003 |
| 10,954,469 | B2* | 3/2021 | Segura ........... C12Y 301/04011 |
| 2008/0182322 | A1 | 7/2008 | Dayton |
| 2013/0011887 | A1 | 1/2013 | Dayton et al. |
| 2013/0309751 | A1 | 11/2013 | Tang et al. |
| 2014/0371476 | A1 | 12/2014 | Dayton |
| 2019/0284503 | A1 | 9/2019 | Segura |

FOREIGN PATENT DOCUMENTS

| CN | 101663382 |   | 3/2010 |
| CN | 102575243 | A | 7/2012 |
| CN | 103314091 | A | 9/2013 |
| WO | 2003/089620 | A2 | 10/2003 |
| WO | 2007/059927 | A1 | 5/2007 |
| WO | 2008/094847 | A1 | 8/2008 |
| WO | 2008094847 | A1 | 8/2008 |
| WO | 2011/046815 | A1 | 4/2011 |
| WO | 2012/062817 | A1 | 5/2012 |
| WO | 2015/173426 | A1 | 11/2015 |

OTHER PUBLICATIONS

Anonymous, NCBI References No. WP_006093549.1 (2013).
Anonymous, NCBI Reference No. WP_009046168.1 (2013).
Anonymous, NCBI Reference No. WP_015637460.1 (2013).
Clausen, Eur. J. Lipid Sci. Technol., vol. 103, pp. 333-340 (2001).
Dijkstra, 101st AOCS Annual Meeting & Expo, p. 23 (May 16-19, 2010).
Dijkstra, Eur. J. Lipid Sci. Technol., vol. 112, pp. 1178-1189 (2010).
Feldgarden et al., UniProt Accession No. J8N0F4 (2012).
Gavrilenko et al., GenBank Accesion No. CAA45501.1 (1993).
Kostadinova et al., Biotechnol. & Biotechnol. Eq., vol. 11, No. 3. pp. 22-27 (1997).
Paulsen et al., UniProt Accession No. Q4K3U9 (2005).
Peters et al., The Plant Cell, vol. 22, No. 8, pp. 2642-2659 (2010).
Vasconcellos et al., UniProt Accession No. U6ZX29 (2014).

* cited by examiner

Primary Examiner — Tekchand Saidha
(74) Attorney, Agent, or Firm — Eric J Fechter

(57) ABSTRACT

The present invention relates to a method of reducing the phospholipid content in an oil or fat composition and polypeptides having PI-specific phospholipase C activity as well as polypeptides having PC, PE-specific phospholipase C activity and combinations thereof capable of catalyzing this reduction. The invention also relates to polynucleotides encoding the polypeptides, nucleic acid constructs, vectors, and host cells comprising the polynucleotides as well as methods of producing and using the polypeptides.

12 Claims, 2 Drawing Sheets

Specification includes a Sequence Listing.

SEQUENCE LISTING

<160> NUMBER OF SEQ ID NOS: 38

<210> SEQ ID NO 1
<211> LENGTH: 969
<212> TYPE: DNA
<213> ORGANISM: pseudomonas sp

<400> SEQUENCE: 1

| | |
|---|---|
| atgactcatc tcattggttt cgcccctcgg ttgctggctt tttcggcgct gttgctcagc | 60 |
| cagacggcat tcagccagga aagcccggca ttcatcgatc ctgcgtcgtg aacaccccg | 120 |
| ttcaatggca ttgcccaggt ggcttgtcat aactgctacg agaagcaata cgcgaacacc | 180 |
| ttcagcagtg tgcttgacag tgtacggacc ctggagctgg acttctggga ccagcgcgat | 240 |
| gcggtgagcg gcggttcgcc ccatcactgg ttcgtgcggc acaaccccgg caccttgttc | 300 |
| caatccggca acgacaataa ctgcaccggc gatggcaccg gcaagaacga cctcgaagcc | 360 |
| tgtctgaacg acgtcaagaa ctggagtgac aagcatccgg ggcacttccc catcacgctg | 420 |
| atcctggaca gaaacagggg ctggtcgaaa gaaagttcgg ggcgcacacc aaaggatttc | 480 |
| gacgaactgg tggcgcgggt gttccagggc aagctctttta cccccagga tctggcgacg | 540 |
| cacattggca gtggcgcggg ggccttgcag ggcaacctca agggtaagtc ctggcccacc | 600 |
| gccaacgatc tgcagggcaa ggtgctgttg gtgctcaacc actcggaaaa ccagaagctc | 660 |
| tcgcagtacg ccgaggcccg cacctctaag gctaaggtgt catttcgcc agtaaccaac | 720 |
| ggccagaacg atatcagtgg caaggtcagc ggcatgtcca gccagtcatc cggctatgta | 780 |
| gccatgaaca acatgggcaa gggcgacaaa agttgggcaa gcaggccttt tgcctacagc | 840 |
| catatcggcc gcgtctgggg tgatgacgag gtgtcgttcg cccagcacat caaccagaag | 900 |
| atcaatctgt cggcgtacta caggttcgcc gcgcagagcg ctggcggcta ccgcatccgg | 960 |
| ccgttctga | 969 |

<210> SEQ ID NO 2
<211> LENGTH: 322
<212> TYPE: PRT
<213> ORGANISM: pseudomonas sp
<220> FEATURE:
<221> NAME/KEY: SIGNAL
<222> LOCATION: (1)..(25)

<400> SEQUENCE: 2

Met Thr His Leu Ile Gly Phe Ala Pro Arg Leu Leu Ala Phe Ser Ala
1               5                   10                  15

Leu Leu Leu Ser Gln Thr Ala Phe Ser Gln Glu Ser Pro Ala Phe Ile
            20                  25                  30

Asp Pro Ala Ser Trp Asn Thr Pro Phe Asn Gly Ile Ala Gln Val Ala
        35                  40                  45

Cys His Asn Cys Tyr Glu Lys Gln Tyr Ala Asn Thr Phe Ser Ser Val
    50                  55                  60

Leu Asp Ser Val Arg Thr Leu Glu Leu Asp Phe Trp Asp Gln Arg Asp
65                  70                  75                  80

Ala Val Ser Gly Gly Ser Pro His His Trp Phe Val Arg His Asn Pro
                85                  90                  95

Gly Thr Leu Phe Gln Ser Gly Asn Asp Asn Cys Thr Gly Asp Gly
            100                 105                 110

Thr Gly Lys Asn Asp Leu Glu Ala Cys Leu Asn Asp Val Lys Asn Trp
        115                 120                 125

-continued

```
Ser Asp Lys His Pro Gly His Phe Pro Ile Thr Leu Ile Leu Asp Lys
130                 135                 140

Lys Gln Gly Trp Ser Lys Glu Ser Ser Gly Arg Thr Pro Lys Asp Phe
145                 150                 155                 160

Asp Glu Leu Val Ala Arg Val Phe Gln Gly Lys Leu Phe Thr Pro Gln
                165                 170                 175

Asp Leu Ala Thr His Ile Gly Ser Gly Ala Gly Ala Leu Gln Gly Asn
            180                 185                 190

Leu Lys Gly Lys Ser Trp Pro Thr Ala Asn Asp Leu Gln Gly Lys Val
        195                 200                 205

Leu Leu Val Leu Asn His Ser Glu Asn Gln Lys Leu Ser Gln Tyr Ala
210                 215                 220

Glu Ala Arg Thr Ser Lys Ala Lys Val Phe Ile Ser Pro Val Thr Asn
225                 230                 235                 240

Gly Gln Asn Asp Ile Ser Gly Lys Val Ser Gly Met Ser Ser Gln Ser
                245                 250                 255

Ser Gly Tyr Val Ala Met Asn Asn Met Gly Lys Gly Asp Lys Ser Trp
            260                 265                 270

Ala Lys Gln Ala Phe Ala Tyr Ser His Ile Gly Arg Val Trp Gly Asp
        275                 280                 285

Asp Glu Val Ser Phe Ala Gln His Ile Asn Gln Lys Ile Asn Leu Ser
290                 295                 300

Ala Tyr Tyr Arg Phe Ala Ala Gln Ser Ala Gly Gly Tyr Arg Ile Arg
305                 310                 315                 320

Pro Phe

<210> SEQ ID NO 3
<211> LENGTH: 298
<212> TYPE: PRT
<213> ORGANISM: Artificial Sequence
<220> FEATURE:
<223> OTHER INFORMATION: variant

<400> SEQUENCE: 3

Ala Gln Glu Ser Pro Ala Phe Ile Asp Pro Ala Ser Trp Asn Thr Pro
1               5                   10                  15

Phe Asn Gly Ile Ala Gln Val Ala Cys His Asn Cys Tyr Glu Lys Gln
                20                  25                  30

Tyr Ala Asn Thr Phe Ser Ser Val Leu Asp Ser Val Arg Thr Leu Glu
            35                  40                  45

Leu Asp Phe Trp Asp Gln Arg Asp Ala Val Ser Gly Gly Ser Pro His
        50                  55                  60

His Trp Phe Val Arg His Asn Pro Gly Thr Leu Phe Gln Ser Gly Asn
65                  70                  75                  80

Asp Asn Asn Cys Thr Gly Asp Gly Thr Gly Lys Asn Asp Leu Glu Ala
                85                  90                  95

Cys Leu Asn Asp Val Lys Asn Trp Ser Asp Lys His Pro Gly His Phe
            100                 105                 110

Pro Ile Thr Leu Ile Leu Asp Lys Lys Gln Gly Trp Ser Lys Glu Ser
        115                 120                 125

Ser Gly Arg Thr Pro Lys Asp Phe Asp Glu Leu Val Ala Arg Val Phe
130                 135                 140

Gln Gly Lys Leu Phe Thr Pro Gln Asp Leu Ala Thr His Ile Gly Ser
145                 150                 155                 160

Gly Ala Gly Ala Leu Gln Gly Asn Leu Lys Gly Lys Ser Trp Pro Thr
```

Ala Asn Asp Leu Gln Gly Lys Val Leu Leu Val Leu Asn His Ser Glu
            180                 185                 190

Asn Gln Lys Leu Ser Gln Tyr Ala Glu Ala Arg Thr Ser Lys Ala Lys
        195                 200                 205

Val Phe Ile Ser Pro Val Thr Asn Gly Gln Asn Asp Ile Ser Gly Lys
    210                 215                 220

Val Ser Gly Met Ser Ser Gln Ser Ser Gly Tyr Val Ala Met Asn Asn
225                 230                 235                 240

Met Gly Lys Gly Asp Lys Ser Trp Ala Lys Gln Ala Phe Ala Tyr Ser
                245                 250                 255

His Ile Gly Arg Val Trp Gly Asp Asp Glu Val Ser Phe Ala Gln His
            260                 265                 270

Ile Asn Gln Lys Ile Asn Leu Ser Ala Tyr Tyr Arg Phe Ala Ala Gln
        275                 280                 285

Ser Ala Gly Gly Tyr Arg Ile Arg Pro Phe
    290                 295

<210> SEQ ID NO 4
<211> LENGTH: 972
<212> TYPE: DNA
<213> ORGANISM: pseudomonas chlororaphis

<400> SEQUENCE: 4
atgtcccgtc tcactcgctt tgccctccgt accgccgtga tgcccctggt gctggccagc      60
cagatggcgt ccagccagga ggctgtggga ttcatttccc cggcttcctg gtacaccgcc     120
ttcaacgcta tcgcccaggt ggcgtgccat aactgctacg aaaaacagta cgccggcacc     180
ttcaccagcg tgctcgacag cgtgcgcacc ctggagctgg acttctggga ccaacgcgat     240
gcggtcaccg gaggttcgcc ccgccactgg ttcgtgcggc acaaccccgg cagcctgttc     300
cagtccggca tgacaacaa ttgcaccggc gacggcaaag caccaacga tcttgaggcc      360
tgcctcaatg acatcaagct ctggagcgac agccatcccg ggcacttccc gattaccctg     420
atcctcgaca gaagcagggg ctggtcgaag gaaagctccg ggcgtacgcc taaagacttc     480
gatgacctgg tcagccggat tttccagggc aagctctaca ccccgggcga cctggcccag     540
cacctgggtg tcagcagcag tgccttgcag ggctcgctca agggcaagtc ctggccgacc     600
gccagccaac tgcagggcaa ggtgctgttg gtgctcaacc actcggagaa ccagaagctc     660
tcgcaatacg ccgaggcccg caccaccagc gccaaggtgt tcatttcccc ggtcaccaac     720
ggccagaacg atgtcagtgg cgaggtcagc ggcatgtcca ggacgtcgtc cggctacgtg     780
gccatgaaca acatgggcaa gggcgacaag cagtgggccg cgcaagcctt tgcctacagc     840
cacatcggtc gggtgtgggg cgatgacggc gtgtcattca cccagcacat cgccgagaag     900
gtcaatctgt cggcgtatta caaattcgcc gaggccaagg atggcaacgg ctatcgcatc     960
cggccgttct ga                                                         972

<210> SEQ ID NO 5
<211> LENGTH: 323
<212> TYPE: PRT
<213> ORGANISM: pseudomonas chlororaphis
<220> FEATURE:
<221> NAME/KEY: SIGNAL
<222> LOCATION: (1)..(25)

<400> SEQUENCE: 5

Met Ser Arg Leu Thr Arg Phe Ala Leu Arg Thr Ala Val Met Pro Leu
1               5                   10                  15

Val Leu Ala Ser Gln Met Ala Ser Ser Gln Glu Ala Val Gly Phe Ile
            20                  25                  30

Ser Pro Ala Ser Trp Tyr Thr Ala Phe Asn Ala Ile Ala Gln Val Ala
            35                  40                  45

Cys His Asn Cys Tyr Glu Lys Gln Tyr Ala Gly Thr Phe Thr Ser Val
50                  55                  60

Leu Asp Ser Val Arg Thr Leu Glu Leu Asp Phe Trp Asp Gln Arg Asp
65                  70                  75                  80

Ala Val Thr Gly Gly Ser Pro Arg His Trp Phe Val Arg His Asn Pro
                85                  90                  95

Gly Ser Leu Phe Gln Ser Gly Asn Asp Asn Asn Cys Thr Gly Asp Gly
                100                 105                 110

Lys Gly Thr Asn Asp Leu Glu Ala Cys Leu Asn Asp Ile Lys Leu Trp
            115                 120                 125

Ser Asp Ser His Pro Gly His Phe Pro Ile Thr Leu Ile Leu Asp Lys
            130                 135                 140

Lys Gln Gly Trp Ser Lys Glu Ser Ser Gly Arg Thr Pro Lys Asp Phe
145                 150                 155                 160

Asp Asp Leu Val Ser Arg Ile Phe Gln Gly Lys Leu Tyr Thr Pro Gly
                165                 170                 175

Asp Leu Ala Gln His Leu Gly Val Ser Ser Ala Leu Gln Gly Ser
                180                 185                 190

Leu Lys Gly Lys Ser Trp Pro Thr Ala Ser Gln Leu Gln Gly Lys Val
            195                 200                 205

Leu Leu Val Leu Asn His Ser Glu Asn Gln Lys Leu Ser Gln Tyr Ala
            210                 215                 220

Glu Ala Arg Thr Thr Ser Ala Lys Val Phe Ile Ser Pro Val Thr Asn
225                 230                 235                 240

Gly Gln Asn Asp Val Ser Gly Glu Val Ser Gly Met Ser Arg Thr Ser
                245                 250                 255

Ser Gly Tyr Val Ala Met Asn Asn Met Gly Lys Gly Asp Lys Gln Trp
            260                 265                 270

Ala Ala Gln Ala Phe Ala Tyr Ser His Ile Gly Arg Val Trp Gly Asp
            275                 280                 285

Asp Gly Val Ser Phe Thr Gln His Ile Ala Glu Lys Val Asn Leu Ser
            290                 295                 300

Ala Tyr Tyr Lys Phe Ala Glu Ala Lys Asp Gly Asn Gly Tyr Arg Ile
305                 310                 315                 320

Arg Pro Phe

<210> SEQ ID NO 6
<211> LENGTH: 299
<212> TYPE: PRT
<213> ORGANISM: Artificial Sequence
<220> FEATURE:
<223> OTHER INFORMATION: variant

<400> SEQUENCE: 6

Ala Gln Glu Ala Val Gly Phe Ile Ser Pro Ala Ser Trp Tyr Thr Ala
1               5                   10                  15

Phe Asn Ala Ile Ala Gln Val Ala Cys His Asn Cys Tyr Glu Lys Gln
            20                  25                  30

Tyr Ala Gly Thr Phe Thr Ser Val Leu Asp Ser Val Arg Thr Leu Glu

```
                35                  40                  45
Leu Asp Phe Trp Asp Gln Arg Asp Ala Val Thr Gly Gly Ser Pro Arg
 50                  55                  60

His Trp Phe Val Arg His Asn Pro Gly Ser Leu Phe Gln Ser Gly Asn
 65                  70                  75                  80

Asp Asn Asn Cys Thr Gly Asp Gly Lys Gly Thr Asn Asp Leu Glu Ala
                 85                  90                  95

Cys Leu Asn Asp Ile Lys Leu Trp Ser Asp Ser His Pro Gly His Phe
                100                 105                 110

Pro Ile Thr Leu Ile Leu Asp Lys Lys Gln Gly Trp Ser Lys Glu Ser
            115                 120                 125

Ser Gly Arg Thr Pro Lys Asp Phe Asp Asp Leu Val Ser Arg Ile Phe
130                 135                 140

Gln Gly Lys Leu Tyr Thr Pro Gly Asp Leu Ala Gln His Leu Gly Val
145                 150                 155                 160

Ser Ser Ser Ala Leu Gln Gly Ser Leu Lys Gly Lys Ser Trp Pro Thr
                165                 170                 175

Ala Ser Gln Leu Gln Gly Lys Val Leu Leu Val Leu Asn His Ser Glu
            180                 185                 190

Asn Gln Lys Leu Ser Gln Tyr Ala Glu Ala Arg Thr Ser Ala Lys
        195                 200                 205

Val Phe Ile Ser Pro Val Thr Asn Gly Gln Asn Asp Val Ser Gly Glu
210                 215                 220

Val Ser Gly Met Ser Arg Thr Ser Ser Gly Tyr Val Ala Met Asn Asn
225                 230                 235                 240

Met Gly Lys Gly Asp Lys Gln Trp Ala Ala Gln Ala Phe Ala Tyr Ser
                245                 250                 255

His Ile Gly Arg Val Trp Gly Asp Gly Val Ser Phe Thr Gln His
            260                 265                 270

Ile Ala Glu Lys Val Asn Leu Ser Ala Tyr Tyr Lys Phe Ala Glu Ala
        275                 280                 285

Lys Asp Gly Asn Gly Tyr Arg Ile Arg Pro Phe
290                 295

<210> SEQ ID NO 7
<211> LENGTH: 972
<212> TYPE: DNA
<213> ORGANISM: pseudomonas sp

<400> SEQUENCE: 7
atgtcccgtc tcactggttt tgccctccgt accgccgtgc tgccctggc actggccagc      60 cagatggcgt ccagccagga ggccgtggga ttcatttccc cggcgtcctg gtacaccgcc    120
ttcaacgcta tcgcccaggt ggcatgccat aactgctacg aaaaacagta cgccggcacc    180
ttcaccagcg tgctcgatag cgtgcgcacc ctggagctgg acttctggga ccaacgcgat    240
gcggtcaccg gaggttcgcc ccgccactgg ttcgtgcggc acaaccccgg cagcctgttc    300
cagtccggca atgacaacaa ttgcaccggc gacggcaacg gcaccaacga tctcgaagcc    360
tgcctcaacg acatcaagct ctggagcgac agccatcccg gcacttccc gattaccctg    420 atcctcgaca agaagcaggg ctggtcgaag gaaagctccg gcgtacgcc gaaagacttc    480 gatgacctgg tcagccggat tttccagggc aagctctaca ccccgggcga cctggcccag    540
catctgggtg tcagcagcag tgccttgcag ggctcgctca gggcaagtc ctggccgacc    600 gccagccaac tgcagggcaa ggtgctgctg gtgctcaacc actcggagaa ccagaagctc    660
```

-continued

```
tcgcaatacg ccgaggcccg caccaccagc gccaaggtgt tcatttcccc ggtcaccaac      720
ggccagaacg atgtcagtgg cgaggtcagc ggcatgtcga ggacgtcgtc cggctacgtg      780
gccatgaaca acatgggcaa gggcgacaag cagtgggccg cgcaagcctt tgtctacagc      840
cacatcggtc gggtgtgggg tgatgacggc gtgtcattca cccagcacat cgccgagaag      900
gtcaatctgt cggcgtatta caaattcgcc gaggccaagg atggcaacgg ctatcgcatc      960
cgaccgttct ga                                                          972
```

<210> SEQ ID NO 8
<211> LENGTH: 323
<212> TYPE: PRT
<213> ORGANISM: pseudomonas sp
<220> FEATURE:
<221> NAME/KEY: SIGNAL
<222> LOCATION: (1)..(25)

<400> SEQUENCE: 8

```
Met Ser Arg Leu Thr Gly Phe Ala Leu Arg Thr Ala Val Leu Pro Leu
1               5                   10                  15

Ala Leu Ala Ser Gln Met Ala Ser Ser Gln Glu Ala Val Gly Phe Ile
            20                  25                  30

Ser Pro Ala Ser Trp Tyr Thr Ala Phe Asn Ala Ile Ala Gln Val Ala
        35                  40                  45

Cys His Asn Cys Tyr Glu Lys Gln Tyr Ala Gly Thr Phe Thr Ser Val
    50                  55                  60

Leu Asp Ser Val Arg Thr Leu Glu Leu Asp Phe Trp Asp Gln Arg Asp
65                  70                  75                  80

Ala Val Thr Gly Gly Ser Pro Arg His Trp Phe Val Arg His Asn Pro
                85                  90                  95

Gly Ser Leu Phe Gln Ser Gly Asn Asp Asn Cys Thr Gly Asp Gly
            100                 105                 110

Asn Gly Thr Asn Asp Leu Glu Ala Cys Leu Asn Asp Ile Lys Leu Trp
        115                 120                 125

Ser Asp Ser His Pro Gly His Phe Pro Ile Thr Leu Ile Leu Asp Lys
    130                 135                 140

Lys Gln Gly Trp Ser Lys Glu Ser Ser Gly Arg Thr Pro Lys Asp Phe
145                 150                 155                 160

Asp Asp Leu Val Ser Arg Ile Phe Gln Gly Lys Leu Tyr Thr Pro Gly
                165                 170                 175

Asp Leu Ala Gln His Leu Gly Val Ser Ser Ala Leu Gln Gly Ser
            180                 185                 190

Leu Lys Gly Lys Ser Trp Pro Thr Ala Ser Gln Leu Gln Gly Lys Val
        195                 200                 205

Leu Leu Val Leu Asn His Ser Glu Asn Gln Lys Leu Ser Gln Tyr Ala
    210                 215                 220

Glu Ala Arg Thr Thr Ser Ala Lys Val Phe Ile Ser Pro Val Thr Asn
225                 230                 235                 240

Gly Gln Asn Asp Val Ser Gly Glu Val Ser Gly Met Ser Arg Thr Ser
                245                 250                 255

Ser Gly Tyr Val Ala Met Asn Asn Met Gly Lys Gly Asp Lys Gln Trp
            260                 265                 270

Ala Ala Gln Ala Phe Val Tyr Ser His Ile Gly Arg Val Trp Gly Asp
        275                 280                 285

Asp Gly Val Ser Phe Thr Gln His Ile Ala Glu Lys Val Asn Leu Ser
```

```
                290                 295                 300
Ala Tyr Tyr Lys Phe Ala Glu Ala Lys Asp Gly Asn Gly Tyr Arg Ile
305                 310                 315                 320

Arg Pro Phe

<210> SEQ ID NO 9
<211> LENGTH: 299
<212> TYPE: PRT
<213> ORGANISM: Artificial Sequence
<220> FEATURE:
<223> OTHER INFORMATION: Variant

<400> SEQUENCE: 9

Ala Gln Glu Ala Val Gly Phe Ile Ser Pro Ala Ser Trp Tyr Thr Ala
1               5                   10                  15

Phe Asn Ala Ile Ala Gln Val Ala Cys His Asn Cys Tyr Glu Lys Gln
            20                  25                  30

Tyr Ala Gly Thr Phe Thr Ser Val Leu Asp Ser Val Arg Thr Leu Glu
        35                  40                  45

Leu Asp Phe Trp Asp Gln Arg Asp Ala Val Thr Gly Gly Ser Pro Arg
    50                  55                  60

His Trp Phe Val Arg His Asn Pro Gly Ser Leu Phe Gln Ser Gly Asn
65                  70                  75                  80

Asp Asn Asn Cys Thr Gly Asp Gly Asn Gly Thr Asn Asp Leu Glu Ala
                85                  90                  95

Cys Leu Asn Asp Ile Lys Leu Trp Ser Asp Ser His Pro Gly His Phe
            100                 105                 110

Pro Ile Thr Leu Ile Leu Asp Lys Lys Gln Gly Trp Ser Lys Glu Ser
        115                 120                 125

Ser Gly Arg Thr Pro Lys Asp Phe Asp Asp Leu Val Ser Arg Ile Phe
    130                 135                 140

Gln Gly Lys Leu Tyr Thr Pro Gly Asp Leu Ala Gln His Leu Gly Val
145                 150                 155                 160

Ser Ser Ser Ala Leu Gln Gly Ser Leu Lys Gly Lys Ser Trp Pro Thr
                165                 170                 175

Ala Ser Gln Leu Gln Gly Lys Val Leu Leu Val Leu Asn His Ser Glu
            180                 185                 190

Asn Gln Lys Leu Ser Gln Tyr Ala Glu Ala Arg Thr Thr Ser Ala Lys
        195                 200                 205

Val Phe Ile Ser Pro Val Thr Asn Gly Gln Asn Asp Val Ser Gly Glu
    210                 215                 220

Val Ser Gly Met Ser Arg Thr Ser Ser Gly Tyr Val Ala Met Asn Asn
225                 230                 235                 240

Met Gly Lys Gly Asp Lys Gln Trp Ala Ala Gln Ala Phe Val Tyr Ser
                245                 250                 255

His Ile Gly Arg Val Trp Gly Asp Asp Gly Val Ser Phe Thr Gln His
            260                 265                 270

Ile Ala Glu Lys Val Asn Leu Ser Ala Tyr Tyr Lys Phe Ala Glu Ala
        275                 280                 285

Lys Asp Gly Asn Gly Tyr Arg Ile Arg Pro Phe
    290                 295

<210> SEQ ID NO 10
<211> LENGTH: 972
<212> TYPE: DNA
<213> ORGANISM: Pseudomonas chlororaphis
```

<400> SEQUENCE: 10

```
atgtcccgtc tcactcgttt tgccctccgt acagccgtac tgcccctggc gctggccagc      60
cagatggcgt ccagccagga ggccgcggga ttcatttctc cggcttcctg gtacagcgcc     120
ttcaacgcta tcgcccaggt ggcgtgccat aactgctacg aaaaacagta cgccagcacc     180
ttcaccagtg tgctcgacag cgtgcgtacc ctggagctgg atttctggga ccagcgcgat     240
gcggtcaccg tggttcggc cggtcactgg ttcgtgcggc acaacccgg cacgctgttc       300
cagtccggca atgacaacaa ctgcaccggc gacggcaaag caccaacga tctcgaggcc     360
tgcctcaacg catcaggct ctggagcgac agccatcccg gcacttccc gattaccctg      420
atcctcgaca agaagcaggg ctggtcgaag aaagctccg ggcgtacgcc gaaagacttc     480
gatgatctgg tcagccggat tttccagggc aagctctata ccccgggcga cctgcccag     540
cacctgggtg tcagcagcgg tgccttgcag ggctcgctcg agggcaagtc ctggccgacc     600
gctagccaac tgcagggcaa ggtgctgctg gtgctcaacc actcggagaa ccagaagctc     660
tcgcaatacg ccgaagcccg gaccaccagc gccaaggtgt catttcacc ggtcaccaac     720
ggccagaacg atgtcagtgg cgaggtcagc ggcatgtcca ggacgtcgtc cggttacgtg     780
gccatgaaca acatgggcaa gggcgacaag cagtgggccg cacaagcctt tgcctacagc     840
cacatcggtc gggtgtgggg tgatgacggc gtgtcattca cccagcacat cgccgagaag     900
gtcaatctgt cggcgtatta caagttcgcc gaagccaagg atggcaacgg ctatcgcatc     960
cggccgttct aa                                                         972
```

<210> SEQ ID NO 11
<211> LENGTH: 323
<212> TYPE: PRT
<213> ORGANISM: Pseudomonas chlororaphis
<220> FEATURE:
<221> NAME/KEY: SIGNAL
<222> LOCATION: (1)..(25)

<400> SEQUENCE: 11

```
Met Ser Arg Leu Thr Arg Phe Ala Leu Arg Thr Ala Val Leu Pro Leu
1               5                   10                  15

Ala Leu Ala Ser Gln Met Ala Ser Ser Gln Glu Ala Ala Gly Phe Ile
            20                  25                  30

Ser Pro Ala Ser Trp Tyr Ser Ala Phe Asn Ala Ile Ala Gln Val Ala
        35                  40                  45

Cys His Asn Cys Tyr Glu Lys Gln Tyr Ala Ser Thr Phe Thr Ser Val
    50                  55                  60

Leu Asp Ser Val Arg Thr Leu Glu Leu Asp Phe Trp Asp Gln Arg Asp
65                  70                  75                  80

Ala Val Thr Gly Gly Ser Ala Gly His Trp Phe Val Arg His Asn Pro
                85                  90                  95

Gly Thr Leu Phe Gln Ser Gly Asn Asp Asn Cys Thr Gly Asp Gly
            100                 105                 110

Lys Gly Thr Asn Asp Leu Glu Ala Cys Leu Asn Asp Ile Arg Leu Trp
        115                 120                 125

Ser Asp Ser His Pro Gly His Phe Pro Ile Thr Leu Ile Leu Asp Lys
    130                 135                 140

Lys Gln Gly Trp Ser Lys Glu Ser Ser Gly Arg Thr Pro Lys Asp Phe
145                 150                 155                 160

Asp Asp Leu Val Ser Arg Ile Phe Gln Gly Lys Leu Tyr Thr Pro Gly
```

```
                    165                 170                 175

Asp Leu Ala Gln His Leu Gly Val Ser Ser Gly Ala Leu Gln Gly Ser
            180                 185                 190

Leu Glu Gly Lys Ser Trp Pro Thr Ala Ser Gln Leu Gln Gly Lys Val
        195                 200                 205

Leu Leu Val Leu Asn His Ser Glu Asn Gln Lys Leu Ser Gln Tyr Ala
    210                 215                 220

Glu Ala Arg Thr Thr Ser Ala Lys Val Phe Ile Ser Pro Val Thr Asn
225                 230                 235                 240

Gly Gln Asn Asp Val Ser Gly Glu Val Ser Gly Met Ser Arg Thr Ser
                245                 250                 255

Ser Gly Tyr Val Ala Met Asn Asn Met Gly Lys Gly Asp Lys Gln Trp
            260                 265                 270

Ala Ala Gln Ala Phe Ala Tyr Ser His Ile Gly Arg Val Trp Gly Asp
        275                 280                 285

Asp Gly Val Ser Phe Thr Gln His Ile Ala Glu Lys Val Asn Leu Ser
    290                 295                 300

Ala Tyr Tyr Lys Phe Ala Glu Ala Lys Asp Gly Asn Gly Tyr Arg Ile
305                 310                 315                 320

Arg Pro Phe

<210> SEQ ID NO 12
<211> LENGTH: 296
<212> TYPE: PRT
<213> ORGANISM: Artificial Sequence
<220> FEATURE:
<223> OTHER INFORMATION: variant

<400> SEQUENCE: 12

Ala Ala Gly Phe Ile Ser Pro Ala Ser Trp Tyr Ser Ala Phe Asn Ala
1               5                   10                  15

Ile Ala Gln Val Ala Cys His Asn Cys Tyr Glu Lys Gln Tyr Ala Ser
            20                  25                  30

Thr Phe Thr Ser Val Leu Asp Ser Val Arg Thr Leu Glu Leu Asp Phe
        35                  40                  45

Trp Asp Gln Arg Asp Ala Val Thr Gly Gly Ser Ala Gly His Trp Phe
    50                  55                  60

Val Arg His Asn Pro Gly Thr Leu Phe Gln Ser Gly Asn Asp Asn Asn
65                  70                  75                  80

Cys Thr Gly Asp Gly Lys Gly Thr Asn Asp Leu Glu Ala Cys Leu Asn
                85                  90                  95

Asp Ile Arg Leu Trp Ser Asp Ser His Pro Gly His Phe Pro Ile Thr
            100                 105                 110

Leu Ile Leu Asp Lys Lys Gln Gly Trp Ser Lys Glu Ser Ser Gly Arg
        115                 120                 125

Thr Pro Lys Asp Phe Asp Asp Leu Val Ser Arg Ile Phe Gln Gly Lys
    130                 135                 140

Leu Tyr Thr Pro Gly Asp Leu Ala Gln His Leu Gly Val Ser Ser Gly
145                 150                 155                 160

Ala Leu Gln Gly Ser Leu Glu Gly Lys Ser Trp Pro Thr Ala Ser Gln
                165                 170                 175

Leu Gln Gly Lys Val Leu Leu Val Leu Asn His Ser Glu Asn Gln Lys
            180                 185                 190

Leu Ser Gln Tyr Ala Glu Ala Arg Thr Thr Ser Ala Lys Val Phe Ile
        195                 200                 205
```

```
Ser Pro Val Thr Asn Gly Gln Asn Asp Val Ser Gly Glu Val Ser Gly
    210                 215                 220

Met Ser Arg Thr Ser Ser Gly Tyr Val Ala Met Asn Asn Met Gly Lys
225                 230                 235                 240

Gly Asp Lys Gln Trp Ala Ala Gln Ala Phe Ala Tyr Ser His Ile Gly
                245                 250                 255

Arg Val Trp Gly Asp Asp Gly Val Ser Phe Thr Gln His Ile Ala Glu
            260                 265                 270

Lys Val Asn Leu Ser Ala Tyr Tyr Lys Phe Ala Glu Ala Lys Asp Gly
        275                 280                 285

Asn Gly Tyr Arg Ile Arg Pro Phe
    290                 295

<210> SEQ ID NO 13
<211> LENGTH: 969
<212> TYPE: DNA
<213> ORGANISM: Pseudomonas protegens

<400> SEQUENCE: 13
atgactcatc tttcccgttt cgtcccccgc gccctggcgc tgtcggcact cttgctcagc      60
ccggcggcgt tcagccagga agcccggcg ttcatcgccc cggctacctg gaataccccg     120
```

```
                35                  40                  45
Cys His Asn Cys Tyr Glu Lys Gln Tyr Ala Ser Thr Phe Ser Ser Val
 50                  55                  60

Leu Asp Ser Val Arg Thr Leu Glu Leu Asp Phe Trp Asp Gln Arg Asp
 65                  70                  75                  80

Ala Val Thr Gly Gly Ser Pro Arg His Trp Phe Val Arg His Asn Pro
                 85                  90                  95

Gly Thr Leu Phe Gln Ser Gly Asn Asp Asn Cys Thr Gly Asp Gly
                100                 105                 110

Thr Gly Lys Asn Asp Leu Glu Ala Cys Leu Asn Asp Val Lys Asn Trp
                115                 120                 125

Ser Glu Asn His Pro Gly His Phe Pro Ile Thr Val Ile Leu Asp Lys
130                 135                 140

Lys Gln Gly Trp Ser Lys Glu Ser Ser Gly Arg Thr Pro Lys Asp Phe
145                 150                 155                 160

Asp Glu Leu Val Thr Arg Val Phe Gln Gly Lys Leu Tyr Thr Pro Gln
                165                 170                 175

Asp Leu Ala Thr His Ile Gly Ser Ser Ala Gly Ala Leu Gln Gly Asn
                180                 185                 190

Leu Lys Gly Lys Ser Trp Pro Thr Ala Ser Gln Leu Gln Gly Lys Val
                195                 200                 205

Leu Leu Val Leu Asn His Ser Glu Asn Gln Lys Leu Ser Gln Tyr Ala
                210                 215                 220

Glu Ala Arg Thr Ser Ser Ala Lys Val Phe Ile Ser Pro Val Thr Asn
225                 230                 235                 240

Gly Gln Asn Asp Val Ser Gly Lys Val Ser Gly Met Ser Gly Gln Ser
                245                 250                 255

Ser Gly Tyr Val Ala Met Asn Asn Met Ser Lys Gly Asp Lys Lys Trp
                260                 265                 270

Ala Ala Gln Ala Phe Ala Tyr Ser His Val Gly Arg Val Trp Gly Asp
                275                 280                 285

Asp Gly Val Ser Phe Ala Gln His Ile Ser Glu Lys Val Asn Leu Ser
                290                 295                 300

Ala Tyr Tyr Lys Phe Ala Glu Gln Asn Ser Gly Gly Tyr Arg Ile Arg
305                 310                 315                 320

Pro Phe

<210> SEQ ID NO 15
<211> LENGTH: 298
<212> TYPE: PRT
<213> ORGANISM: Artificial Sequence
<220> FEATURE:
<223> OTHER INFORMATION: variant

<400> SEQUENCE: 15

Ala Gln Glu Ser Pro Ala Phe Ile Ala Pro Ala Thr Trp Asn Thr Pro
 1               5                  10                  15

Phe Asn Gly Ile Ala Gln Val Ala Cys His Asn Cys Tyr Glu Lys Gln
                20                  25                  30

Tyr Ala Ser Thr Phe Ser Ser Val Leu Asp Ser Val Arg Thr Leu Glu
                35                  40                  45

Leu Asp Phe Trp Asp Gln Arg Asp Ala Val Thr Gly Gly Ser Pro Arg
 50                  55                  60

His Trp Phe Val Arg His Asn Pro Gly Thr Leu Phe Gln Ser Gly Asn
 65                  70                  75                  80
```

```
Asp Asn Asn Cys Thr Gly Asp Gly Thr Gly Lys Asn Asp Leu Glu Ala
                 85                  90                  95
Cys Leu Asn Asp Val Lys Asn Trp Ser Glu Asn His Pro Gly His Phe
            100                 105                 110
Pro Ile Thr Val Ile Leu Asp Lys Lys Gln Gly Trp Ser Lys Glu Ser
        115                 120                 125
Ser Gly Arg Thr Pro Lys Asp Phe Asp Glu Leu Val Thr Arg Val Phe
    130                 135                 140
Gln Gly Lys Leu Tyr Thr Pro Gln Asp Leu Ala Thr His Ile Gly Ser
145                 150                 155                 160
Ser Ala Gly Ala Leu Gln Gly Asn Leu Lys Gly Lys Ser Trp Pro Thr
                165                 170                 175
Ala Ser Gln Leu Gln Gly Lys Val Leu Leu Val Leu Asn His Ser Glu
            180                 185                 190
Asn Gln Lys Leu Ser Gln Tyr Ala Glu Ala Arg Thr Ser Ser Ala Lys
        195                 200                 205
Val Phe Ile Ser Pro Val Thr Asn Gly Gln Asn Asp Val Ser Gly Lys
    210                 215                 220
Val Ser Gly Met Ser Gly Gln Ser Ser Gly Tyr Val Ala Met Asn Asn
225                 230                 235                 240
Met Ser Lys Gly Asp Lys Lys Trp Ala Ala Gln Ala Phe Ala Tyr Ser
                245                 250                 255
His Val Gly Arg Val Trp Gly Asp Asp Gly Val Ser Phe Ala Gln His
            260                 265                 270
Ile Ser Glu Lys Val Asn Leu Ser Ala Tyr Tyr Lys Phe Ala Glu Gln
        275                 280                 285
Asn Ser Gly Gly Tyr Arg Ile Arg Pro Phe
    290                 295

<210> SEQ ID NO 16
<211> LENGTH: 969
<212> TYPE: DNA
<213> ORGANISM: Pseudomonas protegens

<400> SEQUENCE: 16
atgactcatc tttcccgttt cgtccccgc gccctggcgc tgtcggcact cctgctcagc    60
ccggcggcgt tcagccagga aagcccggcg ttcatcgccc ggctacctg gaataccccg   120
ttcaacggca tcgcccaggt ggcctgtcac aactgctacg agaagcagta cgcaagcacc   180
tttagcagcg tgctcgacag tgtgcgcacc ctggaactgg acttctggga ccagcgcgat   240
gcggtgaccg gcggctcgcc ccggcactgg ttcgtgcggc acaaccccgg caccctgttc   300
cagtccggca cgacaacaa ttgcacgggc gatggcaccg gcaagaacga tctcgaagcc   360
tgcctcaacg acgtgaagaa ctggagcgac aaccaccccg gcactttcc cattacggtg   420
atcctcgaca gaagcaggg ctggtcgaag gaaagctcgg gcgcacgcc caaggatttc   480
gatgagctgg tgacccgggt cttccagggc aagctctata ccccccagga cctggccacg   540
cacatcggca gcagcgcggg cgccttgcag gcaacctca agggcaagtc ctggcccacc   600
gccagccagc ttcagggcaa ggtcctgctg gtgctcaacc actcggaaaa ccagaagctc   660
tcgcagtacg ccgaggcccg gacttccagc gccaaggtgt tcatctcgcc ggtgaccaat   720
ggccagaacg atgtcagtgg caaggtcagt ggcatgtccg gccagtcgtc cggctacgtg   780
gccatgaaca acatgtccaa gggcgacaag aagtgggcgg cccaggcctt tgcctacagc   840
```

```
catgtgggcc gggtctgggg cgatgacggg gtgtcgttcg cccagcacat cagcgagaag    900
gtcaacctct cggcctacta caagttcgcc gagcagaacg ccggcggcta tcgcatccgg    960
ccgttctga                                                             969
```

<210> SEQ ID NO 17
<211> LENGTH: 322
<212> TYPE: PRT
<213> ORGANISM: Pseudomonas protegens
<220> FEATURE:
<221> NAME/KEY: SIGNAL
<222> LOCATION: (1)..(25)

<400> SEQUENCE: 17

```
Met Thr His Leu Ser Arg Phe Val Pro Arg Ala Leu Ala Leu Ser Ala
1               5                   10                  15

Leu Leu Leu Ser Pro Ala Ala Phe Ser Gln Glu Ser Pro Ala Phe Ile
            20                  25                  30

Ala Pro Ala Thr Trp Asn Thr Pro Phe Asn Gly Ile Ala Gln Val Ala
        35                  40                  45

Cys His Asn Cys Tyr Glu Lys Gln Tyr Ala Ser Thr Phe Ser Ser Val
    50                  55                  60

Leu Asp Ser Val Arg Thr Leu Glu Leu Asp Phe Trp Asp Gln Arg Asp
65                  70                  75                  80

Ala Val Thr Gly Gly Ser Pro Arg His Trp Phe Val Arg His Asn Pro
                85                  90                  95

Gly Thr Leu Phe Gln Ser Gly Asn Asp Asn Asn Cys Thr Gly Asp Gly
            100                 105                 110

Thr Gly Lys Asn Asp Leu Glu Ala Cys Leu Asn Asp Val Lys Asn Trp
        115                 120                 125

Ser Asp Asn His Pro Gly His Phe Pro Ile Thr Val Ile Leu Asp Lys
    130                 135                 140

Lys Gln Gly Trp Ser Lys Glu Ser Ser Gly Arg Thr Pro Lys Asp Phe
145                 150                 155                 160

Asp Glu Leu Val Thr Arg Val Phe Gln Gly Lys Leu Tyr Thr Pro Gln
                165                 170                 175

Asp Leu Ala Thr His Ile Gly Ser Ser Ala Gly Ala Leu Gln Gly Asn
            180                 185                 190

Leu Lys Gly Lys Ser Trp Pro Thr Ala Ser Gln Leu Gln Gly Lys Val
        195                 200                 205

Leu Leu Val Leu Asn His Ser Glu Asn Gln Lys Leu Ser Gln Tyr Ala
    210                 215                 220

Glu Ala Arg Thr Ser Ser Ala Lys Val Phe Ile Ser Pro Val Thr Asn
225                 230                 235                 240

Gly Gln Asn Asp Val Ser Gly Lys Val Ser Gly Met Ser Gly Gln Ser
                245                 250                 255

Ser Gly Tyr Val Ala Met Asn Asn Met Ser Lys Gly Asp Lys Lys Trp
            260                 265                 270

Ala Ala Gln Ala Phe Ala Tyr Ser His Val Gly Arg Val Trp Gly Asp
        275                 280                 285

Asp Gly Val Ser Phe Ala Gln His Ile Ser Glu Lys Val Asn Leu Ser
    290                 295                 300

Ala Tyr Tyr Lys Phe Ala Glu Gln Asn Ala Gly Gly Tyr Arg Ile Arg
305                 310                 315                 320

Pro Phe
```

<210> SEQ ID NO 18
<211> LENGTH: 837
<212> TYPE: DNA
<213> ORGANISM: Bacillus sp

<400> SEQUENCE: 18

```
atgaaacatc atcgttttcg aacgaattta ttatcggctc tttcagtaag ttcaattgtc    60
atcacctcaa tcatcggctc cactcaaacc acgtacgctt ggtcggccga tgctccgcat   120
gatcccaatc agagcacaca cctgtttatc gtgaacggtg ctgtcaatct ggttgccaac   180
aatacggacc cgcagatcaa caagcccacc gcgctgttgc aacagtggcg ttctcaatgg   240
gagcaagggt tgtacgatgc cgatcatctg aaccettact atgactccgg cacttttatg   300
tcccattttt acgatccgga cacgcaaacg aactacgcag ggttgtcgta cccgacagca   360
cgccaaacag gggcaaaata ttttacgatt gcctcgaatg actatcaagc aggggatatg   420
tcggatgcat tttacaattt aggcttgtcc ctgcactatt tcacagatgt cacgatgccg   480
cttcatgccg gaaatatttc caatctcgat cacgaagcac ccggctacca tgcgaaactc   540
gaagcgtatg ccgaatcgat tcaaaatcaa gtgacgcctc cgactgccgg actctacaat   600
tgggtctctc cgaatgatcc ggaactctgg attcatcaag cggctgtgca agcgaaatcc   660
gtcttgccgc aagtatggaa cagtgatatc acgagttggt tctggaggc ggctttcagc    720
aattactact cgcaacaatg gcacaacgca gtaaccactc cggtcctgaa tcagttgtcg   780
caagcggagg cagagaccgc cggatatatt gatctgttct tccgtgtaaa cggttag      837
```

<210> SEQ ID NO 19
<211> LENGTH: 278
<212> TYPE: PRT
<213> ORGANISM: Bacillus sp
<220> FEATURE:
<221> NAME/KEY: SIGNAL
<222> LOCATION: (1)..(33)

<400> SEQUENCE: 19

Met Lys His His Arg Phe Arg Thr Asn Leu Leu Ser Ala Leu Ser Val
1               5                   10                  15

Ser Ser Ile Val Ile Thr Ser Ile Ile Gly Ser Thr Gln Thr Thr Tyr
            20                  25                  30

Ala Trp Ser Ala Asp Ala Pro His Asp Pro Asn Gln Ser Thr His Leu
        35                  40                  45

Phe Ile Val Asn Gly Ala Val Asn Leu Val Ala Asn Asn Thr Asp Pro
    50                  55                  60

Gln Ile Asn Lys Pro Thr Ala Leu Leu Gln Gln Trp Arg Ser Gln Trp
65                  70                  75                  80

Glu Gln Gly Leu Tyr Asp Ala Asp His Leu Asn Pro Tyr Tyr Asp Ser
                85                  90                  95

Gly Thr Phe Met Ser His Phe Tyr Asp Pro Asp Thr Gln Thr Asn Tyr
            100                 105                 110

Ala Gly Leu Ser Tyr Pro Thr Ala Arg Gln Thr Gly Ala Lys Tyr Phe
        115                 120                 125

Thr Ile Ala Ser Asn Asp Tyr Gln Ala Gly Asp Met Ser Asp Ala Phe
    130                 135                 140

Tyr Asn Leu Gly Leu Ser Leu His Tyr Phe Thr Asp Val Thr Met Pro
145                 150                 155                 160

Leu His Ala Gly Asn Ile Ser Asn Leu Asp His Glu Ala Pro Gly Tyr
                165                 170                 175

His Ala Lys Leu Glu Ala Tyr Ala Glu Ser Ile Gln Asn Gln Val Thr
            180                 185                 190

Pro Pro Thr Ala Gly Leu Tyr Asn Trp Val Ser Pro Asn Asp Pro Glu
        195                 200                 205

Leu Trp Ile His Gln Ala Val Gln Ala Lys Ser Val Leu Pro Gln
    210                 215                 220

Val Trp Asn Ser Asp Ile Thr Ser Trp Phe Trp Glu Ala Ala Phe Ser
225                 230                 235                 240

Asn Tyr Tyr Ser Gln Gln Trp His Asn Ala Val Thr Thr Pro Val Leu
                245                 250                 255

Asn Gln Leu Ser Gln Ala Glu Ala Glu Thr Ala Gly Tyr Ile Asp Leu
            260                 265                 270

Phe Phe Arg Val Asn Gly
        275

<210> SEQ ID NO 20
<211> LENGTH: 246
<212> TYPE: PRT
<213> ORGANISM: Artificial Sequence
<220> FEATURE:
<223> OTHER INFORMATION: variant

<400> SEQUENCE: 20

Ala Trp Ser Ala Asp Ala Pro His Asp Pro Asn Gln Ser Thr His Leu
1               5                   10                  15

Phe Ile Val Asn Gly Ala Val Asn Leu Val Ala Asn Asn Thr Asp Pro
            20                  25                  30

Gln Ile Asn Lys Pro Thr Ala Leu Leu Gln Gln Trp Arg Ser Gln Trp
        35                  40                  45

Glu Gln Gly Leu Tyr Asp Ala Asp His Leu Asn Pro Tyr Tyr Asp Ser
    50                  55                  60

Gly Thr Phe Met Ser His Phe Tyr Asp Pro Thr Gln Thr Asn Tyr
65                  70                  75                  80

Ala Gly Leu Ser Tyr Pro Thr Ala Arg Gln Thr Gly Ala Lys Tyr Phe
                85                  90                  95

Thr Ile Ala Ser Asn Asp Tyr Gln Ala Gly Asp Met Ser Asp Ala Phe
            100                 105                 110

Tyr Asn Leu Gly Leu Ser Leu His Tyr Phe Thr Asp Val Thr Met Pro
        115                 120                 125

Leu His Ala Gly Asn Ile Ser Asn Leu Asp His Glu Ala Pro Gly Tyr
    130                 135                 140

His Ala Lys Leu Glu Ala Tyr Ala Glu Ser Ile Gln Asn Gln Val Thr
145                 150                 155                 160

Pro Pro Thr Ala Gly Leu Tyr Asn Trp Val Ser Pro Asn Asp Pro Glu
                165                 170                 175

Leu Trp Ile His Gln Ala Val Gln Ala Lys Ser Val Leu Pro Gln
            180                 185                 190

Val Trp Asn Ser Asp Ile Thr Ser Trp Phe Trp Glu Ala Ala Phe Ser
        195                 200                 205

Asn Tyr Tyr Ser Gln Gln Trp His Asn Ala Val Thr Thr Pro Val Leu
    210                 215                 220

Asn Gln Leu Ser Gln Ala Glu Ala Glu Thr Ala Gly Tyr Ile Asp Leu
225                 230                 235                 240

Phe Phe Arg Val Asn Gly
                245

<210> SEQ ID NO 21
<211> LENGTH: 852
<212> TYPE: DNA
<213> ORGANISM: Bacillus thuringiensis

<400> SEQUENCE: 21

```
atgaaaaaga aagtacttgc tttagcagca gctattacat tagtagctcc tttacaaagc    60
gttgcatttg ctcatgaaaa tgatggggga agtaaaataa aaatagttca ccgctggtct   120
gctgaagata acataaaga aggcgtaaat tctcatttat ggattgtaaa ccgtgcgatt   180
gatattatgt ctcgcaatac aacacttgta aaacaagatc gagttgcaca attaaatgaa   240
tggcgtacag agttagagaa cggtatttat gctgctgact atgaaaatcc ttattatgat   300
aatagcacat ttgcttcaca tttctatgat ccagacaatg gaaaaacata tattccattt   360
gcaaagcagg caaaagaaac tggagctaaa tattttaaat tagcgggtga atcatacaaa   420
aataaagata tgaaacaagc attcttctat ttaggattat ctcttcatta tttaggagat   480
gtaaatcaac cgatgcatgc ggcaaacttt acaaatcttt cgtatccaca aggattccat   540
tctaaatatg aaaactttgt agatacgata aaagataatt ataaagtaac ggatggaaat   600
ggatattgga attggaaagg tacaaatcca gaagattgga tccatggagc ggcagtagtg   660
gcgaaacaag attactctgg aattgtaaat gataatacga aagattggtt cgtaaaagca   720
gctgtgtcac aagaatatgc agataaatgg cgtgctgaag ttacaccgat gacaggtaag   780
cgattaatgg atgcacaacg tgttactgct ggatacattc agctttggtt tgatacgtac   840
ggagatcgtt aa                                                       852
```

<210> SEQ ID NO 22
<211> LENGTH: 283
<212> TYPE: PRT
<213> ORGANISM: Bacillus thuringiensis
<220> FEATURE:
<221> NAME/KEY: SIGNAL
<222> LOCATION: (1)..(24)
<220> FEATURE:
<221> NAME/KEY: PROPEP
<222> LOCATION: (25)..(38)

<400> SEQUENCE: 22

```
Met Lys Lys Lys Val Leu Ala Leu Ala Ala Ala Ile Thr Leu Val Ala
1               5                   10                  15
Pro Leu Gln Ser Val Ala Phe Ala His Glu Asn Asp Gly Gly Ser Lys
            20                  25                  30
Ile Lys Ile Val His Arg Trp Ser Ala Glu Asp Lys His Lys Glu Gly
        35                  40                  45
Val Asn Ser His Leu Trp Ile Val Asn Arg Ala Ile Asp Ile Met Ser
    50                  55                  60
Arg Asn Thr Thr Leu Val Lys Gln Asp Arg Val Ala Gln Leu Asn Glu
65                  70                  75                  80
Trp Arg Thr Glu Leu Glu Asn Gly Ile Tyr Ala Ala Asp Tyr Glu Asn
                85                  90                  95
Pro Tyr Tyr Asp Asn Ser Thr Phe Ala Ser His Phe Tyr Asp Pro Asp
            100                 105                 110
Asn Gly Lys Thr Tyr Ile Pro Phe Ala Lys Gln Ala Lys Glu Thr Gly
        115                 120                 125
Ala Lys Tyr Phe Lys Leu Ala Gly Glu Ser Tyr Lys Asn Lys Asp Met
    130                 135                 140
```

```
Lys Gln Ala Phe Phe Tyr Leu Gly Leu Ser Leu His Tyr Leu Gly Asp
145                 150                 155                 160

Val Asn Gln Pro Met His Ala Ala Asn Phe Thr Asn Leu Ser Tyr Pro
                165                 170                 175

Gln Gly Phe His Ser Lys Tyr Glu Asn Phe Val Asp Thr Ile Lys Asp
            180                 185                 190

Asn Tyr Lys Val Thr Asp Gly Asn Gly Tyr Trp Asn Trp Lys Gly Thr
        195                 200                 205

Asn Pro Glu Asp Trp Ile His Gly Ala Ala Val Val Ala Lys Gln Asp
    210                 215                 220

Tyr Ser Gly Ile Val Asn Asp Asn Thr Lys Asp Trp Phe Val Lys Ala
225                 230                 235                 240

Ala Val Ser Gln Glu Tyr Ala Asp Lys Trp Arg Ala Glu Val Thr Pro
                245                 250                 255

Met Thr Gly Lys Arg Leu Met Asp Ala Gln Arg Val Thr Ala Gly Tyr
            260                 265                 270

Ile Gln Leu Trp Phe Asp Thr Tyr Gly Asp Arg
        275                 280
```

<210> SEQ ID NO 23
<211> LENGTH: 852
<212> TYPE: DNA
<213> ORGANISM: Bacillus pseudomycoides

<400> SEQUENCE: 23

```
atgaaaaaga aagtattagc cttagcagca gctattacat tagtagcacc attgcaaagt      60
gtagcgtttg cccatgaaaa tgagggcgga aataaggtaa gagtaattca atattggtct     120
gctgaagata acatgcaga aggtgtaaac tcccatttat ggattgtcaa tcgtgcaatt      180
gatattatgt ctcgtaatac aacggttgta aaacaagatc aagttgcagt attaaatgaa     240
tggcgtacag agttagagaa tggtatatat gctgctgatt atgaaaaccc ttactatgat     300
aacagtacat ttgcttctca tttctacgag cctgatacag ggaagacata tatacctttt     360
gctaagcagg caaaagaaac tggggctaaa tattttaaac ttgctggtga agcttatcaa     420
aagcaagata tgaaacaagc attcttctat ttgggtttat cccttcatta cttaggcgat     480
gtcaatcaac cgatgcatgc agcaaacttt acaaatcttt cttatccaca aggtttccac     540
tccaaatatg aaaattttgt agatacaata aaaaataatt ataaagtggc tgatggaaat     600
ggatattgga attggaaagg agtaaatcct gaagactgga ttcatggagc ggctgtagct     660
gctaagcaag attatgctgg tattgtaaat ggcactacaa aagattggtt cgtaagagcg     720
gcagtttcac aagaatatgc agataaatgg cgtgcagaag ttacactaac aacaggaaaa     780
cgtttagtag aagcacagcg tgtcacagcg ggatatattc agctttggtt tgatacgtat     840
gtaaatcgct ag                                                         852
```

<210> SEQ ID NO 24
<211> LENGTH: 283
<212> TYPE: PRT
<213> ORGANISM: Bacillus pseudomycoides
<220> FEATURE:
<221> NAME/KEY: SIGNAL
<222> LOCATION: (1)..(24)
<220> FEATURE:
<221> NAME/KEY: PROPEP
<222> LOCATION: (25)..(38)

<400> SEQUENCE: 24

Met Lys Lys Lys Val Leu Ala Leu Ala Ala Ala Ile Thr Leu Val Ala
1               5                   10                  15

Pro Leu Gln Ser Val Ala Phe Ala His Glu Asn Glu Gly Gly Asn Lys
            20                  25                  30

Val Arg Val Ile Gln Tyr Trp Ser Ala Glu Asp Lys His Ala Glu Gly
        35                  40                  45

Val Asn Ser His Leu Trp Ile Val Asn Arg Ala Ile Asp Ile Met Ser
    50                  55                  60

Arg Asn Thr Thr Val Val Lys Gln Asp Gln Val Ala Val Leu Asn Glu
65                  70                  75                  80

Trp Arg Thr Glu Leu Glu Asn Gly Ile Tyr Ala Ala Asp Tyr Glu Asn
                85                  90                  95

Pro Tyr Tyr Asp Asn Ser Thr Phe Ala Ser His Phe Tyr Glu Pro Asp
                100                 105                 110

Thr Gly Lys Thr Tyr Ile Pro Phe Ala Lys Gln Ala Lys Glu Thr Gly
            115                 120                 125

Ala Lys Tyr Phe Lys Leu Ala Gly Glu Ala Tyr Gln Lys Gln Asp Met
        130                 135                 140

Lys Gln Ala Phe Phe Tyr Leu Gly Leu Ser Leu His Tyr Leu Gly Asp
145                 150                 155                 160

Val Asn Gln Pro Met His Ala Ala Asn Phe Thr Asn Leu Ser Tyr Pro
                165                 170                 175

Gln Gly Phe His Ser Lys Tyr Glu Asn Phe Val Asp Thr Ile Lys Asn
                180                 185                 190

Asn Tyr Lys Val Ala Asp Gly Asn Gly Tyr Trp Asn Trp Lys Gly Val
            195                 200                 205

Asn Pro Glu Asp Trp Ile His Gly Ala Ala Val Ala Ala Lys Gln Asp
        210                 215                 220

Tyr Ala Gly Ile Val Asn Gly Thr Thr Lys Asp Trp Phe Val Arg Ala
225                 230                 235                 240

Ala Val Ser Gln Glu Tyr Ala Asp Lys Trp Arg Ala Glu Val Thr Leu
                245                 250                 255

Thr Thr Gly Lys Arg Leu Val Glu Ala Gln Arg Val Thr Ala Gly Tyr
            260                 265                 270

Ile Gln Leu Trp Phe Asp Thr Tyr Val Asn Arg
        275                 280

<210> SEQ ID NO 25
<211> LENGTH: 260
<212> TYPE: PRT
<213> ORGANISM: Artificial Sequence
<220> FEATURE:
<223> OTHER INFORMATION: variant

<400> SEQUENCE: 25

Ala His Glu Asn Glu Gly Gly Asn Lys Val Arg Val Ile Gln Tyr Trp
1               5                   10                  15

Ser Ala Glu Asp Lys His Ala Glu Gly Val Asn Ser His Leu Trp Ile
            20                  25                  30

Val Asn Arg Ala Ile Asp Ile Met Ser Arg Asn Thr Thr Val Val Lys
        35                  40                  45

Gln Asp Gln Val Ala Val Leu Asn Glu Trp Arg Thr Glu Leu Glu Asn
    50                  55                  60

Gly Ile Tyr Ala Ala Asp Tyr Glu Asn Pro Tyr Tyr Asp Asn Ser Thr
65                  70                  75                  80

Phe Ala Ser His Phe Tyr Glu Pro Asp Thr Gly Lys Thr Tyr Ile Pro
                85                  90                  95

Phe Ala Lys Gln Ala Lys Glu Thr Gly Ala Lys Tyr Phe Lys Leu Ala
            100                 105                 110

Gly Glu Ala Tyr Gln Lys Gln Asp Met Lys Gln Ala Phe Phe Tyr Leu
        115                 120                 125

Gly Leu Ser Leu His Tyr Leu Gly Asp Val Asn Gln Pro Met His Ala
    130                 135                 140

Ala Asn Phe Thr Asn Leu Ser Tyr Pro Gln Gly Phe His Ser Lys Tyr
145                 150                 155                 160

Glu Asn Phe Val Asp Thr Ile Lys Asn Asn Tyr Lys Val Ala Asp Gly
                165                 170                 175

Asn Gly Tyr Trp Asn Trp Lys Gly Val Asn Pro Glu Asp Trp Ile His
            180                 185                 190

Gly Ala Ala Val Ala Ala Lys Gln Asp Tyr Ala Gly Ile Val Asn Gly
        195                 200                 205

Thr Thr Lys Asp Trp Phe Val Arg Ala Ala Val Ser Gln Glu Tyr Ala
    210                 215                 220

Asp Lys Trp Arg Ala Glu Val Thr Leu Thr Thr Gly Lys Arg Leu Val
225                 230                 235                 240

Glu Ala Gln Arg Val Thr Ala Gly Tyr Ile Gln Leu Trp Phe Asp Thr
                245                 250                 255

Tyr Val Asn Arg
            260

<210> SEQ ID NO 26
<211> LENGTH: 852
<212> TYPE: DNA
<213> ORGANISM: Bacillus mycoides

<400> SEQUENCE: 26
atgaaaaaga aagtattagc cttagcagca gctattacat tagtagcacc attgcaaagt      60
gtagcgtttg cccatgaaaa tgagggcgga aataaggtaa gagtaattca atattggtct     120
gctgaagata acatgcaga aggtgtaaac tcccatttat ggattgtcaa tcgtgcaatt     180
gatattatgt ctcgtaatac aacggttgta aaacaagatc aagttgcatt attaaatgaa     240
tggcgtacag agttagagaa tggtatatat gctgctgatt atgaaaaccc ttattatgat     300
aacagtacat ttgcttctca tttctacgat cctgacacag ggaagacata taccctttt     360
gctaagcagg caaaagaaac tggggctaaa tattttaaac ttgctggtga agcctatcaa     420
aagcaagaaa taaaacaagc attcttctat ttaggcttat cgcttcatta cttaggagat     480
gtaaatcaac caatgcatgc agcaaacttt acaaatcttt cttatccaca aggtttccac     540
tccaaatatg aaaattttgt agatacaata aaaaataatt ataaagtggc tgatggaaat     600
ggatattgga attggaaagg agtaaatcct gaagactgga ttcatggagc ggctgtagct     660
gctaagcaag attatgctgg tattgtaaat ggcactacaa agattggtt cgtaagagcg     720
gcagttttcac aagaatatgc agataaatgg cgtgcagaag ttacactaac aacaggaaaa     780
cgtttagtag aagcacagcg tgtcacagcg ggatatattc agctttggtt tgatacatat     840
gtaaatcgct ag                                                         852

<210> SEQ ID NO 27
<211> LENGTH: 283
<212> TYPE: PRT

<213> ORGANISM: Bacillus mycoides
<220> FEATURE:
<221> NAME/KEY: SIGNAL
<222> LOCATION: (1)..(24)
<220> FEATURE:
<221> NAME/KEY: PROPEP
<222> LOCATION: (25)..(38)

<400> SEQUENCE: 27

Met Lys Lys Lys Val Leu Ala Leu Ala Ala Ala Ile Thr Leu Val Ala
1               5                   10                  15

Pro Leu Gln Ser Val Ala Phe Ala His Glu Asn Glu Gly Gly Asn Lys
            20                  25                  30

Val Arg Val Ile Gln Tyr Trp Ser Ala Glu Asp Lys His Ala Glu Gly
        35                  40                  45

Val Asn Ser His Leu Trp Ile Val Asn Arg Ala Ile Asp Ile Met Ser
    50                  55                  60

Arg Asn Thr Thr Val Val Lys Gln Asp Gln Val Ala Leu Leu Asn Glu
65                  70                  75                  80

Trp Arg Thr Glu Leu Glu Asn Gly Ile Tyr Ala Ala Asp Tyr Glu Asn
                85                  90                  95

Pro Tyr T

-continued

```
aatcatatac gagctaattt aatgaatgag cttaaaaatt tcgataaaca aattgctcaa    300
ggtatatatg atgcggatca taaaaatcca tattatgata ctagtacatt tttatctcat    360
ttttataatc ctgatagaga taatacttat ttgccgggtt ttgctaatgc gaaaataact    420
ggagccaagt atttcaatca atcggtggct gattatcgag aaggtaaatt tgacacagca    480
ttttataaat taggtctagc aatccattat tatacggata ttagtcaacc tatgcacgcc    540
aataatttta ccgcaatatc atacccacca ggctaccact gcgcatatga aaattatgtg    600
gatactatta aacacaatta tcaagcaaca gaagacatgg tagtgaaaag attttgctca    660
gatgacgtga aagtctggct ctatgaaaat gcgaaaagag caaaagccga ctaccctaaa    720
atagtcaatg caaaaactaa aaaatcatat ttagtaggaa attccaaatg gaaaaaggat    780
acagtggaac ctactggagc tagactaaga gattcacagc aaactttggc aggcttttta    840
gaattttggt ccaaaaaaac aaatgaataa                                     870
```

<210> SEQ ID NO 29
<211> LENGTH: 289
<212> TYPE: PRT
<213> ORGANISM: Listeria innocua
<220> FEATURE:
<221> NAME/KEY: SIGNAL
<222> LOCATION: (1)..(27)
<220> FEATURE:
<221> NAME/KEY: PROPEP
<222> LOCATION: (28)..(51)

<400> SEQUENCE: 29

```
Met Lys Phe Lys Lys Val Val Leu Gly Met Cys Leu Thr Ala Ser Val
1               5                   10                  15

Leu Val Phe Pro Val Thr Ile Lys Ala Ser Ala Cys Cys Asp Glu Tyr
            20                  25                  30

Leu Gln Ala Pro Ala Ala Pro His Asp Ile Asp Ser Lys Leu Pro His
        35                  40                  45

Lys Leu Ser Trp Ser Ala Asp Asn Pro Thr Asn Thr Asp Val Asn Thr
    50                  55                  60

His Tyr Trp Leu Phe Lys Gln Ala Glu Lys Ile Leu Ala Lys Asp Val
65                  70                  75                  80

Asn His Ile Arg Ala Asn Leu Met Asn Glu Leu Lys Asn Phe Asp Lys
                85                  90                  95

Gln Ile Ala Gln Gly Ile Tyr Asp Ala Asp His Lys Asn Pro Tyr Tyr
            100                 105                 110

Asp Thr Ser Thr Phe Leu Ser His Phe Tyr Asn Pro Asp Arg Asp Asn
        115                 120                 125

Thr Tyr Leu Pro Gly Phe Ala Asn Ala Lys Ile Thr Gly Ala Lys Tyr
    130                 135                 140

Phe Asn Gln Ser Val Ala Asp Tyr Arg Glu Gly Lys Phe Asp Thr Ala
145                 150                 155                 160

Phe Tyr Lys Leu Gly Leu Ala Ile His Tyr Tyr Thr Asp Ile Ser Gln
                165                 170                 175

Pro Met His Ala Asn Asn Phe Thr Ala Ile Ser Tyr Pro Pro Gly Tyr
            180                 185                 190

His Cys Ala Tyr Glu Asn Tyr Val Asp Thr Ile Lys His Asn Tyr Gln
        195                 200                 205

Ala Thr Glu Asp Met Val Val Lys Arg Phe Cys Ser Asp Asp Val Lys
    210                 215                 220
```

```
Val Trp Leu Tyr Glu Asn Ala Lys Arg Ala Lys Ala Asp Tyr Pro Lys
225                 230                 235                 240

Ile Val Asn Ala Lys Thr Lys Lys Ser Tyr Leu Val Gly Asn Ser Lys
                245                 250                 255

Trp Lys Lys Asp Thr Val Glu Pro Thr Gly Ala Arg Leu Arg Asp Ser
                260                 265                 270

Gln Gln Thr Leu Ala Gly Phe Leu Glu Phe Trp Ser Lys Lys Thr Asn
            275                 280                 285

Glu

<210> SEQ ID NO 30
<211> LENGTH: 263
<212> TYPE: PRT
<213> ORGANISM: Artificial Sequence
<220> FEATURE:
<223> OTHER INFORMATION: variant
<220> FEATURE:
<221> NAME/KEY: PROPEP
<222> LOCATION: (1)..(25)

<400> SEQUENCE: 30

Ala Cys Cys Asp Glu Tyr Leu Gln Ala Pro Ala Ala Pro His Asp Ile
1               5                   10                  15

Asp Ser Lys Leu Pro His Lys Leu Ser Trp Ser Ala Asp Asn Pro Thr
                20                  25                  30

Asn Thr Asp Val Asn Thr His Tyr Trp Leu Phe Lys Gln Ala Glu Lys
                35                  40                  45

Ile Leu Ala Lys Asp Val Asn His Ile Arg Ala Asn Leu Met Asn Glu
50                  55                  60

Leu Lys Asn Phe Asp Lys Gln Ile Ala Gln Gly Ile Tyr Asp Ala Asp
65                  70                  75                  80

His Lys Asn Pro Tyr Tyr Asp Thr Ser Thr Phe Leu Ser His Phe Tyr
                85                  90                  95

Asn Pro Asp Arg Asp Asn Thr Tyr Leu Pro Gly Phe Ala Asn Ala Lys
                100                 105                 110

Ile Thr Gly Ala Lys Tyr Phe Asn Gln Ser Val Ala Asp Tyr Arg Glu
                115                 120                 125

Gly Lys Phe Asp Thr Ala Phe Tyr Lys Leu Gly Leu Ala Ile His Tyr
                130                 135                 140

Tyr Thr Asp Ile Ser Gln Pro Met His Ala Asn Asn Phe Thr Ala Ile
145                 150                 155                 160

Ser Tyr Pro Pro Gly Tyr His Cys Ala Tyr Glu Asn Tyr Val Asp Thr
                165                 170                 175

Ile Lys His Asn Tyr Gln Ala Thr Glu Asp Met Val Val Lys Arg Phe
                180                 185                 190

Cys Ser Asp Asp Val Lys Val Trp Leu Tyr Glu Asn Ala Lys Arg Ala
                195                 200                 205

Lys Ala Asp Tyr Pro Lys Ile Val Asn Ala Lys Thr Lys Lys Ser Tyr
                210                 215                 220

Leu Val Gly Asn Ser Lys Trp Lys Lys Asp Thr Val Glu Pro Thr Gly
225                 230                 235                 240

Ala Arg Leu Arg Asp Ser Gln Gln Thr Leu Ala Gly Phe Leu Glu Phe
                245                 250                 255

Trp Ser Lys Lys Thr Asn Glu
                260
```

```
<210> SEQ ID NO 31
<211> LENGTH: 849
<212> TYPE: DNA
<213> ORGANISM: Artificial Sequence
<220> FEATURE:
<223> OTHER INFORMATION: variant

<400> SEQUENCE: 31
atgaaaaaga aagtattagc actagcagct atggttgctt tagctgcgcc agttcaaagt      60
gtagtatttg cacaaacaaa taatagtgaa agtcctgcac cgattttaag atggtcagct     120
gaggataagc ataatgaggg gattaactct catttgtgga ttgtaaatcg tgcaattgac     180
atcatgtctc gtaatacaac gattgtgaat ccgaatgaaa ctgcattatt aaatgagtgg     240
cgtgctgatt tagaaaatgg tatttattct gctgattacg agaatcctta ttatgatgat     300
agtacatatg cttctcactt ttatgatccg gatactggaa caacatatat tccttttgcg     360
aaacatgcaa agaaacagg cgcaaaatat tttaaccttg ctggtcaagc ataccaaaat      420
caagatatgc agcaagcatt cttctactta ggattatcgc ttcattattt aggagatgtg     480
aatcagccaa tgcatgcagc atcttttacg gatctttctt atccaatggg tttccattct     540
aaatacgaaa attttgttga taaataaaa aataactata ttgtttcaga tagcaatgga     600
tattggaatt ggaaaggagc aaacccagaa gattggattg aaggagcagc ggtagcagct     660
aaacaagatt atcctggcgt tgtgaacgat acgacaaaag attggtttgt aaaagcagcc     720
gtatctcaag aatatgcaga taaatggcgt gcggaagtaa caccggtgac aggaaagcgt     780
ttaatggaag cgcagcgcgt tacagctggt tatattcatt tgtggtttga tacgtatgta     840
aatcgctaa                                                             849

<210> SEQ ID NO 32
<211> LENGTH: 282
<212> TYPE: PRT
<213> ORGANISM: Artificial
<220> FEATURE:
<223> OTHER INFORMATION: variant
<220> FEATURE:
<221> NAME/KEY: SIGNAL
<222> LOCATION: (1)..(20)
<220> FEATURE:
<221> NAME/KEY: PROPEP
<222> LOCATION: (21)..(37)

<400> SEQUENCE: 32

Met Lys Lys Lys Val Leu Ala Leu Ala Ala Met Val Ala Leu Ala Ala
1               5                   10                  15

Pro Val Gln Ser Val Val Phe Ala Gln Thr Asn Asn Ser Glu Ser Pro
            20                  25                  30

Ala Pro Ile Leu Arg Trp Ser Ala Glu Asp Lys His Asn Glu Gly Ile
        35                  40                  45

Asn Ser His Leu Trp Ile Val Asn Arg Ala Ile Asp Ile Met Ser Arg
    50                  55                  60

Asn Thr Thr Ile Val Asn Pro Asn Glu Thr Ala Leu Leu Asn Glu Trp
65                  70                  75                  80

Arg Ala Asp Leu Glu Asn Gly Ile Tyr Ser Ala Asp Tyr Glu Asn Pro
                85                  90                  95

Tyr Tyr Asp Asp Ser Thr Tyr Ala Ser His Phe Tyr Asp Pro Asp Thr
            100                 105                 110

Gly Thr Thr Tyr Ile Pro Phe Ala Lys His Ala Lys Glu Thr Gly Ala
        115                 120                 125
```

```
Lys Tyr Phe Asn Leu Ala Gly Gln Ala Tyr Gln Asn Gln Asp Met Gln
    130                 135                 140

Gln Ala Phe Phe Tyr Leu Gly Leu Ser Leu His Tyr Leu Gly Asp Val
145                 150                 155                 160

Asn Gln Pro Met His Ala Ala Ser Phe Thr Asp Leu Ser Tyr Pro Met
                165                 170                 175

Gly Phe His Ser Lys Tyr Glu Asn Phe Val Asp Thr Ile Lys Asn Asn
                180                 185                 190

Tyr Ile Val Ser Asp Ser Asn Gly Tyr Trp Asn Trp Lys Gly Ala Asn
                195                 200                 205

Pro Glu Asp Trp Ile Glu Gly Ala Val Ala Ala Lys Gln Asp Tyr
    210                 215                 220

Pro Gly Val Val Asn Asp Thr Thr Lys Asp Trp Phe Val Lys Ala Ala
225                 230                 235                 240

Val Ser Gln Glu Tyr Ala Asp Lys Trp Arg Ala Glu Val Thr Pro Val
                245                 250                 255

Thr Gly Lys Arg Leu Met Glu Ala Gln Arg Val Thr Ala Gly Tyr Ile
            260                 265                 270

His Leu Trp Phe Asp Thr Tyr Val Asn Arg
            275                 280

<210> SEQ ID NO 33
<211> LENGTH: 27
<212> TYPE: PRT
<213> ORGANISM: Artificial Sequence
<220> FEATURE:
<223> OTHER INFORMATION: signal peptide

<400> SEQUENCE: 33

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 34
<211> LENGTH: 1020
<212> TYPE: DNA
<213> ORGANISM: Amycolatopsis azurea

<400> SEQUENCE: 34
atgaaactcg tccccgcggt atccctcgtc ggcgtgatct tggcggcttc gctgtccgga      60
acggtcgcga acgccgacgc cgccaaggtc tcccacgtga caacggtcgg cgtccacaac     120
acctacgaga ccggtgccta cgactacctg gcgcgctcgc tggacgccgg tacctcgctg     180
atcgaactcg acgtctggcc gaacatcatc actcgcgagt ggaaagtgag tcactcgaac     240
ccgttgggga caacaacaa ctgcgtcgcg gcgagtacgc cgtcgcagtt gtactccggt     300
gggcggaaca agaacctcga acactgcctc gatgacatcc gcgtctggct gggcgcgcat     360
ccggacagca aaccggtcac gctcaaactg gagatgaaga ccgggttcgc cgacaaccgc     420
ggcctcggcc cggacgaact cgacgcgtcc atccgggcac atctgggcag tacggtgttc     480
cggccggcgg acctgctcgg cgggtacgcg acgctcgacg acgcggccaa agcggacaac     540
tggccgtccc tggacgcgct gcggggcaag gtgatcatcg agatcatccc cggcacggtc     600
gaagagggaa atccgacgga cacgctcaag accgacgtcg agtacgggcg atatctgcgg     660
tcgctcaagg acgcgggccg cgtcggcgag gtgcagatct cccgacggt gcacggcgcg     720 gcacccggcg acccgcgcac gaagtacgcc gacgccgggc tgcggccgtg gttcgtggtc     780
```

```
ttcgacggcg acgccaccgc gttcctgacg cagaccgggc ccggctggta cgacgacaac    840
cactactacg tggtgatgac cgacgcgcac aacgtcgcgc cggccatcga ctcccgtgcc    900
cccacggtgg accaggcgag cgcgcgagcg gccctgctgg cgaagaacca cgcttcggtg    960
ctgacctcgg attggacggg gctgaccacc gtgctgccgc aggtacttcc gcgcggctag   1020
```

<210> SEQ ID NO 35
<211> LENGTH: 339
<212> TYPE: PRT
<213> ORGANISM: Amycolatopsis azurea
<220> FEATURE:
<221> NAME/KEY: SIGNAL
<222> LOCATION: (1)..(27)

<400> SEQUENCE: 35

```
Met Lys Leu Val Pro Ala Val Ser Leu Val Gly Val Ile Leu Ala Ala
1               5                   10                  15

Ser Leu Ser Gly Thr Val Ala Asn Ala Asp Ala Ala Lys Val Ser His
            20                  25                  30

Val Thr Thr Val Gly Val His Asn Thr Tyr Glu Thr Gly Ala Tyr Asp
        35                  40                  45

Tyr Leu Ala Arg Ser Leu Asp Ala Gly Thr Ser Leu Ile Glu Leu Asp
    50                  55                  60

Val Trp Pro Asn Ile Ile Thr Arg Glu Trp Lys Val Ser His Ser Asn
65                  70                  75                  80

Pro Leu Gly Asn Asn Asn Cys Val Ala Ala Ser Thr Pro Ser Gln
                85                  90                  95

Leu Tyr Ser Gly Gly Arg Asn Lys Asn Leu Glu His Cys Leu Asp Asp
            100                 105                 110

Ile Arg Val Trp Leu Gly Ala His Pro Asp Ser Lys Pro Val Thr Leu
        115                 120                 125

Lys Leu Glu Met Lys Thr Gly Phe Ala Asp Asn Arg Gly Leu Gly Pro
    130                 135                 140

Asp Glu Leu Asp Ala Ser Ile Arg Ala His Leu Gly Ser Thr Val Phe
145                 150                 155                 160

Arg Pro Ala Asp Leu Leu Gly Gly Tyr Ala Thr Leu Asp Asp Ala Ala
                165                 170                 175

Lys Ala Asp Asn Trp Pro Ser Leu Asp Ala Leu Arg Gly Lys Val Ile
            180                 185                 190

Ile Glu Ile Ile Pro Gly Thr Val Glu Glu Gly Asn Pro Thr Asp Thr
        195                 200                 205

Leu Lys Thr Asp Val Glu Tyr Gly Arg Tyr Leu Arg Ser Leu Lys Asp
    210                 215                 220

Ala Gly Arg Val Gly Glu Val Gln Ile Phe Pro Thr Val His Gly Ala
225                 230                 235                 240

Ala Pro Gly Asp Pro Arg Thr Lys Tyr Ala Asp Ala Gly Leu Arg Pro
                245                 250                 255

Trp Phe Val Val Phe Asp Gly Asp Ala Thr Ala Phe Leu Thr Gln Thr
            260                 265                 270

Gly Pro Gly Trp Tyr Asp Asp Asn His Tyr Tyr Val Val Met Thr Asp
        275                 280                 285

Ala His Asn Val Ala Pro Ala Ile Asp Ser Arg Ala Pro Thr Val Asp
    290                 295                 300

Gln Ala Ser Ala Arg Ala Ala Leu Leu Ala Lys Asn His Ala Ser Val
305                 310                 315                 320
```

```
Leu Thr Ser Asp Trp Thr Gly Leu Thr Thr Val Leu Pro Gln Val Leu
                325                 330                 335

Pro Arg Gly

<210> SEQ ID NO 36
<211> LENGTH: 313
<212> TYPE: PRT
<213> ORGANISM: Artificial sequence
<220> FEATURE:
<223> OTHER INFORMATION: Mature polypeptide with extra N term. alanine

<400> SEQUENCE: 36

Ala Ala Lys Val Ser His Val Thr Thr Val Gly Val His Asn Thr Tyr
1               5                   10                  15

Glu Thr Gly Ala Tyr Asp Tyr Leu Ala Arg Ser Leu Asp Ala Gly Thr
            20                  25                  30

Ser Leu Ile Glu Leu Asp Val Trp Pro Asn Ile Ile Thr Arg Glu Trp
        35                  40                  45

Lys Val Ser His Ser Asn Pro Leu Gly Asn Asn Asn Cys Val Ala
    50                  55                  60

Ala Ser Thr Pro Ser Gln Leu Tyr Ser Gly Gly Arg Asn Lys Asn Leu
65                  70                  75                  80

Glu His Cys Leu Asp Asp Ile Arg Val Trp Leu Gly Ala His Pro Asp
                85                  90                  95

Ser Lys Pro Val Thr Leu Lys Leu Glu Met Lys Thr Gly Phe Ala Asp
            100                 105                 110

Asn Arg Gly Leu Gly Pro Asp Glu Leu Asp Ala Ser Ile Arg Ala His
        115                 120                 125

Leu Gly Ser Thr Val Phe Arg Pro Ala Asp Leu Leu Gly Gly Tyr Ala
130                 135                 140

Thr Leu Asp Asp Ala Ala Lys Ala Asp Asn Trp Pro Ser Leu Asp Ala
145                 150                 155                 160

Leu Arg Gly Lys Val Ile Glu Ile Ile Pro Gly Thr Val Glu Glu
                165                 170                 175

Gly Asn Pro Thr Asp Thr Leu Lys Thr Asp Val Glu Tyr Gly Arg Tyr
            180                 185                 190

Leu Arg Ser Leu Lys Asp Ala Gly Arg Val Gly Glu Val Gln Ile Phe
        195                 200                 205

Pro Thr Val His Gly Ala Ala Pro Gly Asp Pro Arg Thr Lys Tyr Ala
    210                 215                 220

Asp Ala Gly Leu Arg Pro Trp Phe Val Phe Asp Gly Asp Ala Thr
225                 230                 235                 240

Ala Phe Leu Thr Gln Thr Gly Pro Gly Trp Tyr Asp Asp Asn His Tyr
                245                 250                 255

Tyr Val Val Met Thr Asp Ala His Asn Val Ala Pro Ile Asp Ser
            260                 265                 270

Arg Ala Pro Thr Val Asp Gln Ala Ser Ala Arg Ala Ala Leu Leu Ala
        275                 280                 285

Lys Asn His Ala Ser Val Leu Thr Ser Asp Trp Thr Gly Leu Thr Thr
    290                 295                 300

Val Leu Pro Gln Val Leu Pro Arg Gly
305                 310

<210> SEQ ID NO 37
<211> LENGTH: 771
```

```
<212> TYPE: DNA
<213> ORGANISM: Artificial sequence
<220> FEATURE:
<223> OTHER INFORMATION: Synthetic gene

<400> SEQUENCE: 37
gaagatgacg cacaaccgcc tattacagca aaatggtcag cggaagatcc gcatcatgaa      60
gatacaaata cacatctgtg gattgttcgc catgccatgg agattatggc gaataacaaa     120
gatgttgtca aacctggcga agtcgaacaa ctgaaacaat ggcaatcaga tctggaacag     180
ggcatttatg atgcagatca tgcaaacccg tattatgata atgcaacatt tgcgagccat     240 tttatgatc cggatacagg caaatcatat attccgctgg cagcacatgc aaaaacaaca     300
agcgttaaat actttaaaag agcaggcgaa gcgtatcaga aaggcgatca taaacaagcg     360
ttttacaatc tgggcctggc gctgcattat attggcgatc tgaatcaacc gatgcatgca     420 gcgaattta caaatctgtc atatccgcaa ggctttcata gcaaatatga aactatgtc     480 gatagcttta agaagattac gcggtcaaa gatggcgaag ctattggca ttggaaaggc     540 acaaatccgg aagattggct gcatggcaca gcagttgcag caaaaaaaga ttatccggat     600
atcgtcaacg atacaacgaa agcatggttt gttaaagcag cagtctcaaa tagctatgca     660
gcaaaatggc gtgcagcagt tgttccggca acaggcaaaa gactgacaga agcacaaaga     720
attctggcag gctatatgca actgtggttt gatacatatg tcaacaaata a              771

<210> SEQ ID NO 38
<211> LENGTH: 280
<212> TYPE: PRT
<213> ORGANISM: Bacillus macauensis
<220> FEATURE:
<221> NAME/KEY: Signal
<222> LOCATION: (1)..(24)
<220> FEATURE:
<221> NAME/KEY: PROPEP
<222> LOCATION: (25)..(35)

<400> SEQUENCE: 38

Met Lys Lys Thr Phe Val Ala Val Ala Thr Ala Ala Leu Leu Val Thr
1               5                   10                  15

Gly Phe Gln Gly Asn Ala Ser Ala Glu Asp Asp Ala Gln Pro Pro Ile
            20                  25                  30

Thr Ala Lys Trp Ser Ala Glu Asp Pro His His Glu Asp Thr Asn Thr
        35                  40                  45

His Leu Trp Ile Val Arg His Ala Met Glu Ile Met Ala Asn Asn Lys
    50                  55                  60

Asp Val Val Lys Pro Gly Glu Val Glu Gln Leu Lys Gln Trp Gln Ser
65                  70                  75                  80

Asp Leu Glu Gln Gly Ile Tyr Asp Ala Asp His Ala Asn Pro Tyr Tyr
                85                  90                  95

Asp Asn Ala Thr Phe Ala Ser His Phe Tyr Asp Pro Asp Thr Gly Lys
            100                 105                 110

Ser Tyr Ile Pro Leu Ala Ala His Ala Lys Thr Thr Ser Val Lys Tyr
        115                 120                 125

Phe Lys Arg Ala Gly Glu Ala Tyr Gln Lys Gly Asp His Lys Gln Ala
    130                 135                 140

Phe Tyr Asn Leu Gly Leu Ala Leu His Tyr Ile Gly Asp Leu Asn Gln
145                 150                 155                 160

Pro Met His Ala Ala Asn Phe Thr Asn Leu Ser Tyr Pro Gln Gly Phe
                165                 170                 175
```

```
His Ser Lys Tyr Glu Asn Tyr Val Asp Ser Phe Lys Glu Asp Tyr Ala
            180                 185                 190

Val Lys Asp Gly Glu Gly Tyr Trp His Trp Lys Gly Thr Asn Pro Glu
        195                 200                 205

Asp Trp Leu His Gly Thr Ala Val Ala Ala Lys Lys Asp Tyr Pro Asp
        210                 215                 220

Ile Val Asn Asp Thr Thr Lys Ala Trp Phe Val Lys Ala Ala Val Ser
225                 230                 235                 240

Asn Ser Tyr Ala Ala Lys Trp Arg Ala Ala Val Val Pro Ala Thr Gly
                245                 250                 255

Lys Arg Leu Thr Glu Ala Gln Arg Ile Leu Ala Gly Tyr Met Gln Leu
            260                 265                 270

Trp Phe Asp Thr Tyr Val Asn Lys
        275                 280
```

POLYPEPTIDES HAVING PHOSPHOLIPASE C ACTIVITY AND POLYNUCLEOTIDES ENCODING SAME

CROSS-REFERENCE TO RELATED APPLICATIONS

This application is a divisional of U.S. application Ser. No. 16/423,748 filed May 28, 2019, now U.S. Pat. No. 10,954,469, which is a divisional of U.S. application Ser. No. 15/126,098 filed on Sep. 14, 2016, now U.S. Pat. No. 10,351,795, which is a 35 U.S.C. 371 national application of international application no. PCT/EP2015/055856 filed on Mar. 19, 2015, which claims priority or the benefit under 35 U.S.C. 119 of European application no. 14160698.8 filed on Mar. 19, 2014. The content of each application is fully incorporated herein by reference.

REFERENCE TO A SEQUENCE LISTING

This application contains a Sequence Listing in computer readable form that was submitted as an ASCII text file named 12809-US-PCD 2 SQ Listing.txt (created on Feb. 17, 2021, containing 79 kb), which is incorporated by herein by reference.

BACKGROUND OF THE INVENTION

Field of the Invention

The present invention relates to a method of reducing the phospholipid content in an oil composition and polypeptides having phospholipase C activity capable of catalyzing this reduction. The invention also relates to polynucleotides encoding the polypeptides, nucleic acid constructs, vectors, and host cells comprising the polynucleotides as well as methods of producing and using the polypeptides.

Description of the Related Art

Several types of phospholipases are known which differ in their specificity according to the position of the bond attacked in the phospholipid molecule. Phospholipase A1 (PLA1) removes the 1-position fatty acid to produce free fatty acid and 1-lyso-2-acylphospholipid. Phospholipase A2 (PLA2) removes the 2-position fatty acid to produce free fatty acid and 1-acyl-2-lysophospholipid. The term phospholipase B (PLB) is used for phospholipases having both A1 and A2 activity. Phospholipase C (PLC) removes the phosphate moiety to produce 1,2 diacylglycerol and phosphate ester. Phospholipase D (PLD) produces 1,2-diacylglycero-phosphate and base group (See FIG. 1).

Before consumption vegetable oils are degummed to provide refined storage stable vegetable oils of neutral taste and light color. The degumming process comprises removing the phospholipid components (the gum) from the triglyceride rich oil fraction. The most commonly used processes in the industry are water degumming, chemical/caustic refining and physical refining including acid assisted degumming and/or enzyme assisted degumming. Due to the emulsifying properties of the phospholipid components, the degumming procedure has resulted in a loss of oil, i.e., of triglycerides.

Enzymatic degumming reduces the oils loss due to an efficient hydrolysis of the phospholipids which decrease the emulsifying properties. For a review on enzymatic degumming, see, Dijkstra, 2010, *Eur. J. Lipid Sci. Technol.* 112: 1178. The use of Phospholipase A and/or phospholipase C in degumming is for example described in Clausen, 2001, *Eur. J. Lipid Sci. Technol.* 103 333-340, WO 2003/089620 and WO 2008/094847. Phospholipase A solutions generate lysophospholipid and free fatty acids resulting in oil loss. Phospholipase C on the other hand has the advantage that it produces diglyceride (FIG. 2) which will remain in the oil and therefore will reduce losses. There are four major phospholipids in vegetable oil phosphatidylcholine (PC), phosphatidylethanolamine (PE), phosphatidic acid (PA) and phosphatidyl inositol (PI). Phospholipase C enzymes have different specificity towards these phospholipids. The only known commercially available phospholipase C is Purifine of Verenium/DSM (Dijkstra, 101st AOCS Annual Meeting 10. May 2010) which has specificity towards PC and PE. WO 2007/059927 describes a thermostable *Bacillus* PLC for degumming. WO 2012/062817 describes a fungal PLC with specificity towards all four phospholipids. A PI-specific phospholipase C has been described in WO 2011/046815.

SUMMARY OF THE INVENTION

The present invention provides a method for reducing the content of phospholipids in an oil composition, the method comprising
a) providing an oil composition containing a quantity of phospholipids,
b) contacting said oil composition with a phosphatidylinositol phospholipase C and a PC and PE-specific phospholipase C under conditions sufficient for the enzymes to react with the phospholipids to create diglyceride and phosphate ester, and
c) separating the phosphate ester from the oil composition. In particular, the said phosphatidylinositol phospholipase C is from the genus of *Pseudomonas*.

The invention further provides a polypeptide having phosphatidylinositol phospholipase C activity, selected from the group consisting of:
a) a polypeptide having at least 91% sequence identity to the mature polypeptide of SEQ ID NO: 2;
b) a polypeptide encoded by a polynucleotide that hybridizes under medium stringency conditions with
  i) the mature polypeptide coding sequence of SEQ ID NO: 1, or
  ii) the full-length complement of (i);
c) a polypeptide encoded by a polynucleotide having at least 90% sequence identity to the mature polypeptide coding sequence of SEQ ID NO: 1;
d) a variant of the mature polypeptide of SEQ ID NO: 2 comprising a substitution, deletion, and/or insertion at one or more positions; and
e) a fragment of the polypeptide of (a), (b), (c), or (d) that has phosphatidylinositol phospholipase C activity.

In addition, the invention provides a polypeptide having PC and PE specific phospholipase C activity, selected from the group consisting of:
a) a polypeptide having at least 70% sequence identity to the mature polypeptide of SEQ ID NO: 19;

b) a polypeptide encoded by a polynucleotide that hybridizes under low stringency conditions with
   i) the mature polypeptide coding sequence of SEQ ID NO: 18, or
   ii) the full-length complement of (i);
c) a polypeptide encoded by a polynucleotide having at least 70% sequence identity to the mature polypeptide coding sequence of SEQ ID NO: 18;
d) a variant of the mature polypeptide of SEQ ID NO: 19 comprising a substitution, deletion, and/or insertion at one or more positions; and
e) a fragment of the polypeptide of (a), (b), (c), or (d) that has PC and PE specific phospholipase C activity.

Finally, the invention provides a composition comprising a mixture of a phosphatidylinositol phospholipase C from the genus of *Pseudomonas* and a PC and PE-specific phospholipase C polypeptide.

Definitions

Figure 2:
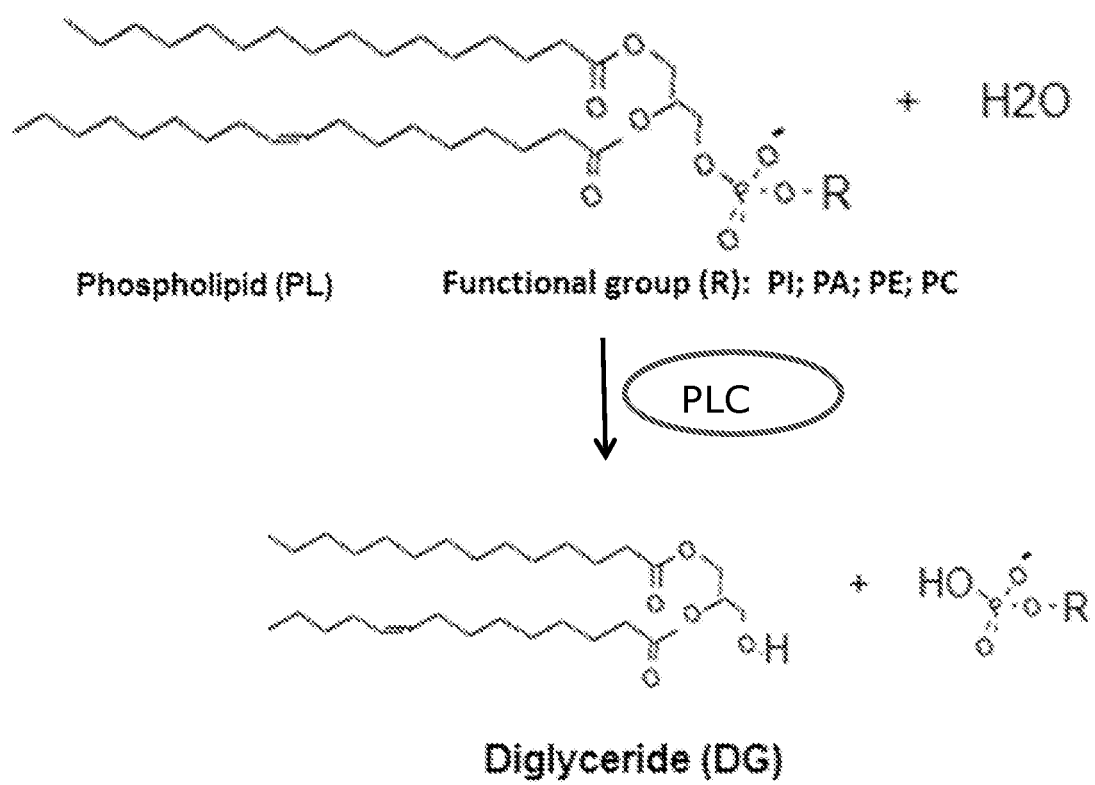
FIG. 2 illustrates the reaction of a phospholipid with a phospholipase C to form diglyceride and a phosphate ester or phosphoric acid.

Phospholipase C activity: The term "phospholipase C activity" or "PLC activity" relates to an enzymatic activity that removes the phosphate ester moiety from a phospholipid to produce a 1,2 diacylglycerol (see FIG. 2). Most PLC enzymes belong to the family of hydrolases and phosphodiesterases and are generally classified as EC 3.1.4.3. Some PLC enzymes are classified in other EC classes, for example PI-specific PLC's. Phospholipase C activity may be determined according to the procedure described in Example 5 or by one of the assays described in the "Assay for phospholipase activity" section.

Figure 1:
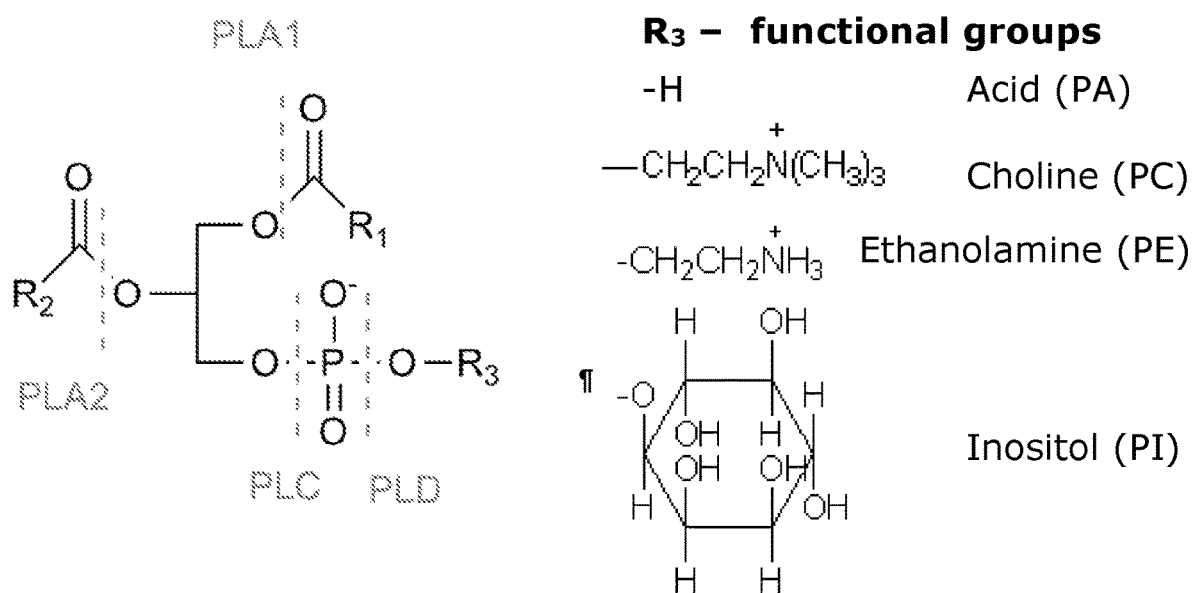
FIG. 1 illustrates where different phospholipases cleave a phospholipid as well as the four major functional groups on phospholipids.

Phospholipase C specificity: The term "phospholipase C specificity" relate to a polypeptide having phospholipase C activity where the activity is specified towards one or more phospholipids, with the four most important once being phosphatidylcholine (PC), phosphatidylethanolamine (PE), phosphatidic acid (PA) and phosphatidyl inositol (PI) (see FIG. 1). Phospholipase C specificity may be determined by $^{32}$P-NMR as described in Example 5.

PC and PE-specific phospholipase C: The term "PC and PE-specific phospholipase C" or "PC, PE-specific phospholipase C" relates to a polypeptide having activity towards phosphatidylcholine (PC), phosphatidylethanolamine (PE). In addition to the PC and PE specificity it may also have some activity towards phosphatidic acid (PA) and phosphatidyl inositol (PI). Preferably a PC and PE specific phospholipase C removes at least 30% PC and at least 30% PE from an oil or fat with at least 100 ppm PC and 100 ppm PE when using the P-NM R assay of Example 5 at the optimal pH of the enzyme and an enzyme dosage of 10 mg/kg. More preferably it removes 40%, 50%, 60%, 70% or 80%, even more preferred it removes 90% and most preferred it removes between 90% and 100% of the PC in the oil or fat and 40%, 50%, 60%, 70% or 80%, even more preferred it removes 90% and most preferred it removes between 90% and 100% of the PE in the oil or fat.

PI-Specific Phospholipase C: The term "PI-specific phospholipase C" or "Phosphatidylinositol phospholipase C" relates to a polypeptide having activity towards phosphatidyl inositol (PI), meaning that its activity towards phosphatidylcholine (PC), phosphatidylethanolamine (PE), phosphatidic acid (PA) is low compared to the PI activity. PI-specific phospholipase C enzymes can either belong to the family of hydrolases and phosphodiesterases classified as EC 3.1.4.11 or to the family of lyases classified as EC 4.6.1.13. PI-specific phospholipase C activity may be determined according to the procedure described in Example 5. Preferably a PI-specific phospholipase C removes at least 30% PI from an oil or fat with at least 50 ppm PI when using the P-NMR assay of Example 5 at the optimal pH of the enzyme and an enzyme dosage of 10 mg/kg. More preferably it removes 40%, 50%, 60%, 70% or 80%, even more preferred it removes 90% and most preferred it removes between 90% and 100% of the PI in the oil or fat.

Preferably a PI-specific Phospholipase C removes at least 20% more PI when compared to the amount of PC, PE or PA it can remove, more preferred at least 30%, 40%, even more preferred at least 50% and most preferred at least 60% more PI when compared to the amount of PC, PE or PA it can remove.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Crude oil: The term "crude oil" refers to (also called a non-degummed oil) a pressed or extracted oil or a mixture thereof from, e.g., vegetable sources, including but not limited to acai oil, almond oil, babassu oil, blackcurrent seed oil, borage seed oil, canola oil, cashew oil, castor oil, coconut oil, coriander oil, corn oil, cottonseed oil, crambe oil, flax seed oil, grape seed oil, hazelnut oil, hempseed oil, jatropha oil, jojoba oil, linseed oil, macadamia nut oil, mango kernel oil, meadowfoam oil, mustard oil, neat's foot oil, olive oil, palm oil, palm kernel oil, palm olein, peanut oil, pecan oil, pine nut oil, pistachio oil, poppy seed oil, rapeseed oil, rice bran oil, safflower oil, sasanqua oil, sesame oil, shea butter, soybean oil, sunflower seed oil, tall oil, tsubaki oil walnut oil, varieties of "natural" oils having altered fatty acid compositions via Genetically Modified Organisms (GMO) or traditional "breading" such as high oleic, low linolenic, or low saturated oils (high oleic canola oil, low linolenic soybean oil or high stearic sunflower oils).

Degummed oil: The term "degummed oil" refers to an oil obtained after removal of nonhydratable phospholipids, hydratable phospholipids, and lecithins (known collectively as "gums") from the oil to produce a degummed oil or fat product that can be used for food production and/or non-food applications, e.g., biodiesel. In certain embodiments, the degummed oil has the phospholipids content of less than 200 ppm phosphorous, such as less than 150 ppm phosphorous, less than 100 ppm phosphorous, less than (or less than about) 50 ppm phosphorous, less than (or less than about) 40 ppm phosphorous, less than (or less than about) 30 ppm phosphorous, less than (or less than about) 20 ppm phosphorous, less than (or less than about) 15 ppm phosphorous, less than (or less than about) 10 ppm phosphorous, less than (or less than about) 7 ppm phosphorous, less than (or less than about) 5 ppm phosphorous, less than (or less than about) 3 ppm phosphorous or less than (or less than about) 1 ppm phosphorous.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has phospholipase C activity. The fragments according to the invention have a size of more than approximately 200 amino acid residues, preferably more than 210 amino acid residues, more preferred more than 220 amino acid residues, more preferred more than 230 amino acid residues (e.g., amino acids 44 to 278 or amino acid 34 to 268 of SEQ ID NO: 19), more preferred more than 240 amino acid residues (e.g., amino acids 39 to 278 or amino acid 34 to 273 of SEQ ID NO: 19), more preferred more than 250 amino acid residues, more preferred more than 260 amino acid residues, more preferred more than 270 amino acid residues, and most preferred more than 280 amino acid residues. In one aspect, a fragment contains at least 290 amino acid residues (e.g., amino acids 33 to 322 or amino acid 26 to 315 of SEQ ID NO: 2), at least 294 amino acid residues (e.g., amino acids 29 to 322 or amino acid 26 to 319 of SEQ ID NO: 2), or at least 296 amino acid residues (e.g., amino acids 27 to 322 or amino acid 26 to 321 of SEQ ID NO: 2).

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 26 to 322 of SEQ ID NO: 2 based on the Signal P version 3 program (Nielsen et al., 1997, *Protein Engineering* 10: 1-6) which predicts that amino acids 1 to 25 of SEQ ID NO: 2 are a signal peptide. When expressed in *Bacillus* as described in Example 1 an additional alanine is added to the N-terminal. The N-terminal sequence of the mature polypeptide (SEQ ID NO: 3) was confirmed to be AQESPAF (See Example 3). In another aspect the mature polypeptide is amino acids 34 to 278 of SEQ ID NO: 19 based on the Signal P version 3 program (Nielsen et al., 1997, *Protein Engineering* 10: 1-6) which predicts that amino acids 1 to 34 of SEQ ID NO: 19 are a signal peptide. When expressed in *Bacillus* as described in Example 1 an additional alanine is added to the N-terminal. The N-terminal sequence of the mature polypeptide (SEQ ID NO: 20) was confirmed to be AWSADAP (See Example 3). It is known in the art that a host cell may produce a mixture of two or more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. In one aspect, a mature polypeptide of SEQ ID NO: 2 contains up to at least 300 amino acid residues (e.g., amino acids 23 to 322 of SEQ ID NO: 2), or at least 299 amino acid residues (e.g., amino acids 24 to 322 of SEQ ID NO: 2) or at least 298 amino acid residues (e.g., amino acids 25 to 322 of SEQ ID NO: 2) or at least 296 amino acid residues (e.g., amino acids 27 to 322 of SEQ ID NO: 2) or at least 295 amino acid residues (e.g., amino acids 28 to 322 of SEQ ID NO: 2). In another aspect, a mature polypeptide of SEQ ID NO: 19 contains up to at least 247 amino acid residues (e.g., amino acids 31 to 278 of SEQ ID NO: 19), or at least 246 amino acid residues (e.g., amino acids 32 to 278 of SEQ ID NO: 19) or at least 244 amino acid residues (e.g., amino acids 35 to 278 of SEQ ID NO: 19) or at least 243 amino acid residues (e.g., amino acids 36 to 278 of SEQ ID NO: 19).

Mature polypeptide coding sequence: The term "mature polypeptide coding sequence" means a polynucleotide that encodes a mature polypeptide having phospholipase activity. In one aspect, the mature polypeptide coding sequence is nucleotides 76 to 966 of SEQ ID NO: 1 based on SignalP (Nielsen et al., 1997, supra)] that predicts nucleotides 1 to 75 of SEQ ID NO: 1 encodes a signal peptide. In another aspect, the mature polypeptide coding sequence is nucleotides 100 to 837 of SEQ ID NO: 18 based on SignalP (Nielsen et al., 1997, supra)] that predicts nucleotides 1 to 99 of SEQ ID NO: 18 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Variant: The term "variant" means a polypeptide having phospholipase C activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Nucleic Acid Sequences and Amino Acid Sequences

SEQ ID NO: 1: PI-specific PLC, *Pseudomonas* sp.; coding sequence.
SEQ ID NO: 2: PI-specific PLC, *Pseudomonas* sp.; amino acid sequence.
SEQ ID NO: 3: PI-specific PLC, *Pseudomonas* sp.; amino acid sequence of mature polypeptide with N-terminal Alanine.
SEQ ID NO: 4: PI-specific PLC, *Pseudomonas chlorapsis*; coding sequence.
SEQ ID NO: 5: PI-specific PLC, *Pseudomonas chlorapsis*; amino acid sequence.
SEQ ID NO: 6: PI-specific PLC, *Pseudomonas chlorapsis*; amino acid sequence of mature polypeptide with N-terminal Alanine.
SEQ ID NO: 7: PI-specific PLC, *Pseudomonas* sp.; coding sequence.
SEQ ID NO: 8: PI-specific PLC, *Pseudomonas* sp.; amino acid sequence.
SEQ ID NO: 9: PI-specific PLC, *Pseudomonas* sp.; amino acid sequence of mature polypeptide with N-terminal Alanine.
SEQ ID NO: 10: PI-specific PLC, *Pseudomonas chlorapsis*; coding sequence.
SEQ ID NO: 11: PI-specific PLC, *Pseudomonas chlorapsis*; amino acid sequence.
SEQ ID NO: 12: PI-specific PLC, *Pseudomonas chlorapsis*; amino acid sequence of mature polypeptide with N-terminal Alanine.
SEQ ID NO: 13: PI-specific PLC, *Pseudomonas protegens*; coding sequence.
SEQ ID NO: 14: PI-specific PLC, *Pseudomonas protegens*; amino acid sequence.
SEQ ID NO: 15: PI-specific PLC, *Pseudomonas protegens*; amino acid sequence of mature polypeptide with N-terminal Alanine.

SEQ ID NO: 16: PI-specific PLC, *Pseudomonas protegens*; coding sequence.
SEQ ID NO: 17: PI-specific PLC, *Pseudomonas protegens*; amino acid sequence.
SEQ ID NO: 18: PC/PE-specific PLC, *Bacillus* sp. coding sequence.
SEQ ID NO: 19: PC/PE-specific PLC, *Bacillus* sp. amino acid sequence.
SEQ ID NO: 20: PC/PE-specific PLC, *Bacillus* sp. amino acid sequence of mature polypeptide with N-terminal Alanine.
SEQ ID NO: 21: Bt-PLC *Bacillus thuringiensis*; coding sequence.
SEQ ID NO: 22: Bt-PLC *Bacillus thuringiensis*; amino acid sequence of mature polypeptide.
SEQ ID NO: 23: PC/PE-specific PLC, *Bacillus pseudomycoides*; coding sequence.
SEQ ID NO: 24: PC/PE-specific PLC, *Bacillus pseudomycoides*; amino acid sequence.
SEQ ID NO: 25: PC/PE-specific PLC, *Bacillus pseudomycoides*; amino acid sequence with N-terminal Alanine.
SEQ ID NO: 26: PC/PE-specific PLC, *Bacillus mycoides*; coding sequence.
SEQ ID NO: 27: PC/PE-specific PLC, *Bacillus mycoides*; amino acid sequence.
SEQ ID NO: 28: PC/PE-specific PLC, *Listeria innocua*; coding sequence.
SEQ ID NO: 29: PC/PE-specific PLC, *Listeria innocua*; amino acid sequence.
SEQ ID NO: 30: PC/PE-specific PLC, *Listeria innocua*; amino acid sequence with N-terminal Alanine.
SEQ ID NO: 31: SEQ ID NO: 3 of WO 2011/046812.
SEQ ID NO: 32: SEQ ID NO: 4 of WO 2011/046812.
SEQ ID NO: 33: Heterologous signal peptide
SEQ ID NO: 34: PI-specific PLC, *Amycolatopsis azurea*; coding sequence
SEQ ID NO: 35: PI-specific PLC, *Amycolatopsis azurea*; amino acid sequence
SEQ ID NO: 36: PI-specific PLC, *Amycolatopsis azurea*; amino acid sequence with N-terminal Alanine.
SEQ ID NO: 37: PC/PE-specific PLC, *Bacillus macauensis*; coding sequence
SEQ ID NO: 38: PC/PE-specific PLC, *Bacillus macauensis*; amino acid sequence.

DETAILED DESCRIPTION OF THE INVENTION

The present invention relates to phospholipase C enzymes obtained from various strains belonging to the genus *pseudomonas* which is a non-pathogenic (class 1) organism and therefore generally considered safe to work with in the laboratory. The phospholipase C enzymes derived from *pseudomonas* strains all showed specificity towards PI.

The present invention also relates PC, PE-specific phospholipase C enzymes which either are novel or which have never been expressed and characterized. The use of the PC, PE-specific phospholipase C, PurifinePLC, in degumming is known, it is however still relevant to identify additional PC, PE-specific phospholipase C enzymes which perform well in degumming. In a preferred embodiment the PC, PE-specific phospholipases are obtained from strains belonging to the genus of *Bacillus* or *Listeria*.

The present invention furthermore relates to a method for reducing the content of phospholipids in an oil composition using one or more bacterial phospholipase C enzymes. In particular when a PI-specific phospholipase C enzyme is combined with a PC, PE-specific phospholipase C enzyme a beneficial effect is observed in relation to the removal of phospholipids from an oil composition.

Polypeptides Having Phospholipase C Activity

An aspect of the present invention relates to a polypeptide having phosphatidylinositol phospholipase C activity selected from the group consisting of: a) a polypeptide having at least 91% sequence identity to the mature polypeptide of SEQ ID NO: 2; b) a polypeptide encoded by a polynucleotide that hybridizes under medium stringency conditions with i) the mature polypeptide coding sequence of SEQ ID NO: 1, or ii) the full-length complement of (i); c) a polypeptide encoded by a polynucleotide having at least 90% sequence identity to the mature polypeptide coding sequence of SEQ ID NO: 1; d) a variant of the mature polypeptide of SEQ ID NO: 2 comprising a substitution, deletion, and/or insertion at one or more positions; and e) a fragment of the polypeptide of (a), (b), (c), or (d) that has phosphatidylinositol phospholipase C activity.

In one embodiment, the present invention relates to a polypeptide having a sequence identity to the mature polypeptide of SEQ ID NO: 2 of at least 91%, at least 92%, at least 93%, at least 94%, at least 95%, at least 96%, at least 97%, at least 98%, at least 99%, or 100%, which has specificity towards phosphatidyl inositol. In one aspect, the polypeptides differ by up to 10 amino acids, e.g., 1, 2, 3, 4, 5, 6, 7, 8, 9, or 10, from the mature polypeptide of SEQ ID NO: 2. In a preferred embodiment the mature polypeptide of SEQ ID NO: 2 corresponds to amino acids 26 to 322 of SEQ ID NO: 2.

In an embodiment, the polypeptide has been isolated. A polypeptide of the present invention preferably comprises or consists of the amino acid sequence of SEQ ID NO: 2 or an allelic variant thereof; or is a fragment thereof having phosphatidyl inositol phospholipase C activity. In another aspect, the polypeptide comprises or consists of the mature polypeptide of SEQ ID NO: 2. In another aspect, the polypeptide comprises or consists of amino acids 26 to 322 of SEQ ID NO: 2 or to amino acids 1 to 298 of SEQ ID NO: 3.

In particular, the polypeptide may have a length of 280-320 amino acid residues, such as a length of 280-310 amino acid residues, 280-305 amino acid residues, 280-300 amino acid residues, 280-298 amino acid residues, 280-297 amino acid residues, 280-296 amino acid residues, 285-320 amino acid residues, 285-315 amino acid residues, 285-310 amino acid residues, 285-305 amino acid residues, 285-300 amino acid residues, 285-298 amino acid residues, 285-297 amino acid residues, 285-296 amino acid residues, 290-320 amino acid residues, 290-315 amino acid residues, 290-310 amino acid residues, 290-305 amino acid residues, 290-300 amino acid residues, 290-298 amino acid residues, 290-297 amino acid residues, 290-296 amino acid residues, 295-320 amino acid residues, 295-315 amino acid residues, 295-310 amino acid residues, 295-305 amino acid residues, 295-300 amino acid residues, 295-298 amino acid residues, 255-297 amino acid residues, or a length of 295-296 amino acid residues.

In a preferred embodiment, the phosphatidylinositol phospholipase C of the invention is capable of reducing the PI content in a crude oil by at least 30% when applied in 10 mg Enzyme Protein/kg oil at the optimal pH of the polypeptide, more preferred at least 35%, 40%, 45%, 50%, 55%, 60%, 65%, 70%, 75%, 80%, 85%, 90%, 95%, 99% or 100%. In a further embodiment the optimal pH range of the polypeptide of the present invention is between 4.5 to 8.5, more preferred from 5.0 to 8.0, even more preferred from 6.5 to 7.5.

According to some embodiments, the phosphatidylinositol phospholipase C of the invention has a thermal denaturation temperature of at least 60° C., such as 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C. or at least 90° C. as determined by Differential Scanning calorimetry (DSC).

The denaturation temperature may in particular be determined as the top of denaturation peak (major endothermic peak) in thermograms (Cp vs. T) obtained after heating a 1 mg/ml solution of the polypeptide in buffer (50 mM Na-acetate pH 5.5, or 50 mM Hepes pH 7) at a constant programmed heating rate of 200 K/hr.

According to some embodiments, the phosphatidylinositol phospholipase C of the invention may be able to reduce the phosphatidylinositol content of crude soy bean oil by 50% or more, 50%, such as by 55%, by 60%, by 65%, by 70%, by 75%, by 80%, by 85%, by 90% or by 95% or more, the reduction in phosphatidylinositol content being determined by $^{31}$P-NMR after addition of 100 mg enzyme protein (EP)/kg oil and incubation of the oil and enzyme at 50° C. for 2 hours at pH 5.5.

Preferably, the phosphatidylinositol phospholipase C of the invention is able to reduce the phosphorous content of crude soy bean oil to 20 mg/kg oil or less as determined by Inductively coupled plasma optical emission spectrometry (ICP-OES) after incubation of 4 mg enzyme protein/kg oil in a low aqueous system comprising 3% water based on oil amount at 50-60° C. for 5 hours.

For the purpose of determining the ability of the polypeptide to reduce phosphorous, the crude soy oil comprising 80-140 ppm phosphorous present as phosphatidic acid (PA), 140-200 ppm phosphorous present as phosphatidyl ethanolamine (PE), 70-110 ppm phosphorous present as phosphatidic acid (PI) and 130-200 ppm phosphorous present as phosphatidyl choline may be used; the phosphorous content being measured by $^{31}$P-NMR.

In further embodiments, the phosphatidylinositol phospholipase C of the invention is robust towards varying pH conditions and shows good performance in water degumming (no acid/base) as well as acid assisted degumming followed by base neutralization with varying concentrations of NaOH (e.g., Acid/base pretreatment by addition of Ortho Phosphoric acid in amounts equal to 0.05% (100% pure Ortho Phosphoric acid) based on oil amount followed by base neutralization with 0.5 eqv, 1.0 eqv or 1.5 eqv NaOH).

Further, the reduction of phosphorous content may be obtained in an oil degumming process comprising the steps of:

i) Optionally treating crude soy bean oil with acid/base by adding an 85% solution of Ortho Phosphoric acid in amounts corresponding to 0.05% (100% pure Ortho Phosphoric acid) based on oil amount, mixing in ultrasonic bath for 5 minutes, followed by incubation in rotator for 15 minutes and base neutralization with 4 M NaOH applied in equivalents (from 0.5 to 0.15) to pure Ortho Phosphoric acid in ultrasonic bath for 5 minutes;

ii) Adding the polypeptide to the oil in amounts of 4 mg enzyme protein/kg oil in a low aqueous system comprising 3% water based on oil amount and subjecting the oil and the polypeptide to ultrasonic treatment for 5 minutes;

iii) Incubating the polypeptide and oil at 50-60° C. for 5 hours with stirring at 20 rpm;

iv) Centrifuging the oil and the polypeptide at 700 g at 85° C. for 15 minutes.

Homologues of PI-specific phospholipase C of the present invention have been identified from sequences annotated in genome sequencing projects. When aligned to the mature sequence of SEQ ID NO: 2 the identities are as follows:

| | |
|---|---|
| SEQ ID NO: 2 mature | 100.00 |
| J2E6B1 (SEQ ID NO: 5) | 83.11 |
| J3EBR2 (SEQ ID NO: 8) | 82.78 |
| I4Y4N5 (SEQ ID NO: 11) | 82.45 |
| Q4K3U9 (SEQ ID NO: 14) | 90.07 |
| R4RTF9 (SEQ ID NO: 17) | 90.73 |
| M2NSV3 (SEQ ID NO: 35) | 20.00 |

To our knowledge none of these homologues have ever been expressed and characterized and their use in degumming or any other application has never been described. For the purpose of generating nucleic acid constructs, expression vectors, and host cells as well as compositions and methods of use the PI-specific phospholipase C of SEQ ID NO: 2 as well as the homologues of SEQ ID NO: 5, SEQ ID NO: 8, SEQ ID NO: 11, SEQ ID NO: 14 and SEQ ID NO: 17 are PI-specific phospholipase C polypeptides of the present invention and the polynucleotides encoding them are polynucleotides of the present invention.

In another embodiment, the present invention relates to a polypeptide having PI-specific phospholipase C activity encoded by a polynucleotide that hybridizes under medium stringency conditions, medium-high stringency conditions, high stringency conditions, or very high stringency conditions with (i) the mature polypeptide coding sequence of SEQ ID NO: 1 or (ii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

The polynucleotides of SEQ ID NO: 1, 4, 7, 10, 13 or 16 or a subsequence thereof, as well as the polypeptide of SEQ ID NO: 2, 5, 8, 11, 14 or 17 or a fragment thereof may be used to design nucleic acid probes to identify and clone DNA encoding polypeptides having PI-specific phospholipase C activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having PI-specific phospholipase C activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under medium to very high stringency conditions. Molecules to which the nucleic acid probe hybridizes under these conditions can be detected using, for example, X-ray film or any other detection means known in the art.

In another embodiment, the present invention relates to a polypeptide having PI-specific phospholipase C activity encoded by a polynucleotide having a sequence identity to the mature polypeptide coding sequence of SEQ ID NO: 1 at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 2 comprising a substitution, deletion, and/or insertion at one or more (e.g., several) positions. A specific variant of SEQ ID NO: 2 is disclosed as SEQ ID NO: 3 containing an A inserted in front of the Q in position 26 of SEQ ID NO: 2. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Another aspect of the present invention relates to a polypeptide having PC and PE-specific phospholipase C activity, selected from the group consisting of: a) a polypeptide having at least 70% sequence identity to the mature polypeptide of SEQ ID NO: 19; b) a polypeptide encoded by a polynucleotide that hybridizes under low stringency conditions with i) the mature polypeptide coding sequence of SEQ ID NO: 18, or ii) the full-length complement of (i); c) a polypeptide encoded by a polynucleotide having at least 70% sequence identity to the mature polypeptide coding sequence of SEQ ID NO: 18; d) a variant of the mature polypeptide of SEQ ID NO: 19 comprising a substitution, deletion, and/or insertion at one or more positions; and e) a fragment of the polypeptide of (a), (b), (c), or (d) that has PC and PE specific phospholipase C activity.

In one embodiment, the present invention relates to polypeptides having a sequence identity to the mature polypeptide of SEQ ID NO: 19 of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have PC and PE-specific phospholipase C activity. In one aspect, the polypeptides differ by up to 10 amino acids, e.g., 1, 2, 3, 4, 5, 6, 7, 8, 9, or 10, from the mature polypeptide of SEQ ID NO: 19.

In an embodiment, the polypeptide has been isolated. A polypeptide of the present invention preferably comprises or consists of the amino acid sequence of SEQ ID NO: 19 or an allelic variant thereof; or is a fragment thereof having phospholipase C activity. In another aspect, the polypeptide comprises or consists of the mature polypeptide of SEQ ID NO: 19. In another aspect, the polypeptide comprises or consists of amino acids 34 to 278 of SEQ ID NO: 19 or amino acid residues 1-246 of SEQ ID NO: 20.

In further embodiments, the polypeptide has a length of 220-280 amino acid residues, such as a length of 220-270 amino acid residues, 220-260 amino acid residues, 220-250 amino acid residues, 220-248 amino acid residues, 220-246 amino acid residues, 220-244 amino acid residues, 225-280 amino acid residues, 225-270 amino acid residues, 225-260 amino acid residues, 225-250 amino acid residues, 225-248 amino acid residues, 225-246 amino acid residues, 225-244 amino acid residues, 230-280 amino acid residues, 230-270 amino acid residues, 230-260 amino acid residues, 230-250 amino acid residues, 230-248 amino acid residues, 230-246 amino acid residues, 230-244 amino acid residues, 235-280 amino acid residues, 235-270 amino acid residues, 235-260 amino acid residues, 235-250 amino acid residues, 235-248 amino acid residues, 235-246 amino acid residues, 235-244 amino acid residues, 240-280 amino acid residues, 240-270 amino acid residues, 240-260 amino acid residues, 240-250 amino acid residues, 240-248 amino acid residues, 240-246 amino acid residues, 240-244 amino acid residues, 242-280 amino acid residues, 242-270 amino acid residues, 242-260 amino acid residues, 242-250 amino acid residues, 242-248 amino acid residues, 242-246 amino acid residues, 242-244 amino acid residues, 243-280 amino acid residues, 243-270 amino acid residues, 243-260 amino acid residues, 243-250 amino acid residues, 243-248 amino acid residues, 243-246 amino acid residues, 243-244 amino acid residues.

The polypeptide having PC and PE-specific phospholipase C activity may in particular have a thermal denaturation temperature of at least 60° C., such as 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C. or at least 90° C. as determined by Differential Scanning calorimetry (DSC).

The said denaturation temperature may be determined as the top of denaturation peak (major endothermic peak) in thermograms (Cp vs. T) obtained after heating a 1 mg/ml solution of the polypeptide in buffer (50 mM Na-acetate pH 5.5, or 50 mM Hepes pH 7) at a constant programmed heating rate of 200 K/hr.

In a preferred embodiment, the PC and PE-specific phospholipase C of the invention is capable of reducing the PC and PE content in a crude oil. Preferably, the polypeptide of the invention is capable of reducing the PC and PE content in a crude oil by at least 30% each when applied in 10 mg Enzyme Protein/kg oil at the optimal pH of the polypeptide, more preferred at least 35%, 40%, 45%, 50%, 55%, 60%, 65%, 70%, 75%, 80%, 85%, 90%, 95%, 99% or 100%. In a further embodiment the optimal pH range of polypeptide of the present invention is between 5.0 to 8.5, more preferred from 5.5 to 8.0, even more preferred from 6.0 to 7.5. In further embodiments the polypeptide having PC and PE-specific phospholipase C activity is able to reduce the phosphatidyl ethanolamine and/or phosphatidyl choline content of crude soy bean oil by 50% or more, 50%, such as by 55%, by 60%, by 65%, by 70%, by 75%, by 80%, by 85%, by 90% or by 95% or more, the reduction in phosphatidyl ethanolamine and/or phosphatidyl choline content being determined by $^{31}$P-NMR after addition of 100 mg enzyme protein (EP)/kg oil and incubation of the oil and enzyme at 50° C. for 2 hours at pH 5.5.

In still further embodiments, the polypeptide having PC and PE-specific phospholipase C activity is able to reduce the phosphorous content of crude soy bean oil to 20 mg/kg oil or less as determined by Inductively coupled plasma optical emission spectrometry (ICP-OES) after incubation of 4 mg enzyme protein/kg oil in a low aqueous system comprising 3% water based on oil amount at 50-60° C. for 5 hours.

The ability of the polypeptide to reduce phosphorous content may in particular be determined using a crude soy oil which comprises 80-140 ppm phosphorous present as phosphatidic acid (PA), 140-200 ppm phosphorous present as phosphatidyl ethanolamine (PE), 70-110 ppm phosphorous present as phosphatidic acid (PI) and 130-200 ppm phosphorous present as phosphatidyl choline; the phosphorous content being measured by $^{31}$P-NMR.

In particular, the reduction of phosphorous content and/or reduction in phosphatidyl ethanolamine and/or phosphatidyl choline content may be obtained in an oil degumming process comprising the steps of:
i) Optionally treating crude soy bean oil with acid/base by adding an 85% solution of Ortho Phosphoric acid in amounts corresponding to 0.05% (100% pure Ortho Phosphoric acid) based on oil amount, mixing in ultrasonic bath for 5 minutes, followed by incubation in rotator for 15 minutes and base neutralization with 4 M NaOH applied in equivalents (from 0.5 to 0.15) to pure Ortho Phosphoric acid in ultrasonic bath for 5 minutes;
ii) Adding the polypeptide to the oil in amounts of 4 mg enzyme protein/kg oil in a low aqueous system comprising 3% water based on oil amount and subjecting the oil and the polypeptide to ultrasonic treatment for 5 minutes;
iii) Incubating the polypeptide and oil at 50-60° C. for 5 hours with stirring at 20 rpm;
iv) Centrifuging the oil and the polypeptide at 700 g at 85° C. for 15 minutes.

The closest related sequence to the PC, PE-specific PLC of the present invention is SEQ ID NO: 4 from WO2011/046812 (SEQ ID NO: 32 in this application) with 44.6% identity to the mature sequence of SEQ ID NO: 19 (amino acids 34 to 278). This as well as the following PC, PE-specific PLC's identified by UniProt number may be useful in the method of the present invention In another embodiment, the present invention relates to a polypeptide having PC and PE-specific phospholipase C activity encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 18 or (ii) the full-length complement of (i) or (ii) (Sambrook et al., 1989, *Molecular Cloning, A Laboratory Manual*, 2d edition, Cold Spring Harbor, New York). In an embodiment, the polypeptide has been isolated.

The polynucleotide of SEQ ID NO: 18 or a subsequence thereof, as well as the polypeptide of SEQ ID NO: 19 or a fragment thereof may be used to design nucleic acid probes to identify and clone DNA encoding polypeptides having phospholipase C activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having PC and PE-specific phospholipase C activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 18 or a subsequence thereof, the carrier material is used in a Southern blot.

| | | | | | | |
|---|---|---|---|---|---|---|
| SEQ ID NO: 19 mature | 100.00 | 44.63 | 43.57 | 43.80 | 43.80 | 31.65 |
| SEQ ID NO: 32 | 44.63 | 100.00 | 80.14 | 80.50 | 80.50 | 40.23 |
| C3HDV6 (SEQ ID NO: 22) | 43.57 | 80.14 | 100.00 | 88.69 | 88.34 | 40.44 |
| P34B3F (SEQ ID NO: 24) | 43.80 | 80.50 | 88.69 | 100.00 | 98.59 | 39.05 |
| C3AHL7 (SEQ ID NO: 27) | 43.80 | 80.50 | 88.34 | 98.59 | 100.00 | 39.05 |
| E3Z3X0 (SEQ ID NO: 29) | 31.65 | 40.23 | 40.44 | 39.05 | 39.05 | 100.00 |
| I8AFV4 (SEQ ID NO: 38) | 42.08 | | | | | |

The mature sequence of SEQ ID NO: 22, corresponding to amino acids 39 to 283 has also been disclosed in relation to degumming as SEQ ID NO: 5 in EP 1788080. To our knowledge none of the PC, PE-specific PLC's of SEQ ID NO: 24, 27 or 29 have ever been expressed and characterized and their use in degumming or any other application has never been described. For the purpose of generating nucleic acid constructs, expression vectors, and host cells as well as compositions and methods of use the PC, PE-specific phospholipase C of SEQ ID NO: 19 as well as the homologues of SEQ ID NO: 24, SEQ ID NO: 27 and SEQ ID NO: 29 are PC, PE-specific phospholipase C polypeptides of the present invention and the polynucleotides encoding them are polynucleotides of the present invention.

For purposes of the present invention, hybridization indicates that the polynucleotide hybridizes to a labeled nucleic acid probe corresponding to (i) SEQ ID NO: 18; (ii) the mature polypeptide coding sequence of SEQ ID NO: 18; (iii) the full-length complement thereof; or (iv) a subsequence thereof; under low to very high stringency conditions. Molecules to which the nucleic acid probe hybridizes under these conditions can be detected using, for example, X-ray film or any other detection means known in the art.

In another embodiment, the present invention relates to a polypeptide having PC and PE-specific phospholipase C activity encoded by a polynucleotide having a sequence identity to the mature polypeptide coding sequence of SEQ ID NO: 18 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 19 comprising a substitution, deletion, and/or insertion at one or more (e.g., several) positions. A specific variant of SEQ ID NO: 19 is disclosed as SEQ ID NO: 20 containing an A inserted in front of the W in position 34 of SEQ ID NO: 19. In an embodiment, the number of amino acid substitutions, deletions and/or insertions introduced into the mature polypeptide of SEQ ID NO: 19 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

In relation to the polypeptides of the present invention examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Other possible approaches to generating variants having similar or substantially similar physic-chemical or functional properties as the PI-specific phospholipase C of SEQ ID NO: 2 (the mature polypeptide of SEQ ID NO: 2) or the PC PE-specific phospholipase C of SEQ ID NO: 19 (the mature polypeptide of SEQ ID NO: 19) would include introducing changes in the amino acid sequence within regions showing medium to high variability, identified by aligning the respective polypeptide with related sequences. In the PI-specific phospholipase C of SEQ ID NO: 2, such regions may be identified by alignment to best possible fit with the amino acid sequences of SEQ ID NOs: 8, (UniProtKB/TrEMBL: J3EBR2), 11 (UniProtKB/TrEMBL: 14Y4N5), 14 (UniProtKB/TrEMBL: Q4K3U9) and 17 (UniProtKB/TrEMBL: R4RTF9).

By such alignment the following regions having medium or high variability may be identified in SEQ ID NO: 2 (using the amino acids numbering of SEQ ID NO: 2):

| | |
|---|---|
| Amino acids 28-43 | High variability |
| Amino acid 59 | High variability |
| Amino acids 82-88 | High variability |
| Amino acids 130-131 | High variability |
| Amino acid 165 | High variability |
| Amino acids 254-255 | High variability |
| Amino acid 266 | High variability |

-continued

| | |
|---|---|
| Amino acids 298-301 | High variability |
| Amino acids 311-314 | High variability |

Hence, in some embodiments of the invention a polypeptide having a sequence identity to the mature polypeptide of SEQ ID NO: 2 of at least 91%, at least 92%, at least 93%, at least 94%, at least 95%, at least 96%, at least 97%, at least 98%, at least 99%, or 100%, which has specificity towards phosphatidyl inositol, wherein one or more amino acids residues have been substituted, deleted or added in one or more of the regions defined by amino acids 28-43, amino acid 59, amino acids 82-88, amino acids 130-131, amino acid 266, amino acids 298-301, amino acids 311314, using the amino acids numbering in SEQ ID NO: 2.

In further embodiments, these polypeptides differ by up to 10 amino acids, e.g., 1, 2, 3, 4, 5, 6, 7, 8, 9, or 10, from the mature polypeptide of SEQ ID NO: 2.

In corresponding embodiments relating to the PE/PC-specific phospholipase C of SEQ ID NO: 19, such regions may be identified by alignment to best possible fit with the amino acid sequences of SEQ ID NOs: 22, (UniProtKB/TrEMBL:C3HDV6), 24 (UniProtKB/TrEMBL:C3BG10), 27 (UniProtKB/TrEMBL:C3AHL7) and 29 (UniProtKB/TrEMBL: E3Z3x0).

By such alignment the following regions having medium or high variability may be identified in SEQ ID NO: 19 (using the amino acid numbering of SEQ ID NO: 19):

| | |
|---|---|
| Amino acids 3-72 | High variability |
| Amino acids 74-123 | Medium variability |
| Amino acids 129-142 | High variability |
| Amino acids 145-147 | Medium variability |
| Amino acids 154-155 | Medium variability |
| Amino acids 164-189 | High variability |
| Amino acids 188-201 | High variability |
| Amino acids 203-226 | Medium variability |
| Amino acids 228-237 | High variability |
| Amino acids 244-246 | Medium variability |
| Amino acids 248-258 | Medium variability |
| Amino acids 260-278 | Medium variability |

In one embodiment, the present invention relates to polypeptides having a sequence identity to the mature polypeptide of SEQ ID NO: 19 of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have PC and PE-specific phospholipase C activity, wherein one or more amino acids residues, such as up to 10 amino acids, e.g., 1, 2, 3, 4, 5, 6, 7, 8, 9, or 10, have been substituted, deleted or added in one or more of the regions defined by amino acids 3-72, amino acids 74-123, amino acids 129-142, amino acids 145-147, amino acids 154-155, amino acids 164-189, amino acids 188-201, amino acids 203-226, amino acids 228-237, amino acids 244-246, amino acids 248-258, amino acids 260-278, using the amino acid numbering in SEQ ID NO: 19.

In further embodiments, these polypeptides differ by up to 10 amino acids, e.g., 1, 2, 3, 4, 5, 6, 7, 8, 9, or 10, from the mature polypeptide of SEQ ID NO: 19.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for the desired phospholipase C activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Essential amino acids in the sequence of amino acids 26 to 322 of SEQ ID NO: 2 are predicted to be located at positions H50, N51, and D74. These amino acids are believed to be involved in coordinating the calcium in the active site. The prediction is supported by the following article Iwasaki et al., 1998, *Biochimica et Biophysica Acta* 1391: 52-66 that show that when the H corresponding to H50 in SEQ ID NO: 2 is changed the PLC identified as UniProt B3A043 or PDB 3H4X dies. In a preferred embodiment a polypeptide of the invention maintains the amino acids corresponding to position 50, 51 and 74 when aligned to SEQ ID NO: 2.

Essential amino acids in the sequence of amino acids 34 to 278 of SEQ ID NO: 19 are predicted to be located at positions W34, H47, D88, H102, H152, D156, H162, H177 and E181. These amino acids are believed to be involved in coordinating the three Zn ions need for the catalytic activity based on a homology model of the sequence. In a preferred embodiment a polypeptide of the invention maintains the amino acids corresponding to positions 34, 47, 88, 102, 152, 156, 162, 177 and 181 when aligned to SEQ ID NO: 19.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Sources of Polypeptides Having Phospholipase C Activity

A polypeptide having phospholipase C activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a Gram-positive bacterial polypeptide such as a *Bacillus*, *Listeria* or *Pseudomonas* polypeptide.

In one aspect, the polypeptide is a *Bacillus alkalophilus*, *Bacillus amyloliquefaciens*, *Bacillus brevis*, *Bacillus cereus*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pseudomycoides*, *Bacillus pumilus*, *Bacillus stearothermophilus*, *Bacillus subtilis*, or *Bacillus thuringiensis* polypeptide.

In another aspect, the polypeptide is a *Listeria innocua* polypeptide.

In another aspect, the polypeptide is a *Pseudomonas chlororaphis* or *Pseudomonas protegens* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus* or *Pseudomonas*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or SEQ ID NO: 18, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in an expression host. Preferably the expression is done in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art. In a preferred embodiment the polynucleotide encodes an alanine in front of the sequence encoding a mature a phospholipase C. In a further embodiment the mature phospholipase C contain an N-terminal sequence starting with the amino acids WSA, and the polypeptide expressed from the polynucleotide will result in an N-terminal sequence starting with amino acids AWSA.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylllA gene (Agaisse and Lereclus, 1994, *Molecular Microbiology* 13: 97-107), *E. coli* lac operon, *E. coli* trc promoter (Egon et al., 1988, Gene 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* crylllA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. Other examples of regulatory sequences are those that allow for gene amplification.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. Preferably the polynucleotide is heterologous, meaning that it does not exist naturally in the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote. In a preferred embodiment the host cell is a recombinant host cell which does not exist in nature.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

Methods of Production

Based on the nucleotide sequence identified as SEQ ID NO: 1, SEQ ID NO: 4, SEQ ID NO: 7, SEQ ID NO: 10, SEQ ID NO: 13, SEQ ID NO: 16, SEQ ID NO: 18, SEQ ID NO: 21, SEQ ID NO: 23, SEQ ID NO: 26, SEQ ID NO: 28 or SEQ ID NO: 31 a synthetic gene can be obtained from a number of vendors such as Gene Art (GENEART AG BioPark, Josef-Engert-Str. 11, 93053, Regensburg, Germany) or DNA 2.0 (DNA2.0, 1430 O'Brien Drive, Suite E, Menlo Park, CA 94025, USA). The synthetic gene can be designed to incorporate additional DNA sequences such as restriction sites or homologous recombination regions to facilitate cloning into an expression vector as described above and expressed in a host cell as described above, for example in *Bacillus subtilis*.

An aspect of the present invention relates to a method of producing a phospholipase C polypeptide in a bacterial host, in particular, a *Bacillus* host, more specifically a *Bacillus subtilis* or *Bacillus licheniformis* host, wherein the phospholipase C coding sequence encode an alanine in front of the predicted N-terminal amino acid of the phospholipase C polypeptide. Preferably the phospholipase C is a PC and PE-specific phospholipase C polypeptide. This will result in a mature phospholipase C polypeptide with an N-terminal alanine as exemplified in SEQ ID NO: 20 and SEQ ID NO: 30. Preferably the wild type mature sequence of the phospholipase C has an N-terminal sequences starting with WSA. Without being bound by theory the inventors believe that this extra alanine protect the N-terminal sequence of the mature phospholipase C sequence, e.g., amino acids WSA, from protease activity in the host cell.

The present invention also relates to methods of producing a phosphatidylinositol phospholipase C polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Pseudomonas* cell.

The present invention also relates to methods of producing a PC and PE-specific phospholipase C polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Bacillus* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide with phospholipase C activity may be detected using methods known in the art, see the "Assay for phospholipase activity" section below. These detection methods include, but are not limited to, use of specific antibodies, formation of an enzyme product, or disappearance of an enzyme substrate, e.g., P-NMR assay described in example 5 or liquid chromatography coupled to triple quadrupole mass spectrometer (LC/MS/MS) as described in Example 7 or lecithin plate assays.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Assays for Phospholipase Activity

The invention provides isolated, synthetic or recombinant polypeptides (e.g., enzymes, antibodies) having a phospholipase activity, or any combination of phospholipase activities, and nucleic acids encoding them. Any of the many phospholipase activity assays known in the art can be used to determine if a polypeptide has a phospholipase activity and is within the scope of the invention. Routine protocols for determining phospholipase A, B, D and C, are well known in the art.

Exemplary activity assays include turbidity assays, methylumbelliferyl phosphocholine (fluorescent) assays, Amplex red (fluorescent) phospholipase assays, thin layer chromatography assays (TLC), cytolytic assays and p-nitrophenylphosphorylcholine assays.

Using these assays polypeptides, peptides or antibodies can be quickly screened for a phospholipase activity.

Plate assays with a substrate containing agar can be used to determine phospholipase activity Plate assay. The assay can be conducted as follows. Plates are casted by mixing of 5 ml 2% Agarose (Litex HSA 1000) prepared by mixing and cooking in buffers (100 mM HEPES and 100 mM Citrate with pH adjusted from pH 3.0 to pH 7.0) for 5 minutes followed by cooling to approximately 60° C. and 5 ml substrate (L-α-phosphatidylcholine, 95% from Soy (Avanti 441601) or L-α-phosphatidylinositol from Soy (Avanti 840044P) for PI-specificity or L-α-phosphatidylethanolamine from Soy (Avanti 840024P) dispersed in water (MilliQ) at 60° C. for 1 minute with Ultra Turrax for PC-specificity) gently mixed into petri dishes with diameter of 7 cm and cooled to room temperature before holes with a diameter of approximately 3 mm were punched by vacuum. Ten microliters of purified enzyme diluted to 0.4 mg/ml is added into each well before plates were sealed by parafilm and placed in an incubator at 55° C. for 48 hours. Plates were taken out for photography at regular intervals.

Turbidity assays to determine phospholipase activity are described, e.g., in Kauffmann, 2001, "Conversion of *Bacillus thermocatenulatus* lipase into an efficient phospholipase with increased activity towards long-chain fatty acyl substrates by directed evolution and rational design," *Protein Engineering* 14:919-928; Ibrahim, 1995, "Evidence implicating phospholipase as a virulence factor of *Candida albicans*," *Infect. Immun.* 63:1993-1998.

Methylumbelliferyl (fluorescent) phosphocholine assays to determine phospholipase activity are described, e.g., in Goode, 1997, "Evidence for cell surface internal phospholipase activity in ascidian eggs," *Develop. Growth Differ.* 39:655-660; Diaz, 1999, "Direct fluorescence-based lipase activity assay," *Bio Techniques* 27:696-700.

Amplex Red (fluorescent) Phospholipase Assays to determine phospholipase activity are available as kits, e.g., the detection of phosphatidylcholine-specific phospholipase using an Amplex Red phosphatidylcholine-specific phospholipase assay kit from Molecular Probes Inc. (Eugene, OR), according to manufacturer's instructions.

Fluorescence is measured in a fluorescence microplate reader using excitation at 560±10 nm and fluorescence detection at 590±10 nm. The assay is sensitive at very low enzyme concentrations.

Thin layer chromatography assays (TLC) to determine phospholipase activity are described, e.g., in Reynolds, 1991, *Methods in Enzymol.* 197:3-13; Taguchi, 1975, "Phospholipase from *Clostridium novyi* type A.I," *Biochim. Biophys. Acta* 409:75-85. Thin layer chromatography (TLC) is a widely used technique for detection of phospholipase activity. Various modifications of this method have been used to extract the phospholipids from the aqueous assay mixtures. In some PLC assays the hydrolysis is stopped by addition of chloroform/methanol (2:1) to the reaction mixture. The unreacted starting material and the diacylglycerol are extracted into the organic phase and may be fractionated by TLC, while the head group product remains in the aqueous phase. For more precise measurement of the phospholipid digestion, radio labeled substrates can be used (see, e.g., Reynolds, 1991, *Methods in Enzymol.* 197:3-13). The ratios of products and reactants can be used to calculate the actual number of moles of substrate hydrolyzed per unit time. If all the components are extracted equally, any losses in the extraction will affect all components equally. Separation of phospholipid digestion products can be achieved by silica gel TLC with chloroform/methanol/water (65:25:4) used as a solvent system (see, e.g., Taguchi, 1975, *Biochim. Biophys. Acta* 409:75-85).

p-N itrophenylphosphorylcholine assays to determine phospholipase activity are described, e.g., in Korbsrisate, 1999, *J. Clin. Microbiol.* 37:3742-3745; Berka, 1981, *Infect. Immun.* 34:1071-1074. This assay is based on enzymatic hydrolysis of the substrate analog p-nitrophenylphosphorylcholine to liberate a yellow chromogenic compound p-nitrophenol, detectable at 405 nm. This substrate is convenient for high throughput screening. Similar assays using substrates towards the other phospholipid groups can also be applied, e.g., using p-nitrophenylphosphorylinositol or p-nitrophenylphosphorylethanolamine.

A cytolytic assay can detect phospholipases with cytolytic activity based on lysis of erythrocytes. Toxic phospholipases can interact with eukaryotic cell membranes and hydrolyze phosphatidylcholine and sphingomyelin, leading to cell lysis. See, e.g., Titball, 1993, *Microbiol. Rev.* 57:347-366.

Further assays like $^{31}$P-NMR and Liquid Chromatography coupled to triple quadrupole mass spectrometer (LC/MS/MS) are described in the example section of this application.

Compositions

The present invention also relates to compositions comprising a PI-specific PLC polypeptide of the present invention, preferably with an additional component. The PI-specific PLC polypeptides of the present invention includes a) a polypeptide comprising an amino acid sequence selected from the group consisting of: i) amino acid residues 26-322 of SEQ ID NO: 2 or amino acid residues 1-298 of SEQ ID NO: 3; ii) amino acid residues 26-323 of SEQ ID NO: 5 or amino acid residues 1-299 of SEQ ID NO: 6; iii) amino acid residues 26-323 of SEQ ID NO: 8 or amino acid residues 1-299 of SEQ ID NO: 9; iv) amino acid residues 26-323 of SEQ ID NO: 11 or amino acid residues 1-296 of SEQ ID NO: 12; v) amino acid residues 26-322 of SEQ ID NO: 14 or amino acid residues 1-298 of SEQ ID NO: 15; vi) amino acid residues 26-322 of SEQ ID NO: 17; and vii) amino acid residues 28-339 of SEQ ID NO: 35; or b) a polypeptide comprising an amino acid sequence which has at least 75% identity to one of the amino acid sequences in a); or c) a functional fragment of a) or b).

The present invention also relates to compositions comprising a PC, PE-specific PLC polypeptide of the present invention, preferably with an additional component.

The present invention also relates to compositions comprising a mixture of a PI-specific PLC of the present invention with one or more, further phospholipase activities selected from PLA1, PLA2, PLC and PLD.

The present invention also relates to a composition comprising a mixture of a phosphatidylinositol phospholipase C from the genus of *Pseudomonas* and a PC and PE-specific phospholipase C polypeptide. A preferred composition of the invention comprises a PI-specific PLC polypeptide of the present invention combined with a PC, PE-specific PLC polypeptide. Preferably the PC and PE-specific PLC is selected from Purifine or a mature polypeptide of SEQ ID NO: 19, 20, 22, 24, 25, 27, 29, 30 32 or 38. The PC and PE-specific PLC may also be selected from a sequence which is at least 80%, 85%, 90%, 95% or 98% identical to a mature polypeptide of SEQ ID NO: 19, 20, 22, 24, 25, 27, 29, 30 32 or 38 which has PC and PE-specificity. In alternative embodiments of the invention the composition comprises a PI-specific PLC polypeptide of the present invention combined with a PLC with specificity towards PA or PC or PE, or PE and PA; or PC and PA; or PC and PE and PA; or any combination thereof.

The phospholipases of the present invention may be formulated with components selected from the group consisting of buffer agents, inorganic salts, solvents, inert solids and mixtures thereof. Appropriate buffer systems, e.g., are made from aqueous solutions of salts or organic acids, amino acids, phosphate, amines or ammonia in concentrations between 0.01 M and 1 M at pH 2 to 10. Preferably, alkali metal salts of citric acid, acetic acid, glycine and/or hydrochlorides of tris(hydroxymethyl)amine and ammonia at 0.1 M to 0.2 M at pH 4 to 8 are used. Preferably, the phospholipase is dissolved in an aqueous buffer solution such as glycine buffer, citric acid buffer, etc. Citrate containing buffers have been found to be very suitable, in particular, sodium citrate buffers, preferably at neutral pH.

The compositions of the invention may comprise phospholipases of the invention immobilized unto a solid support. Solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextranagarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof. Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof. Another type of solid support useful in the present invention is ceramic. Some examples include non-porous ceramic, porous ceramic, Si02, Ah03. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support. Other exemplary solid supports used to practice the invention comprise diatomaceous earth products and silicates. Some examples include CELITE® KENITE®, DIACTIV®, PRIM ISIL® ' DIAFIL® diatomites and MICRO-CEL®' CALFLO®, SILASORB™, and CELKA TE® synthetic calcium and magnesium silicates.

Some examples of methods for immobilizing enzymes include, e.g., electrostatic droplet generation, electrochemical means, via adsorption, via covalent binding, via crosslinking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. 0. Kaplan. Volume 136; and Immobilization of Enzymes and Cells. 1997. Humana Press. Edited by G. F. Bickerstaff. Series: Methods in Biotechnology, Edited by J. M. Walker.

In a further embodiment the composition may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The phospholipases or compositions of the invention may be applied in a process for removing phospholipids from an oil, e.g., a vegetable oil, animal oil or fat, tallow, or grease.

Applications in which the phospholipase of the invention can be used comprise i) degumming of oil, e.g., vegetable oil, or an edible vegetable oil, or in a process comprising hydrolysis of phospholipids in the gum fraction from water degumming to release entrapped triglyceride oil, ii) in a process comprising hydrolysis of phospholipids to obtain improved phospholipid emulsifiers, in particular wherein said phospholipid is lecithin, iii) in a process for improving the filterability of an aqueous solution or slurry of carbohydrate origin which contains phospholipid, iv) in a process for the extraction of oil, v) in a process for the production of an animal feed product, vi) in a process for the production of a biofuel, e.g., a biodiesel, vii) in a process for the production of a detergent product, and/or viii) in a process for making a baked product, comprising adding the phospholipase to a dough, and baking the dough to make the baked product.

The phospholipases of the invention may be applied in a process comprising treatment of a phospholipid or lysophospholipid with the phospholipases or compositions of the invention. The phospholipases or compositions react with the phospholipids or lysophospholipid to form monoglyceride or diglyceride and a phosphate ester or phosphoric acid.

Degumming: The phospholipases of the invention and combinations thereof may be used for degumming oil, e.g., animal oil or fat, tallow, grease or a vegetable oil, i.e., in a process to reduce the phospholipid content in the oil. The degumming process is applicable to the purification of any edible oil which contains phospholipid, e.g., vegetable oil such as soybean oil, rape seed oil, or sunflower oil or any other oil mentioned under the definition of crude oils.

PI-specific PLC converts phosphatidyl inositol (PI) to diglyceride and phosphoinositol. PC-specific PLC converts phosphatidylcholine (PC) to diglyceride and phosphocholine. PE-specific PLC converts phosphatidylethanolamine (PE) to diglyceride and phophoethanolamine. The diglyceride stays in the oil phase (improving oil yield) and the phosphorous-containing moieties separates into the aqueous phase where it is removed as a component of the heavy phase during centrifugation. The gum phase (heavy phase) may be treated further with a phospholipase or composition of the present invention to increase hydrolysis of phospholipids in the gum fraction from water degumming to release entrapped triglyceride oil This is particular useful when de degumming process has not already applied phospholipases. Phospholipases of the invention, e.g., a PI-specific PLC's and/or PC, PE-specific PLC's of the invention, can be incorporated into either water degumming or a chemical or physical oil refining process. In a preferred embodiment the phospholipases of the invention are incorporated into a water degumming process with preferably less than 10%, 9%, 8%, 7%, 6% or 5% water, even more preferably less than 4%, 3% or 2% water, preferably at 50° C. or above, even more preferably at 60° C. or above.

In another preferred embodiment, the phospholipases of the invention are incorporated into a physical refining process applying citric acid or phosphoric acid and sodium hydroxide to facilitate hydratability of insoluble phospholipids and ensure an environment suitable for the enzyme with preferably less than 0.15% citric acid or phosphoric acid, even more preferably less than 0.1%, 0.09%, 0.08%, 0.07%, 0.06% or 0.05%; and less than 4%, 3% or 2% water, preferably at 50° C. or above, even more preferably at 60° C. or above.

In other embodiments, the degumming process is a caustic refining process or acid degumming process.

An aspect of the present invention is a method for reducing the content of phospholipids in an oil composition, the method comprising a) providing an oil composition containing a quantity of phospholipids, b) contacting said oil composition with a phosphatidylinositol phospholipase C (PI-specific PLC), and a PC and PE-specific phospholipase C under conditions sufficient for the enzymes to react with the phospholipids to create diglyceride and phosphate ester, and, c) separating the phosphate ester from the oil composition. In a preferred embodiment the phosphatidylinositol phospholipase C is from the genus of Pseudomonas. In other preferred embodiments, the oil is subject to acid/base treatment prior to being contacted with the phospholipase(s).

In a preferred embodiment, the phosphatidylinositol phospholipase C is a) a polypeptide comprising an amino acid sequence selected from the group consisting of: i) amino acid residues 26-322 of SEQ ID NO: 2 or amino acid residues 1-298 of SEQ ID NO: 3; ii) amino acid residues 26-323 of SEQ ID NO: 5 or amino acid residues 1-299 of SEQ ID NO: 6; iii)amino acid residues 26-323 of SEQ ID NO: 8 or amino acid residues 1-299 of SEQ ID NO: 9; iv) amino acid residues 26-323 of SEQ ID NO: 11 or amino acid residues 1-296 of SEQ ID NO: 12; v) amino acid residues 26-322 of SEQ ID NO: 14 or amino acid residues 1-298 of SEQ ID NO: 15; vi)amino acid residues 26-322 of SEQ ID NO: 17; and vii) amino acid residues 28-339 of SEQ ID NO: 35; or b) a polypeptide comprising an amino acid sequence which has at least 75% identity to one of the amino acid sequences in a); or c) a functional fragment of a) or b).

In some embodiments, said phosphatidylinositol phospholipase C is a polypeptide having a length of 280-320 amino acid residues, such as a length of 280-310 amino acid residues, 280-305 amino acid residues, 280-300 amino acid residues, 280-298 amino acid residues, 280-297 amino acid residues, 280-296 amino acid residues, 285-320 amino acid residues, 285-315 amino acid residues, 285-310 amino acid residues, 285-305 amino acid residues, 285-300 amino acid residues, 285-298 amino acid residues, 285-297 amino acid residues, 285-296 amino acid residues, 290-320 amino acid residues, 290-315 amino acid residues, 290-310 amino acid residues, 290-305 amino acid residues, 290-300 amino acid residues, 290-298 amino acid residues, 290-297 amino acid residues, 290-296 amino acid residues, 295-320 amino acid residues, 295-315 amino acid residues, 295-310 amino acid residues, 295-305 amino acid residues, 295-300 amino acid residues, 295-298 amino acid residues, 255-297 amino acid residues, or a length of 295-296 amino acid residues.

According to other embodiments, the said PC and PE-specific phospholipase C is a polypeptide having a length of 220-280 amino acid residues, such as a length of 220-270 amino acid residues, 220-260 amino acid residues, 220-250 amino acid residues, 220-248 amino acid residues, 220-246 amino acid residues, 220-244 amino acid residues, 225-280 amino acid residues, 225-270 amino acid residues, 225-260 amino acid residues, 225-250 amino acid residues, 225-248 amino acid residues, 225-246 amino acid residues, 225-244 amino acid residues, 230-280 amino acid residues, 230-270 amino acid residues, 230-260 amino acid residues, 230-250 amino acid residues, 230-248 amino acid residues, 230-246 amino acid residues, 230-244 amino acid residues, 235-280 amino acid residues, 235-270 amino acid residues, 235-260 amino acid residues, 235-250 amino acid residues, 235-248 amino acid residues, 235-246 amino acid residues, 235-244 amino acid residues, 240-280 amino acid residues, 240-270 amino acid residues, 240-260 amino acid residues, 240-250 amino acid residues, 240-248 amino acid residues, 240-246 amino acid residues, 240-244 amino acid residues, 242-280 amino acid residues, 242-270 amino acid residues, 242-260 amino acid residues, 242-250 amino acid residues, 242-248 amino acid residues, 242-246 amino acid residues, 242-244 amino acid residues, 243-280 amino acid residues, 243-270 amino acid residues, 243-260 amino acid residues, 243-250 amino acid residues, 243-248 amino acid residues, 243-246 amino acid residues, 243-244 amino acid residues, In still further embodiments, the oil is contacted:
with 0.5-200 mg enzyme protein (EP)/Kg oil of said phosphatidylinositol phospholipase C and with 0.5-200 mg enzyme protein (EP)/Kg oil of said PC and PE-specific phospholipase C; such as
with 0.5-100 mg enzyme protein (EP)/Kg oil of said phosphatidylinositol phospholipase C and with 0.5-100 mg enzyme protein (EP)/Kg oil of said PC and PE-specific phospholipase C;
with 0.5-25 mg enzyme protein (EP)/Kg oil of said phosphatidylinositol phospholipase C and with 0.5-25 mg enzyme protein (EP)/Kg oil of said PC and PE-specific phospholipase C;
with 0.5-15 mg enzyme protein (EP)/Kg oil of said phosphatidylinositol phospholipase C and with 0.5-15 mg enzyme protein (EP)/Kg oil of said PC and PE-specific phospholipase C,
with 0.5-10 mg enzyme protein (EP)/Kg oil of said phosphatidylinositol phospholipase C and with 0.5-10 mg enzyme protein (EP)/Kg oil of said PC and PE-specific phospholipase C,
with 0.5-5 mg enzyme protein (EP)/Kg oil of said phosphatidylinositol phospholipase C and with 0.5-5 mg enzyme protein (EP)/Kg oil of said PC and PE-specific phospholipase C,
with 1-200 mg enzyme protein (EP)/Kg oil of said phosphatidylinositol phospholipase C and with 1-200 mg enzyme protein (EP)/Kg oil of said PC and PE-specific phospholipase C; such as
with 1-100 mg enzyme protein (EP)/Kg oil of said phosphatidylinositol phospholipase C and with 1-100 mg enzyme protein (EP)/Kg oil of said PC and PE-specific phospholipase C;
with 1-25 mg enzyme protein (EP)/Kg oil of said phosphatidylinositol phospholipase C and with 1-25 mg enzyme protein (EP)/Kg oil of said PC and PE-specific phospholipase C;
with 1-15 mg enzyme protein (EP)/Kg oil of said phosphatidylinositol phospholipase C and with 1-15 mg enzyme protein (EP)/Kg oil of said PC and PE-specific phospholipase C,
with 1-10 mg enzyme protein (EP)/Kg oil of said phosphatidylinositol phospholipase C and with 1-10 mg enzyme protein (EP)/Kg oil of said PC and PE-specific phospholipase C,
with 1-5 mg enzyme protein (EP)/Kg oil of said phosphatidylinositol phospholipase C and with 1-5 mg enzyme protein (EP)/Kg oil of said PC and PE-specific phospholipase C,
with 2-200 mg enzyme protein (EP)/Kg oil of said phosphatidylinositol phospholipase C and with 2-200 mg enzyme protein (EP)/Kg oil of said PC and PE-specific phospholipase C,
with 2-100 mg enzyme protein (EP)/Kg oil of said phosphatidylinositol phospholipase C and with 2-100 mg enzyme protein (EP)/Kg oil of said PC and PE-specific phospholipase C,
with 2-50 mg enzyme protein (EP)/Kg oil of said phosphatidylinositol phospholipase C and with 2-50 mg enzyme protein (EP)/Kg oil of said PC and PE-specific phospholipase C,
with 2-25 mg enzyme protein (EP)/Kg oil of said phosphatidylinositol phospholipase C and with 2-25 mg enzyme protein (EP)/Kg oil of said PC and PE-specific phospholipase C,
with 2-15 mg enzyme protein (EP)/Kg oil of said phosphatidylinositol phospholipase C and with 2-15 mg enzyme protein (EP)/Kg oil of said PC and PE-specific phospholipase C,
with 2-10 mg enzyme protein (EP)/Kg oil of said phosphatidylinositol phospholipase C and with 2-10 mg enzyme protein (EP)/Kg oil of said PC and PE-specific phospholipase C,
with 2-7 mg enzyme protein (EP)/Kg oil of said phosphatidylinositol phospholipase C and with 2-7 mg enzyme protein (EP)/Kg oil of said PC and PE-specific phospholipase C, or
with 2-5 mg enzyme protein (EP)/Kg oil of said phosphatidylinositol phospholipase C and with 2-5 mg enzyme protein (EP)/Kg oil of said PC and PE-specific phospholipase C.

In a further embodiment, the PC and PE-specific phospholipase C is a) a polypeptide comprising an amino acid sequence selected from the group consisting of: i) amino acid residues 34-278 of SEQ ID NO: 19 or amino acid residues 1-246 of SEQ ID NO: 20; ii) amino acid residues 25-283 of SEQ ID NO: 22 or amino acid residues 39-283 of SEQ ID NO: 22; iii) amino acid residues 25-283 of SEQ ID NO: 24 or amino acid residues 39-283 of SEQ ID NO: 24 or amino acid residues 1-260 of SEQ ID NO: 25; iv) amino acid residues 25-283 of SEQ ID NO: 27 or amino acid residues 39-283 of SEQ ID NO: 27; v) amino acid residues 28-289 of SEQ ID NO: 29 or amino acid residues 52-289 of SEQ ID NO: 29 or amino acid residues 1-263 of SEQ ID NO: 30; vi) amino acid residues 21-282 of SEQ ID NO: 32 or amino acid residues 38-282 of SEQ ID NO: 32; vii) amino acid residues 25-280 of SEQ ID NO: 38 or amino acid residues 36-280 of SEQ ID NO: 38; and vii) Purafine; or b) a polypeptide comprising an amino acid sequence which has at least 75% identity to one of the amino acid sequences in a); or c) a functional fragment of a) or b).

Another aspect of the present invention is a method for reducing the content of phospholipids in an oil composition, the method comprising: a) providing an oil composition containing a quantity of phospholipids, b) contacting said oil composition with a PC and PE-specific phospholipase C selected from i) a polypeptide comprising an amino acid sequence selected from the group consisting of: 1) amino acid residues 34-278 of SEQ ID NO: 19 or amino acid residues 1-246 of SEQ ID NO: 20; 2) amino acid residues 25-283 of SEQ ID NO: 24, amino acid residues 39-283 of SEQ ID NO: 24 or amino acid residues 1-260 of SEQ ID NO: 25; 3) amino acid residues 25-283 of SEQ ID NO: 27 or amino acid residues 39-283 of SEQ ID NO: 27; 4) amino acid residues 28-289 of SEQ ID NO: 29, or amino acid residues 52-289 of SEQ ID NO: 29 or amino acid residues 1-263 of SEQ ID NO: 30; ii) a polypeptide comprising an amino acid sequence which has at least 75% identity to one of the amino acid sequences in i); or iii) a functional fragment of i) or ii) under conditions sufficient for the enzymes to react with the phospholipids to create diglyceride and phosphate ester, and c) separating the phosphate ester from the oil composition.

Phospholipids are commonly measured in oil as "phosphorous content" in parts per million. Table 1 sets forth the typical amounts of phospholipids present in the major oilseed crops, and the distribution of the various functional groups as a percentage of the phospholipids present in the oil.

TABLE 1

Typical levels and phospholipid distributions for common oilseeds

|  | Soy Oil | Canola Oil | Sunflower Oil |
| --- | --- | --- | --- |
| Phosphorous (ppm) | 400-1500 | 200-900 | 300-700 |
| PC % | 12-46 | 25-40 | 29-52 |
| PE % | 8-34 | 15-25 | 17-26 |
| PA % | 17-26 | 10-20 | 15-30 |
| PI % | 2-15 | 2-25 | 11-22 |

The enzymes and processes of the invention can be used to achieve a more complete degumming of high phosphorous oils, e.g., an oil with more than 200 ppm of phosphorous, preferably more than 300 ppm, 400 ppm, 500 ppm, 600 ppm, 700 ppm, 800 ppm, 900 ppm, even more preferred the oil contains more than 1000 ppm phosphorous.

Preferably the oil comprises phosphatidylcholine (PC), phosphatidylethanolamine (PE) and phosphatidyl inositol (PI). Preferably the oil contains more than 50 ppm phosphorous originating from phosphatidyl inositol (PI), more preferably it contains more than 75 ppm, 100 ppm, 125 ppm PI, even more preferably it contains more than 150 ppm, most preferably it contains more than 175 ppm phosphorous originating from PI. Preferably the oil contains more than 100 ppm phosphorous originating from phosphatidylcholine (PC), more preferably it contains more than 150 ppm, 200 ppm, 250 ppm PC, even more preferably it contains more than 300 ppm, most preferably it contains more than 400 ppm phosphorous originating from PC. Preferably the oil contains more than 75 ppm phosphorus originating from phosphatidylethanolamine (PE), more preferably it contains more than 100 ppm, 125 ppm, 150 ppm PE, even more preferably it contains more than 200 ppm, most preferably it contains more than 300 ppm phosphorous originating from PE.

In a preferred embodiment the oil is an edible oil. More preferred the edible oil is selected from rice bran, rapeseeds, palm, peanuts and other nuts, soybean, corn, canola, and sunflower oils. The phospholipases of the invention can be used in any "degumming" procedure, including water degumming, ALCON oil degumming (e.g., for soybeans), safinco degumming, "super degumming," UF degumming, TOP degumming, uni-degumming, dry degumming and ENZYMAX™ degumming. See, for example, WO 2007/103005, US 2008/0182322, U.S. Pat. Nos. 6,355,693, 6,162,623, 6,103,505, 6,001,640, 5,558,781 and 5,264,367 for description of degumming processes where phospholipases of the present invention can be applied. Various "degumming" procedures incorporated by the methods of the invention are described in Bockisch, M. (1998) In Fats and Oils Handbook, The extraction of Vegetable Oils (Chapter 5), 345-5 445, AOCS Press, Champaign, Illinois. The phospholipases of the invention can be used in the industrial application of enzymatic degumming of triglyceride oils as described, e.g., in EP 513 709. In a further embodiment the oil is selected from crude oil, water degummed oil, caustic refined oil and acid degummed oil. The water-degumming of a crude oil or fat may be achieved by thoroughly mixing hot water and warm oil or fat having a temperature of between 50° C. to 90° C. for 30 to 60 minutes. This process serves to partially remove the hydratable phospholipids. Also, an acid treatment may be performed before the enzymatic degumming, where the acid used is selected from the group consisting of phosphoric acid, acetic acid, citric acid, tartaric acid, succinic acid, and mixtures thereof, in particular, a treatment using citric acid or phosphoric acid is preferred. The acid treatment is preferably followed by a neutralization step to adjust the pH between about 4.0 to 7.0, more preferably from 4.5 to 6.5, preferably using NaOH or KOH. The acid treatment serves to chelate metals bound to the phospholipids hereby making a more hydratable form. Preferably, the phospholipases as described herein is added after water degumming or acid treatment of the oil. It is also possible to perform the degumming step using the phospholipases as described herein on a crude oil or fat, i.e., an oil or fat not previously water degummed or acid treated.

In one aspect, the invention provides methods for enzymatic degumming under conditions of low water, e.g., in the range of between about 0.1% to 20% water or 0.5% to 10% water. In one aspect, this results in the improved separation of a heavy phase from the oil phase during centrifugation. The improved separation of these phases can result in more efficient removal of phospholipids from the oil, including both hydratable and nonhydratable phospholipids. In one aspect, this can produce a gum fraction that contains less entrained neutral oil (triglycerides), thereby improving the overall yield of oil during the degumming process. In one aspect, phospholipases of the invention, e.g., a PI-specific-PLC and/or PC, PE-specific PLC, are used to treat oils to reduce gum mass and increase neutral oil gain through reduced oil entrapment. In one aspect, phospholipases of the invention, e.g., a polypeptide having PLC activity, are used for diacylglycerol (DAG) production and to contribute to the oil phase.

The phospholipase treatment can be conducted by dispersing an aqueous solution of the phospholipase, preferably as droplets with an average diameter below 10 μM. The amount of water is preferably 0.5-5% by weight in relation to the oil. An emulsifier may optionally be added. Mechanical agitation may be applied to maintain the emulsion. Agitation may be done with a high shear mixer with a tip speed above 1400 cm/s.

In certain embodiments, a suitable oil degumming method comprises a) mixing an aqueous acid with an oil to obtain an acidic mixture having pH of about 1 to 4, b) mixing a base with the acidic mixture to obtain a reacted mixture having pH of about 6-9, and c) degumming the reacted mixture with an enzyme of the present invention to obtain a degummed oil. In certain embodiments, mixing in steps a) and/or b) creates an emulsion that comprises an aqueous phase in average droplet size between about 15 μM to about 45 μM.

In certain embodiments, mixing in steps a) and/or b) creates an emulsion that comprises at least about 60% of an aqueous phase by volume in droplet size between about 15 μM to about 45 μM in size, wherein percentage of the aqueous phase is based on the total volume of the aqueous phase. Any acid deemed suitable by one of skill in the art can be used in the methods provided herein. In certain embodiments, the acid is selected from the group consisting of phosphoric acid, acetic acid, citric acid, tartaric acid, succinic acid, and a mixture thereof. Any acid deemed suitable by one of skill in the art can be used in the methods provided herein. In certain embodiments, the base is selected from the group consisting of sodium hydroxide, potassium hydroxide, sodium silicate, sodium carbonate, calcium carbonate, and a combination thereof.

In a preferred embodiment, the phospholipase treatment can be conducted at a pH in the range of about 4.0 to 7.0, more preferably from 4.5 to 6.5. The pH is measured in the emulsion or in the interphase between the between oil and aqueous solution. A suitable temperature is generally 30-80° C. In a preferred embodiment the temperature of the oil is between 50 and 70° C., more preferred between 55 and 65° C. and most preferred between 50 and 60° C. In other preferred embodiments the temperature of the oil is between 60 and 80° C., more preferred between 65 and 75° C. and most preferred between 67 and 72° C.

The reaction time will typically be 1-12 hours (e.g., 1-6 hours, or 1-3 hours, most preferred the reaction time is between 1.5 and 4 hours, even more preferred between 1.5 and 2 hours). A suitable enzyme dosage will usually be 0.1-10 mg per liter (e.g., 0.5-5 mg per liter). The phospholipase treatment may be conducted batch wise, e.g., in a tank with stirring, or it may be continuous, e.g., a series of stirred tank reactors. The phospholipase treatment may be followed by separation of an aqueous phase and an oil phase. The separation may be performed by conventional means, e.g., centrifugation. When a liquid lipase is used the aqueous phase will contain phospholipase, and the enzyme may be re-used to improve the process economy.

In a preferred embodiment of the present invention, the treatment reduces the total phosphorous content of the oil to below 200 ppm, preferably below 100 ppm, below 50 ppm, below 40 ppm, 30 ppm, 20 ppm, 15 ppm, more preferably below 10 ppm, below 9 ppm, below 8 ppm, below 7 ppm, below 6 ppm, most preferably below 5 ppm.

In addition to the phospholipases of the present invention, a further enzyme may be applied in the degumming process outlined above. In a preferred embodiment the further enzyme is a polypeptide having phospholipase A1, A2 and/or B activity. A suitable polypeptide having phospholipase A1 activity may be LECITASE ULTRA available from Novozymes A/S.

Phospholipid emulsifiers: The phospholipase of the invention may be used for partial hydrolysis of phospholipids, preferably lecithin, to obtain improved phospholipid emulsifiers. This application is further described in Ullmann's Encyclopedia of Industrial Chemistry (Publisher: VCH Weinheim (1996)), JP 2794574, and JP-B 6-087751.

Filtration: The phospholipase of the invention can be used to improve the filterability of an aqueous solution or slurry of carbohydrate origin by treating it with the phospholipase. This is particularly applicable to a solution of slurry containing a starch hydrolyzate, especially a wheat starch hydrolyzate, since this tends to be difficult to filter and to give cloudy filtrates. The treatment can be done in analogy with EP 219269 (CPC International).

Animal feed: The phospholipase of the invention may be used in a process for the production of an animal feed which comprises mixing the phospholipase with feed substances comprising at least one phospholipid. This can be done in analogy with EP 743017.

Biodiesel: The phospholipase of the present invention may be used in combination with one or more lipolytic enzymes to convert fats and oils to fatty acid alkyl esters while achieving degumming in the same process. Such a process is for example described in U.S. Pat. No. 8,012,724.

Detergent: The phospholipase of the invention may be added to and thus be used as a component of a detergent composition.

The detergent composition may for example be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations.

Baking: The phospholipase of the invention may be used for production of dough and baked products from dough, as well as for production of baking compositions and baking additives.

The dough generally comprises wheat meal or wheat flour and/or other types of meal, flour or starch such as corn flour, corn starch, rye meal, rye flour, oat flour, oat meal, soy flour, sorghum meal, sorghum flour, potato meal, potato flour or potato starch.

The dough may be fresh, frozen or par-baked.

The dough is normally leavened dough or dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening, but the invention is particularly applicable to a dough where less than 1% by weight of fat is added, and particularly to a dough which is made without addition of fat.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin.

The dough may be used for any kind of baked product prepared from dough, either of a soft or a crisp character, either of a white, light or dark type. Examples are bread (in particular, white, whole-meal or rye bread), typically in the form of loaves or rolls, French baguette-type bread, pita bread, tortillas, cakes, pancakes, biscuits, wafers, cookies, pie crusts, crisp bread, steamed bread, pizza and the like.

The present invention is further described by the following examples that should not be construed as limiting the scope of the invention.

Items

1. A method for reducing the content of phospholipids in an oil composition, the method comprising
    a) providing an oil composition containing a quantity of phospholipids,
    b) contacting said oil composition with a phosphatidylinositol phospholipase C and a PC and PE-specific phospholipase C under conditions sufficient for the enzymes to react with the phospholipids to create diglyceride and phosphate ester; and
    c) separating the phosphate ester from the oil composition.
2. The method of item 1 wherein said phosphatidylinositol phospholipase C is from the genus of *Pseudomonas*.
3. The method of item 1 or 2, wherein the oil is an edible oil.
4. The method of any of the preceding items, wherein the oil is selected from group consisting of crude oil, water degummed oil, caustic refined oil and acid degummed oil.
5. The method of any of the proceeding items, where in the oil comprises phosphatidylcholine (PC), phosphatidylethanolamine (PE) and phosphatidyl inositol (PI).
6. The method of item 5, wherein the oil comprises at least 50 ppm phosphorus originating from phosphatidyl inositol (PI).
7. The method of any of the proceeding items, where the phosphatidylinositol phospholipase C is
    a) a polypeptide comprising an amino acid sequence selected from the group consisting of:
        i) amino acid residues 26-322 of SEQ ID NO: 2 or amino acid residues 1-298 of SEQ ID NO: 3;
        ii) amino acid residues 26-323 of SEQ ID NO: 5 or amino acid residues 1-299 of SEQ ID NO: 6;
        iii) amino acid residues 26-323 of SEQ ID NO: 8 or amino acid residues 1-299 of SEQ ID NO: 9;
        iv) amino acid residues 26-323 of SEQ ID NO: 11 or amino acid residues 1-296 of SEQ ID NO: 12;
        v) amino acid residues 26-322 of SEQ ID NO: 14 or amino acid residues 1-298 of SEQ ID NO: 15;
        vi) amino acid residues 26-322 of SEQ ID NO: 17; and
        vii) amino acid residues 28-339 of SEQ ID NO: 35; or
    b) a polypeptide comprising an amino acid sequence which has at least 75% identity to one of the amino acid sequences in a); or
    c) a functional fragment of a) or b).
8. The method of any of the proceeding items, where the PC and PE-specific phospholipase C is
    a) a polypeptide comprising an amino acid sequence selected from the group consisting of:
        i) amino acid residues 34-278 of SEQ ID NO: 19 or amino acid residues 1-246 of SEQ ID NO: 20;
        ii) amino acid residues 25-283 of SEQ ID NO: 22 or amino acid residues 39-283 of SEQ ID NO: 22;
        iii) amino acid residues 25-283 of SEQ ID NO: 24 or amino acid residues 39-283 of SEQ ID NO: 24 or amino acid residues 1-260 of SEQ ID NO: 25;
        iv) amino acid residues 25-283 of SEQ ID NO: 27 or amino acid residues 39-283 of SEQ ID NO: 27;
        v) amino acid residues 28-289 of SEQ ID NO: 29 or amino acid residues 52-289 of SEQ ID NO: 29 or amino acid residues 1-263 of SEQ ID NO: 30;
        vi) amino acid residues 21-282 of SEQ ID NO: 32 or amino acid residues 38-282 of SEQ ID NO: 32;
        vii) amino acid residues 25-280 of SEQ ID NO: 38 or amino acid residues 36-280 of SEQ ID NO: 38; and
        viii) Purifine; or
    b) a polypeptide comprising an amino acid sequence which has at least 75% identity to one of the amino acid sequences in a); or
    c) a functional fragment of a) or b).
9. The method of any of the preceding items, wherein said phosphatidylinositol phospholipase C is a polypeptide having a length of 280-320 amino acid residues, such as a length of 280-310 amino acid residues, 280-305 amino acid residues, 280-300 amino acid residues, 280-298 amino acid residues, 280-297 amino acid residues, 280-296 amino acid residues, 285-320 amino acid residues, 285-315 amino acid residues, 285-310 amino acid residues, 285-305 amino acid residues, 285-300 amino acid residues, 285-298 amino acid residues, 285-297 amino acid residues, 285-296 amino acid residues, 290-320 amino acid residues, 290-315 amino acid residues, 290-310 amino acid residues, 290-305 amino acid residues, 290-300 amino acid residues, 290-298 amino acid residues, 290-297 amino acid residues, 290-296 amino acid residues, 295-320 amino acid residues, 295-315 amino acid residues, 295-310 amino acid residues, 295-305 amino acid residues, 295-300 amino acid residues, 295-298 amino acid residues, 255-297 amino acid residues, or a length of 295-296 amino acid residues.
10. The polypeptide of any of the preceding items, wherein said PC and PE-specific phospholipase C is a polypeptide having a length of 220-280 amino acid residues, such as a length of 220-270 amino acid residues, 220-260 amino acid residues, 220-250 amino acid residues, 220-248 amino acid residues, 220-246 amino acid residues, 220-244 amino acid residues, 225-280 amino acid residues, 225-270 amino acid residues, 225-260 amino acid residues, 225-250 amino acid residues, 225-248 amino acid residues, 225-246 amino acid residues, 225-244 amino acid residues, 230-280 amino acid residues, 230-270 amino acid residues, 230-260 amino acid residues, 230-250 amino acid residues, 230-248 amino acid residues, 230-246 amino acid residues, 230-244 amino acid residues, 235-280 amino acid residues, 235-270 amino acid residues, 235-260 amino acid residues, 235-250 amino acid residues, 235-248 amino acid residues, 235-246 amino acid residues, 235-244 amino acid residues, 240-280 amino acid residues, 240-270 amino acid residues, 240-260 amino acid residues, 240-250 amino acid residues, 240-248 amino acid residues, 240-246 amino acid residues, 240-244 amino acid residues, 242-280 amino acid residues, 242-270 amino acid residues, 242-260 amino acid residues, 242-250 amino acid residues, 242-248 amino acid residues, 242-246 amino acid residues, 242-244 amino acid residues, 243-280 amino acid residues, 243-270 amino acid residues, 243-260 amino acid residues, 243-250 amino acid residues, 243-248 amino acid residues, 243-246 amino acid residues, 243-244 amino acid residues.
11. The method of any of the preceding items, wherein said oil is contacted:
    with 0.5-200 mg enzyme protein (EP)/Kg oil of said phosphatidylinositol phospholipase C and with 0.5-200 mg enzyme protein (EP)/Kg oil of said PC and PE-specific phospholipase C; such as
    with 0.5-100 mg enzyme protein (EP)/Kg oil of said phosphatidylinositol phospholipase C and with 0.5-100 mg enzyme protein (EP)/Kg oil of said PC and PE-specific phospholipase C;

with 0.5-25 mg enzyme protein (EP)/Kg oil of said phosphatidylinositol phospholipase C and with 0.5-25 mg enzyme protein (EP)/Kg oil of said PC and PE-specific phospholipase C;

with 0.5-15 mg enzyme protein (EP)/Kg oil of said phosphatidylinositol phospholipase C and with 0.5-15 mg enzyme protein (EP)/Kg oil of said PC and PE-specific phospholipase C, with 0.5-10 mg enzyme protein (EP)/Kg oil of said phosphatidylinositol phospholipase C and with 0.5-10 mg enzyme protein (EP)/Kg oil of said PC and PE-specific phospholipase C, with 0.5-5 mg enzyme protein (EP)/Kg oil of said phosphatidylinositol phospholipase C and with 0.5-5 mg enzyme protein (EP)/Kg oil of said PC and PE-specific phospholipase C, with 1-200 mg enzyme protein (EP)/Kg oil of said phosphatidylinositol phospholipase C and with 1-200 mg enzyme protein (EP)/Kg oil of said PC and PE-specific phospholipase C; such as with 1-100 mg enzyme protein (EP)/Kg oil of said phosphatidylinositol phospholipase C and with 1-100 mg enzyme protein (EP)/Kg oil of said PC and PE-specific phospholipase C;

with 1-25 mg enzyme protein (EP)/Kg oil of said phosphatidylinositol phospholipase C and with 1-25 mg enzyme protein (EP)/Kg oil of said PC and PE-specific phospholipase C;

with 1-15 mg enzyme protein (EP)/Kg oil of said phosphatidylinositol phospholipase C and with 1-15 mg enzyme protein (EP)/Kg oil of said PC and PE-specific phospholipase C, with 1-10 mg enzyme protein (EP)/Kg oil of said phosphatidylinositol phospholipase C and with 1-10 mg enzyme protein (EP)/Kg oil of said PC and PE-specific phospholipase C, with 1-5 mg enzyme protein (EP)/Kg oil of said phosphatidylinositol phospholipase C and with 1-5 mg enzyme protein (EP)/Kg oil of said PC and PE-specific phospholipase C, with 2-200 mg enzyme protein (EP)/Kg oil of said phosphatidylinositol phospholipase C and with 2-200 mg enzyme protein (EP)/Kg oil of said PC and PE-specific phospholipase C, with 2-100 mg enzyme protein (EP)/Kg oil of said phosphatidylinositol phospholipase C and with 2-100 mg enzyme protein (EP)/Kg oil of said PC and PE-specific phospholipase C, with 2-50 mg enzyme protein (EP)/Kg oil of said phosphatidylinositol phospholipase C and with 2-50 mg enzyme protein (EP)/Kg oil of said PC and PE-specific phospholipase C, with 2-25 mg enzyme protein (EP)/Kg oil of said phosphatidylinositol phospholipase C and with 2-25 mg enzyme protein (EP)/Kg oil of said PC and PE-specific phospholipase C, with 2-15 mg enzyme protein (EP)/Kg oil of said phosphatidylinositol phospholipase C and with 2-15 mg enzyme protein (EP)/Kg oil of said PC and PE-specific phospholipase C, with 2-10 mg enzyme protein (EP)/Kg oil of said phosphatidylinositol phospholipase C and with 2-10 mg enzyme protein (EP)/Kg oil of said PC and PE-specific phospholipase C, with 2-7 mg enzyme protein (EP)/Kg oil of said phosphatidylinositol phospholipase C and with 2-7 mg enzyme protein (EP)/Kg oil of said PC and PE-specific phospholipase C, with 2-5 mg enzyme protein (EP)/Kg oil of said phosphatidylinositol phospholipase C and with 2-5 mg enzyme protein (EP)/Kg oil of said PC and PE-specific phospholipase C.

12. A polypeptide having phosphatidylinositol phospholipase C activity, selected from the group consisting of:
  a) a polypeptide having at least 91% sequence identity to the mature polypeptide of SEQ ID NO: 2;
  b) a polypeptide encoded by a polynucleotide that hybridizes under medium stringency conditions with
    i) the mature polypeptide coding sequence of SEQ ID NO: 1, or
    ii) the full-length complement of (i);
  c) a polypeptide encoded by a polynucleotide having at least 90% sequence identity to the mature polypeptide coding sequence of SEQ ID NO: 1;
  d) a variant of the mature polypeptide of SEQ ID NO: 2 comprising a substitution, deletion, and/or insertion at one or more positions; and
  e) a fragment of the polypeptide of (a), (b), (c), or (d) that has phosphatidylinositol phospholipase C activity.

13. The polypeptide of item 12, said polypeptide having a thermal denaturation temperature of at least 60° C., such as 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C. or at least 90° C. as determined by Differential Scanning calorimetry (DSC).

14. The polypeptide of item 12 or 13, wherein said denaturation temperature is determined as the top of denaturation peak (major endothermic peak) in thermograms (Cp vs. T) obtained after heating a 1 mg/ml solution of the polypeptide in buffer (50 mM Na-acetate pH 5.5, or 50 mM Hepes pH 7) at a constant programmed heating rate of 200 K/hr.

15. The polypeptide of any of items 12-14, said polypeptide being able to reduce the phosphatidylinositol content of crude soy bean oil by 50% or more, 50%, such as by 55%, by 60%, by 65%, by 70%, by 75%, by 80%, by 85%, by 90% or by 95% or more, the reduction in phosphatidylinositol content being determined by $^{31}$P-NMR after addition of 100 mg enzyme protein (EP)/kg oil and incubation of the oil and enzyme at 50° C. for 2 hours at pH 5.5.

16. The polypeptide of any of items 12-15, said polypeptide being able to reduce the phosphorous content of crude soy bean oil to 20 mg/kg oil or less as determined by Inductively coupled plasma optical emission spectrometry (ICP-OES) after incubation of 4 mg enzyme protein/kg oil in a low aqueous system comprising 3% water based on oil amount at 50-60° C. for 5 hours.

17. The polypeptide of item 16, wherein said crude soy oil comprises 80-140 ppm phosphorous present as phosphatidic acid (PA), 140-200 ppm phosphorous present as phosphatidyl ethanolamine (PE), 70-110 ppm phosphorous present as phosphatidic acid (PI) and 130-200 ppm phosphorous present as phosphatidyl choline; the phosphorous content being measured by $^{31}$P-NMR.

18. The polypeptide of item 16 or 17, wherein the reduction of phosphorous content is obtained in an oil degumming process comprising the steps of:
  i) Optionally treating crude soy bean oil with acid/base by adding an 85% solution of Ortho Phosphoric acid in amounts corresponding to 0.05% (100% pure Ortho Phosphoric acid) based on oil amount, mixing in ultrasonic bath for 5 minutes, followed by incubation in rotator for 15 minutes and base neutralization with 4 M NaOH applied in equivalents (from 0.5 to 0.15) to pure Ortho Phosphoric acid in ultrasonic bath for 5 minutes;
ii) Adding the polypeptide to the oil in amounts of 4 mg enzyme protein/kg oil in a low aqueous system comprising 3% water based on oil amount and subjecting the oil and the polypeptide to ultrasonic treatment for 5 minutes;
iii) Incubating the polypeptide and oil at 50-60° C. for 5 hours with stirring at 20 rpm;
iv) Centrifuging the oil and the polypeptide at 700 g at 85° C. for 15 minutes.

19. The polypeptide of any of items 12-18, comprising, consisting of or consisting essentially of SEQ ID NO: 2 or the mature polypeptide of SEQ ID NO: 2 or amino acids 26 to 322 of SEQ ID NO: 2 or to amino acids 1 to 298 of SEQ ID NO: 3.

20. The polypeptide of any of items 12-19, having a length of 280-320 amino acid residues, such as a length of 280-310 amino acid residues, 280-305 amino acid residues, 280-300 amino acid residues, 280-298 amino acid residues, 280-297 amino acid residues, 280-296 amino acid residues, 285-320 amino acid residues, 285-315 amino acid residues, 285-310 amino acid residues, 285-305 amino acid residues, 285-300 amino acid residues, 285-298 amino acid residues, 285-297 amino acid residues, 285-296 amino acid residues, 290-320 amino acid residues, 290-315 amino acid residues, 290-310 amino acid residues, 290-305 amino acid residues, 290-300 amino acid residues, 290-298 amino acid residues, 290-297 amino acid residues, 290-296 amino acid residues, 295-320 amino acid residues, 295-315 amino acid residues, 295-310 amino acid residues, 295-305 amino acid residues, 295-300 amino acid residues, 295-298 amino acid residues, 255-297 amino acid residues, or a length of 295-296 amino acid residues.

21. A polypeptide having PC and PE specific phospholipase C activity, selected from the group consisting of:
   a) a polypeptide having at least 70% sequence identity to the mature polypeptide of SEQ ID NO: 19;
   b) a polypeptide encoded by a polynucleotide that hybridizes under low stringency conditions with
      i) the mature polypeptide coding sequence of SEQ ID NO: 18, or
      ii) the full-length complement of (i);
   c) a polypeptide encoded by a polynucleotide having at least 70% sequence identity to the mature polypeptide coding sequence of SEQ ID NO: 18;
   d) a variant of the mature polypeptide of SEQ ID NO: 19 comprising a substitution, deletion, and/or insertion at one or more positions; and
   e) a fragment of the polypeptide of (a), (b), (c), or (d) that has PC and PE specific phospholipase C activity.

22. The polypeptide of item 21, said polypeptide having a thermal denaturation temperature of at least 60° C., such as 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C. or at least 90° C. as determined by Differential Scanning calorimetry (DSC).

23. The polypeptide of item 22, wherein said denaturation temperature is determined as the top of denaturation peak (major endothermic peak) in thermograms (Cp vs. T) obtained after heating a 1 mg/ml solution of the polypeptide in buffer (50 mM Na-acetate pH 5.5, or 50 mM Hepes pH 7) at a constant programmed heating rate of 200 K/hr.

24. The polypeptide of any of items 21-23, said polypeptide being able to reduce the phosphatidyl ethanolamine and/or phosphatidyl choline content of crude soy bean oil by 50% or more, 50%, such as by 55%, by 60%, by 65%, by 70%, by 75%, by 80%, by 85%, by 90% or by 95% or more, the reduction in phosphatidyl ethanolamine and/or phosphatidyl choline content being determined by $^{31}$P-NMR after addition of 100 mg enzyme protein (EP)/kg oil and incubation of the oil and enzyme at 50° C. for 2 hours at pH 5.5.

25. The polypeptide of any of items 21-24, said polypeptide being able to reduce the phosphorous content of crude soy bean oil to 20 mg/kg oil or less as determined by Inductively coupled plasma optical emission spectrometry (ICP-OES) after incubation of 4 mg enzyme protein/kg oil in a low aqueous system comprising 3% water based on oil amount at 50-60° C. for 5 hours.

26. The polypeptide of item 24 or 25, wherein said crude soy oil comprises 80-140 ppm phosphorous present as phosphatidic acid (PA), 140-200 ppm phosphorous present as phosphatidyl ethanolamine (PE), 70-110 ppm phosphorous present as phosphatidic acid (PI) and 130-200 ppm phosphorous present as phosphatidyl choline; the phosphorous content being measured by $^{31}$P-NMR.

27. The polypeptide of any of items 24-26, wherein the reduction of phosphorous content and/or reduction in phosphatidyl ethanolamine and/or phosphatidyl choline content is obtained in an oil degumming process comprising the steps of:
   i) Optionally treating crude soy bean oil with acid/base by adding an 85% solution of Ortho Phosphoric acid in amounts corresponding to 0.05% (100% pure Ortho Phosphoric acid) based on oil amount, mixing in ultrasonic bath for 5 minutes, followed by incubation in rotator for 15 minutes and base neutralization with 4 M NaOH applied in equivalents (from 0.5 to 0.15) to pure Ortho Phosphoric acid in ultrasonic bath for 5 minutes;
   ii) Adding the polypeptide to the oil in amounts of 4 mg enzyme protein/kg oil in a low aqueous system comprising 3% water based on oil amount and subjecting the oil and the polypeptide to ultrasonic treatment for 5 minutes;
   iii) Incubating the polypeptide and oil at 50-60° C. for 5 hours with stirring at 20 rpm;
   iv) Centrifuging the oil and the polypeptide at 700 g at 85° C. for 15 minutes.

28. The polypeptide of any of items 21-27, comprising, consisting of or consisting essentially of SEQ ID NO: 19 or the mature polypeptide of SEQ ID NO: 19 or amino acids 34 to 278 of SEQ ID NO: 19 or amino acid residues 1-246 of SEQ ID NO: 20.

29. The polypeptide of any of items 21-28, having a length of 220-280 amino acid residues, such as a length of 220-270 amino acid residues, 220-260 amino acid residues, 220-250 amino acid residues, 220-248 amino acid residues, 220-246 amino acid residues, 220-244 amino acid residues, 225-280 amino acid residues, 225-270 amino acid residues, 225-260 amino acid residues, 225-250 amino acid residues, 225-248 amino acid residues, 225-246 amino acid residues, 225-244 amino acid residues, 230-280 amino acid residues, 230-270 amino acid residues, 230-260 amino acid residues, 230-250 amino acid residues, 230-248 amino acid residues, 230-246 amino acid residues, 230-244 amino acid residues, 235-280 amino acid residues, 235-270 amino acid residues, 235-260 amino acid residues, 235-250 amino acid residues, 235-248 amino acid residues, 235-246 amino acid residues, 235-244 amino acid residues, 240-280 amino acid residues, 240-270 amino acid residues, 240-260 amino acid residues, 240-250 amino acid residues, 240-248 amino acid residues, 240-246 amino acid residues, 240-244 amino acid residues, 242-280 amino acid residues, 242-270 amino acid residues, 242-260 amino acid residues, 242-250 amino acid residues, 242-248 amino acid residues, 242-246 amino acid residues, 242-244 amino acid residues, 243-280 amino acid residues, 243-270 amino acid residues, 243-260 amino acid residues, 243-250 amino acid residues, 243-248 amino acid residues, 243-246 amino acid residues, 243-244 amino acid residues.

30. A polynucleotide encoding a polypeptide of any of items 12 to 29.
31. A nucleic acid construct or expression vector comprising the polynucleotide of item 30 operably linked to one or more control sequences that direct the production of the polypeptide in an expression host.
32. A recombinant host cell comprising the polynucleotide of item 30 operably linked to one or more control sequences that direct the production of the polypeptide.
33. A method of producing a polypeptide of any of items 12 to 29, comprising cultivating a cell, which in its wild-type form produces the polypeptide, under conditions conducive for production of the polypeptide.
34. A method of producing a phospholipase C polypeptide in a *Bacillus* host, wherein the phospholipase C coding sequence encode an alanine in front of the predicted N-terminal amino acid of the phospholipase C polypeptide.
35. The method of item 34, wherein the phospholipase C polypeptide is a PC and PE-specific phospholipase C polypeptide.
36. A method of producing a polypeptide of any of items 12 to 29, comprising cultivating the host cell of item 32 under conditions conducive for production of the polypeptide.
37. The method of any of items 33-37, further comprising recovering the polypeptide.
38. A composition comprising the polypeptide of any of items 12-20.
39. A composition comprising the polypeptide of any of items 21-29.
40. A composition comprising a mixture of a phosphatidylinositol phospholipase C from the genus of *Pseudomonas* and a PC and PE-specific phospholipase C polypeptide.
41. The composition of item 40, wherein the phosphatidylinositol phospholipase C is:
   a) a polypeptide comprising an amino acid sequence selected from the group consisting of:
      i) amino acid residues 26-322 of SEQ ID NO: 2 or amino acid residues 1-298 of SEQ ID NO: 3;
      ii) amino acid residues 26-323 of SEQ ID NO: 5 or amino acid residues 1-299 of SEQ ID NO: 6;
      iii) amino acid residues 26-323 of SEQ ID NO: 8 or amino acid residues 1-299 of SEQ ID NO: 9;
      iv) amino acid residues 26-323 of SEQ ID NO: 11 or amino acid residues 1-296 of SEQ ID NO: 12;
      v) amino acid residues 26-322 of SEQ ID NO: 14 or amino acid residues 1-298 of SEQ ID NO: 15;
      vi) amino acid residues 26-322 of SEQ ID NO: 17; and
      vii) amino acid residues 28-339 of SEQ ID NO: 35; or
   b) a polypeptide comprising an amino acid sequence which has at least 75% identity to one of the amino acid sequences in a); or
   c) a functional fragment of a) or b).
42. The composition of item 41, wherein the phosphatidylinositol phospholipase C is the polypeptide of any of items 12-20.
43. The composition of any of items 38-42, wherein the PC and PE-specific phospholipase C polypeptide is:
   a) a polypeptide comprising an amino acid sequence selected from the group consisting of:
      i) amino acid residues 34-278 of SEQ ID NO: 19 or amino acid residues 1-246 of SEQ ID NO: 20;
      ii) amino acid residues 25-283 of SEQ ID NO: 22 or amino acid residues 39-283 of SEQ ID NO: 22;
      iii) amino acid residues 25-283 of SEQ ID NO: 24 or amino acid residues 39-283 of SEQ ID NO: 24 or amino acid residues 1-260 of SEQ ID NO: 25;
      iv) amino acid residues 39-283 of SEQ ID NO: 27;
      v) amino acid residues 52-289 of SEQ ID NO: 29 or amino acid residues 1-263 of SEQ ID NO: 30
      vi) amino acid residues 21-282 of SEQ ID NO: 32 or amino acid residues 38-282 of SEQ ID NO: 32;
      vii) amino acid residues 25-280 of SEQ ID NO: 38 or amino acid residues 36-280 of SEQ ID NO: 38; and
      viii) Purafine; or
   b) a polypeptide comprising an amino acid sequence which has at least 75% identity to one of the amino acid sequences in a); or
   c) a functional fragment of a) or b).

EXAMPLES

Strains and DNA

The DNA encoding the PLC of SEQ ID NO: 2 was cloned from a *Pseudomonas* species isolated from seaweed sample collected in Denmark.

The DNA encoding the PLC of SEQ ID NO: 19 was cloned from a *Bacillus* sp. obtained from a soil sample collected in Australia in 1990.

The codon optimized DNA encoding the publicly known PLC's was ordered from the companies Geneart (SEQ ID NO: 22, SEQ ID NO: 27 and SEQ ID NO: 29) and Gen9 (SEQ ID NO: 5, SEQ ID NO: 8, SEQ ID NO: 11, SEQ ID NO: 14).

In the examples below the phospholipase C enzymes of the present invention are referred to by SEQ ID NO. If the SEQ ID NO contains a signal peptide it is understood that the reference is to the mature sequence of that SEQ ID NO.

Example 1: Cloning and Expression

The phospholipase encoding genes were either cloned by conventional techniques from the strains indicated above or ordered as synthetic genes and inserted into a suitable plasmid. The genes were expressed with the secretion signal having the following amino acid sequence MKKPLGKIV-ASTALLISVAFSSSIASA (SEQ ID NO: 33) replacing the native secretion signal sequence with an extra alanine at the C-terminal. This results in a recombinant mature polypeptide with an alanine at the front of the N-terminal of the mature wild type sequence. Genes encoding SEQ ID NO: 22, 27 and SEQ ID NO: 38 were cloned using the same strategy, however, no extra alanine was added at the C-terminal of the signal peptide. Thus, the recombinant mature polypeptide does not contain an alanine at the front of the N-terminal of the mature wild type sequence.

One clone with the correct recombinant gene sequence was selected and the corresponding plasmid was integrated by homologous recombination into the *Bacillus subtilis* host cell genome (pectate lyase locus) and the gene construct was expressed under the control of a triple promoter system as described in WO 99/43835. The gene coding for chloramphenicol acetyltransferase was used as a marker (as described in Diderichsen et al., 1993, *Plasmid* 30:312-315).

Chloramphenicol resistant transformants were analyzed by PCR to verify the correct size of the amplified fragment. A recombinant *B. subtilis* clone containing the integrated expression construct was selected and it was cultivated on a rotary shaking table in 500 mL baffled Erlenmeyer flasks each containing 100 ml yeast extract-based media. The clone was cultivated for 5 days at 30° C. The enzyme containing supernatants were harvested and the enzyme purified as described in Example 2.

Example 2: Phospholipase C Purification

Purification of the Mature Peptide of SEQ ID NO: 3:
The cell-free culture broth was buffer-exchanged to 50 mM MES pH 6.5 using a packed bed of Sephadex® G-25 resin. The collected fractions were loaded onto a Source 15S cation-exchanger and eluted using a gradient of 0-100% 50 mM MES+0.5 M NaCl pH 6.5 in 10 CV's. Fractions were analyzed by SDS-PAGE (reducing conditions) and pooled based on purity.

Purification of the Mature Polypeptide of SEQ ID NO: 20:
Initially, an impurity capture step was performed using a packed bed of a decylamine agarose (Acetyleret Decylaminagarose, Cat. no. CS76, UpFront Cromatography A/S, Lersø Parkalle 42, 2100 Copenhagen Ø, Denmark). Binding buffer: 25 mM HEPES pH 7.5. Elution buffer: Binding buffer+0.01% (w/v) Triton X-100. The flow-through and wash fractions were pooled and buffer-exchanged to 50 mM MES pH 6.0 by loading onto a packed bed of Sephadex® G-25 resin. The collected fractions were loaded onto a Source 15Q anion-exchanger and eluted using a gradient of 0-100% 50 mM MES+0.5 M NaCl pH 6.0 in 10 CV's. Fractions were analyzed by SDS-PAGE (reducing conditions) and pooled based on purity. The pooled fractions were concentrated by use of centrifugal filter devices w/10 kDa MWCO and loaded onto a HiLoad™ 26/60 Superdex 200 pg gel filtration column equilibrated using 20 mM MES+125 mM NaCl pH 6.0. Fractions were analyzed by SDS-PAGE (reducing conditions) and pooled based on purity.

Example 3: Molecular Weight and N-Terminal Sequences of PLC

Determination of Molecular Weight:
The intact molecular weight analyses were performed using a Bruker microTOF focus electrospray mass spectrometer (Bruker Daltonik GmbH, Bremen, DE). The samples were diluted to 1 mg/ml in MQ water. The diluted samples were online washed on a MassPREP OnLine Desalting column (2.1×10 mm Part no. 186002785 Waters) and introduced to the electrospray source with a flow of 200 ul/h by an Agilent LC system. Data analysis is performed with DataAnalysis version 3.4 (Bruker Daltonik GmbH, Bremen, DE). The molecular weight of the samples was calculated by deconvolution of the raw data in the range 10.000 to 40.000 Da.

The molecular weight of the PI-specific phospholipase of SEQ ID NO: 3 was 32.7 kDa.

The molecular weight of the PC, PE-specific phospholipase of SEQ ID NO: 20 was 27.6 kDa.

N-Terminal Sequencing Procedure:
N-terminal sequencing analyses were performed using an Applied Biosystems Procise® protein sequencing system. The samples were purified on a Novex® precast 4-20% SDS polyacrylamide gel (Life Technologies). The gel was run according to manufacturer's instructions and blotted to a ProBlott® PVDF membrane (Applied Biosystems). For N-terminal amino acid sequencing the main protein band was cut out and placed in the blotting cartridge of the Procise® protein sequencing system. The N-terminal sequencing was carried out using the method run file for PVDF membrane samples (Pulsed liquid PVDF) according to manufacturer's instructions. The N-terminal amino acid sequence can be deduced from the 7 chromatograms corresponding to amino acid residues 1 to 7 by comparing the retention time of the peaks in the chromatograms to the retention times of the PTH-amino-acids in the standard chromatogram.

The N-terminal sequence of the mature polypeptide (SEQ ID NO: 3) was confirmed to be AQESPAF.

The N-terminal sequence of the mature polypeptide (SEQ ID NO: 6) was confirmed to be AQEAVGF.

The N-terminal sequence of the mature polypeptide (SEQ ID NO: 9) was confirmed to be AQEAVGF.

The N-terminal sequence of the mature polypeptide (SEQ ID NO: 20) was confirmed to be AWSADAP.

Example 4: Thermostability of the Phospholipase C

The thermostability of phospholipases C was determined by Differential Scanning calorimetry (DSC) using a VP-Capillary Differential Scanning calorimeter (MicroCal Inc., Piscataway, NJ, USA). The thermal denaturation temperature, Td (° C.), was taken as the top of denaturation peak (major endothermic peak) in thermograms (Cp vs. T) obtained after heating enzyme solutions (approx. 1 mg/ml) in buffer (50 mM Na-acetate pH 5.5±2 mM $CaCl_2$, or 50 mM Hepes pH 7±2 mM $CaCl_2$) at a constant programmed heating rate of 200 K/hr.

Sample- and reference-solutions (approx. 0.2 ml) were loaded into the calorimeter (reference: buffer without enzyme) from storage conditions at 10° C. and thermally pre-equilibrated for 20 minutes at 20° C. prior to DSC scan from 20° C. to 100° C. Denaturation temperatures were determined at an accuracy of approximately +/−1° C.

TABLE 2

| | Denaturation temperatures | | | |
|---|---|---|---|---|
| | Tm ° C. pH 5.5 | | Tm ° C. pH 7.0 | |
| Sequence ID | −CaCl2 | +CaCl2 | −CaCl2 | +CaCl2 |
| SEQ ID NO: 3 | 68 | 71 | 62.3 | |
| SEQ ID NO: 20 | | | 84 | 83 |

Example 5: Phospholipase C Specificity Towards PC, PE, PI, PA of Purified PLC's

The substrate specificity of the phospholipase C enzymes of the present invention and Purifine were determined using $^{31}$P-NMR. This assay follows the conversion of individual phospholipids shown in FIG. 1 in an oil environment and reveals the substrate specificity and preference of the phospholipase, and provides an indication of the pH optimum of the enzymes.

Substrate

Crude soy bean oils with the following content of the specific phospholipids measured by P-NMR were used.

PA: 80-140 ppm Phosphorus (P)
PE: 140-200 ppm P
PI: 70-110 ppm P
PC: 130-200 ppm P Other crude oils may also be applied in this assay, e.g., from rapeseed, sunflower, corn, cottonseed, groundnut, rice bran. The primary criterion is that the oil contains minimum 30 ppm of each of the specific phospholipids (to be significantly above the NMR quantification limit). Ensure mixing before the crude oil is pipetted (it precipitates over time).

Buffers and Enzyme 0.2 M Cs-EDTA pH 7.5 solution: EDTA (5.85 g) is dispersed in MQ-water (50 mL). The pH is adjusted to 7.5 using 50% w/w CsOH (approx. 30 mL), which will dissolve the EDTA completely. MQ-water is added to a total volume of 100 mL to give a concentration of 0.2 M.

Internal standard: 2 mg/mL solution triphenyl phosphate (TPP) in MeOH.

pH Buffers:

100 mM Na-citrate pH 4.0
100 mM Na-citrate pH 5.5
100 mM Na-citrate pH 7.0

Enzyme: Dilute to concentrations of 0.9, 0.27, and 0.09 mg Enzyme Protein (EP)/mL in the three buffers and keep cold to be used the same day.

Assay 250 micro-L crude oil was weighed into a 2 mL Eppendorf and 25 micro-L enzyme diluted in the desired pH buffer was added. This results in 10, 30, and 100 mg EP/kg oil. The mixture was incubated in a thermoshaker at 50° C. for 2 h.

Then 0.500 mL phosphate standard solution, 0.5 mL chloroform-d (CDCl3) and 0.5 mL Cs-EDTA buffer was added. Phase separation was obtained after 30 seconds shaking followed by centrifugation (tabletop centrifuge, 3 min, 13,400 rpm). The lower phase was transferred to a NMR-tube. $^{31}$P NMR with 128 scans, 5 sec delay time was run. All signals were integrated. Assignments (approx. ppm at 25° C.): 1.7 (PA), −0.1 (PE), −0.5 (PI), −0.8 (PC). The position of the signals can change significantly according to exact pH value, temperature, sample concentration, etc. The concentration of each species is calculated as "ppm P", i.e., mg elemental Phosphorus per kg oil sample. Hence, ppm P=I/I(IS)*n(IS)*M(P)/m(oil). % Remaining phospholipid is calculated as the ratio of the phospholipid concentration in the enzyme treated sample to the same concentration in a blank sample.

Results

The results are summarized in Tables 3 to 10 below.

TABLE 3

Specificity of phospholipase of SEQ ID NO: 3

| | 10 mg EP/kg Oil % Remaining phospholipid | | | 100 mg EP/kg oil % Remaining phospholipid | | |
|---|---|---|---|---|---|---|
| | pH 4.0 | pH 5.5 | pH 7.0 | pH 4.0 | pH 5.5 | pH 7.0 |
| PA | 106 | 97 | 110 | 106 | 103 | 106 |
| PE | 103 | 94 | 97 | 97 | 97 | 88 |
| PI | 88 | 44 | 20 | 52 | 12 | 12 |
| PC | 105 | 100 | 113 | 97 | 97 | 100 |

TABLE 4

Specificity of phospholipase of SEQ ID NO: 20.

| | 10 mg EP/kg Oil % Remaining phospholipid | | | 100 mg EP/kg oil % Remaining phospholipid | | |
|---|---|---|---|---|---|---|
| | pH 4.0 | pH 5.5 | pH 7.0 | pH 4.0 | pH 5.5 | pH 7.0 |
| PA | 100 | 103 | 97 | 106 | 100 | 109 |
| PE | 108 | 81 | 72 | 94 | 33 | 19 |
| PI | 100 | 96 | 100 | 88 | 100 | 96 |
| PC | 91 | 81 | 58 | 86 | 30 | 12 |

TABLE 5

Specificity of phospholipase of SEQ ID NO: 22 (amino acids 25-283).

| | 10 mg EP/kg Oil % Remaining phospholipid | | | 100 mg EP/kg oil % Remaining phospholipid | | |
|---|---|---|---|---|---|---|
| | pH 4.0 | pH 5.5 | pH 7.0 | pH 4.0 | pH 5.5 | pH 7.0 |
| PA | 105 | 95 | 103 | n.d. | n.d. | 61 |
| PE | 103 | 90 | 23 | n.d. | n.d. | 0 |
| PI | 96 | 99 | 96 | n.d. | n.d. | 90 |
| PC | 98 | 61 | 6 | n.d. | n.d. | 0 |

TABLE 6

Specificity of phospholipase of SEQ ID NO: 27.

| | 10 mg EP/kg Oil % Remaining phospholipid | | | 100 mg EP/kg oil % Remaining phospholipid | | |
|---|---|---|---|---|---|---|
| | pH 4.0 | pH 5.5 | pH 7.0 | pH 4.0 | pH 5.5 | pH 7.0 |
| PA | 102 | 98 | 104 | n.d. | n.d. | n.d. |
| PE | 100 | 62 | 14 | n.d. | n.d. | n.d. |
| PI | 97 | 99 | 95 | n.d. | n.d. | n.d. |
| PC | 88 | 38 | 0 | n.d. | n.d. | n.d. |

TABLE 7

Specificity of phospholipase of SEQ ID NO: 30.

|    | 10 mg EP/kg Oil % Remaining phospholipid | | | 100 mg EP/kg oil % Remaining phospholipid | | |
|----|--------|--------|--------|--------|--------|--------|
|    | pH 4.0 | pH 5.5 | pH 7.0 | pH 4.0 | pH 5.5 | pH 7.0 |
| PA | 107    | 106    | 105    | 102    | 86     | 71     |
| PE | 117    | 96     | 70     | 102    | 29     | 0      |
| PI | 94     | 91     | 91     | 87     | 86     | 82     |
| PC | 112    | 97     | 48     | 108    | 23     | 11     |

TABLE 8

Specificity of phospholipase of SEQ ID NO: 36.

|    | 10 mg EP/kg Oil % Remaining phospholipid | | | 100 mg EP/kg oil % Remaining phospholipid | | |
|----|--------|--------|--------|------|------|------|
|    | pH 4.0 | pH 5.5 | pH 7.0 | pH 4.0 | pH 5.5 | pH 7.0 |
| PA | 110    | 111    | 115    | n.d. | n.d. | n.d. |
| PE | 109    | 113    | 109    | n.d. | n.d. | n.d. |
| PI | 88     | 0      | 0      | n.d. | n.d. | n.d. |
| PC | 112    | 109    | 102    | n.d. | n.d. | n.d. |

TABLE 9

Specificity of phospholipase of SEQ ID NO: 38 (amino acids 36-280).

|    | 10 mg EP/kg Oil % Remaining phospholipid | | | 100 mg EP/kg oil % Remaining phospholipid | | |
|----|--------|--------|--------|--------|--------|--------|
|    | pH 4.0 | pH 5.5 | pH 7.0 | pH 4.0 | pH 5.5 | pH 7.0 |
| PA | 87     | 65     | 74     | 87     | 17     | 26     |
| PE | 109    | 0      | 7      | 70     | 0      | 0      |
| PI | 104    | 83     | 104    | 87     | 83     | 100    |
| PC | 98     | 78     | 4      | 82     | 0      | 0      |

TABLE 10

For an activity comparison, the performance of Purifine is shown below. Specificity of Purifine.

|    | 10 mg EP/kg Oil % Remaining phospholipid | | | 100 mg EP/kg oil % Remaining phospholipid | | |
|----|--------|--------|--------|--------|--------|--------|
|    | pH 4.0 | pH 5.5 | pH 7.0 | pH 4.0 | pH 5.5 | pH 7.0 |
| PA | 106    | 101    | 112    | 107    | 107    | 89     |
| PE | 106    | 114    | 18     | 107    | 38     | 0      |
| PI | 98     | 106    | 102    | 91     | 106    | 94     |
| PC | 105    | 98     | 0      | 114    | 20     | 0      |

Purifine concentration is estimated to 15 mg/mL.

Example 6: Phospholipase C Specificity Towards PC, PE, PI, PA of Crude Enzyme Supernatants In addition to the results on purified enzyme samples in Example 5 the phospholipase activity of several PLC homologues were tested using crude undiluted PLC supernatant in crude soy oil in a 1:10 (v/v) ratio. The enzyme concentrations were unknown and there was no pH control, otherwise the protocol of Example 5 was followed.

TABLE 11

Phospholipid hydrolysis with crude undiluted PLC containing supernatant.

|  | % Remaining phospholipid | | | |
|---|---|---|---|---|
|  | PA | PE | PI | PC |
| SEQ ID NO: 15 | 102 | 99  | 14  | 105 |
| SEQ ID NO: 12 | 124 | 109 | 54  | 109 |
| SEQ ID NO: 9  | 113 | 99  | 27  | 111 |
| SEQ ID NO: 6  | 114 | 109 | 49  | 107 |
| SEQ ID NO: 25 | 101 | 10  | 87  | 0   |
| SEQ ID NO: 27 | 96  | 8   | 100 | 3   |
| SEQ ID NO: 38 (amino acids 25-280) | 96 | 15 | 105 | 29 |
| SEQ ID NO: 36 | 88  | 100 | 17  | 92  |

Example 7: Degumming Assay

Performance of the phospholipase C enzymes of the present invention and Purifine as well as combinations of PI-specific and PC, PE specific phospholipase C enzymes were tested in a degumming assay that mimics industrial scale degumming. The assay measured the following parameters in the oil phase after the degumming:

a) Diglyceride content by High-performance liquid chromatography (HPLC) coupled to Evaporative Light Scattering Detector (ELSD), or Charged Aerosol Detector (Corona Veo).

b) Quantification of the individual phospholipids species: Phosphatidylcholine (PC); Phosphatidylinositol (PI); Phosphatidylethanolamine (PE); Phosphatidic acid (PA); by Liquid Chromatography quadrupole mass spectrometer time of flight (LC/TOF/MS)

c) Total phosphorus reduction by inductively coupled plasma optical emission spectrometry (ICP-OES).

The phospholipid composition in the crude soybean oil 2 or oil 3, used in the experiments, is indicated in Table 12. The composition was measured by LC/MS as phosphorus originating from individual phospholipid species.

TABLE 12

Phospholipid composition of crude oil (mg/kg phosphorus).

|       | Crude oil 2 | Crude oil 3 | Crude oil 4- | Crude oil 5 |
|-------|-------------|-------------|--------------|-------------|
| PA    | 295         | 85          | <20          | 110         |
| PE    | 125         | 187         | 312          | 222         |
| PI    | 84          | 182         | 85           | 64          |
| PC    | 229         | 410         | 557          | 187         |
| Total | 732         | 864         | 974          | 583         |

Degumming Assay

Crude soybean oil (75 g) was initially acid/base pretreated (or not) to facilitate conversion of insoluble phospholipids salt into more hydratable forms and ensure an environment suitable for the enzyme. Acid/base pretreatment was done by acid addition of Ortho Phosphoric acid (85% solution) applied in amounts equal to 0.05% (100% pure Ortho Phosphoric acid) based on oil amount and mixing in ultrasonic bath (BRANSON 3510) for 5 min and incubation in rotator for 15 min followed by base neutralization with 4 M NaOH applied in equivalents (from 0.5 to 1.5) to pure Ortho Phosphoric acid in ultrasonic bath for 5 min. The enzyme reaction was conducted in low aqueous system (3% water total based on oil amount) in 100 ml centrifuge tubes, cylindrical, conical bottom. Samples were ultrasonic treated for 5 min, followed by incubation in a heated cabinet at selected temperature (from 50 to 60° C.) with stirring at 20 rpm for a selected incubation time (from 1 to 5 hours). To separate the mixture into an oil phase and a heavy water/gum phase the samples were centrifuged at 700 g at 85° C. for 15 min (Koehler Instruments, K600×2 oil centrifuge).

a) Diglyceride Measurement

The HPLC-ELSD or HPLC-Corona Veo method (using DIONEX equipment and Lichrocart Si-60, 5 µm, Lichrosphere 250-4 mm, MERCK column) was based on the principle of the AOCS Official Method Cd 11d-96 and quantifies the diglyceride content down to 0.1 wt %.

b) Quantitative Analysis of Phospholipids by LCMS/MS

Liquid Chromatography coupled to triple quadrupole mass spectrometer (LC/MS/MS) or coupled to quadrupole mass spectrometer time of flight (LC/TOF/MS) was used to quantify the individual phospholipids species: phosphatidylcholine (PC); Phosphatidylinositol (PI); Phosphatidylethanolamine (PE) and Phosphatidic acid (phosphatidate) (PA). The sensitivity of the assay goes down to less than 1 mg Phosphorus/kg oil for PC, PE and PI (ppm) and less than 10 mg Phosphorus/kg for PA. The oil sample was dissolved in chloroform. The extract was then analysed on LC-TOF-MS (or on LC-MS/MS if lower detection limits are needed) using the following settings:

LC-Settings
Eluent A: 50% Acetonitril, 50% Water, 0.15% formic acid
Eluent B: 100% Isopropionic acid, 0.15% formic acid
Run time: 26.9 min
Flow: 0.50 mL/min
Column temperature: 50° C.
Autosampler temp: 15-25° C.
Injection volume: 1 µL
Column type Material: Charged Surface Hybrid, length: 50 mm, size: 1.7 µm, ID: 2.1 mm
MS-Settings

| MS-settings | |
|---|---|
| TOF/MS | MS/MS (Xevo) |
| Capillary: 3.50 kV | Capillary: +3.50/−2.0 kV |
| ☐☐Cone: 28 | Cone: Component specific |
| ☐☐Extractor: 2 V | ☐☐Extractor: 2.5 V |
| ☐☐RF-lens: 0.5 V | ☐☐RF-lens: |
| ☐☐Source temp: 125° C. | ☐☐Source temp: 150° C. |
| ☐☐Desolvation temp: 500° C. | ☐☐Desolvation temp: 500° C. |
| ☐☐Cone gas flow: 30 L/hour | ☐☐Cone gas flow: 30 L/hour |
| ☐☐Desolvation gas flow: 850 L/hour | ☐☐Desolvation gas flow: 850 L/hour |

The data was processed using MassLynx version 4.1 Software. In the below examples the method is just termed LCMS.

c) Phosphorus/Phospholipid Measurement

The ICP-OES quantifies the phosphorus (P) content and other metals such as Ca, Mg, Zn down to 4 ppm with an accuracy of approximately ±1 ppm P.

Examples 8 to 12 below describes results obtained using the degumming assay of this example.

Example 8: Enzyme Robustness to Different Acidity of the Pretreatments of the Oil The PI-specific phospholipase C of SEQ ID NO: 3 was applied in the degumming assay testing different acid/base pretreatments of the crude oil 3. The diglyceride content after enzymatic degumming at 50° C. and 60° C. for 1 and 3 hours, were measured. The results are shown in in Table 13.

TABLE 13

Increase of diglyceride after enzyme treatment of acid/base pretreated soybean oil measured by HPLC-ELSD.

| | Acid/base pretreatment of oil | | | |
|---|---|---|---|---|
| | 50 C. | | 60 C. | |
| | Enz. Reaction time (hours) | | | |
| | 1 | 3 | 1 | 3 |
| 0.05% PA/0.5 eqv NaOH | 0.19 | 0.37 | 0.37 | 0.37 |
| 0.05% PA/1.0 eqv NaOH | 0.06 | n.d. | 0.38 | 0.41 |
| 0.05% PA/1.5 eqv NaOH | 0.29 | 0.42 | 0.37 | 0.42 |
| no acid/base | 0.30 | 0.32 | 0.49 | 0.43 |

In the degumming assay the PI-specific phospholipase C of SEQ ID NO: 3 converts PI-phospholipids into diglycerides in a few hours. Full conversion is achieved after 3 hours based on the assumption that the 182 ppm P originating from PI (measured by LCMS) is equal to 0.50% PI-phospholipid (Mw PI~857 g/mol, Mw P~31 g/mol) equal to 0.40% DG increase (80% of phospholipid molecule). The enzyme showed good performance in water degumming (no acid/base) as well as acid assisted degumming followed by base neutralization with varying concentrations of NaOH. This demonstrated robustness towards varying pH conditions in the degumming process.

Example 9: Effect of Enzyme Dosage

The PI-specific phospholipase C of SEQ ID NO: 3 was applied in the degumming assay at various enzyme dosages in the crude oil 3. The diglyceride content after enzymatic degumming at 60° C. for 1, 2, 3 and 5 hours, were measured (oil pretreated with 0.05% phosphoric acid/1.5 eqv. NaOH). The results are shown in table 14.

TABLE 14

Increase of diglyceride after enzyme treatment of acid/base pretreated soybean oil measured by HPLC-ELSD.

| DG increase after x hours enz. Reaction/ Enzyme dosing mg EP/kg oil | 1 | 2 | 3 | 5 |
|---|---|---|---|---|
| 1 | 0.19 | 0.26 | 0.31 | 0.38 |
| 2 | 0.32 | 0.38 | 0.32 | 0.43 |
| 4 | 0.31 | 0.38 | 0.33 | 0.51 |
| 6 | 0.38 | 0.40 | 0.44 | 0.52 |
| 20 | 0.48 | 0.59 | 0.54 | 0.52 |

In the degumming assay the PI-specific phospholipase C of SEQ ID NO: 3 converted PI-phospholipids into diglycerides in 1-5 hours at enzyme dosage from 1 to 20 mg EP/kg oil. Data demonstrates a dose-response effect with faster phospholipid conversion to diglyceride at higher enzyme dosing. PI content after degumming was reduced to less than 1 mg/kg oil in all cases (measured by LCMS) and shows that the enzyme attacks the PI species.

Example 10: Combination of PI-Specific PLC and PC, PE-Specific PLC at 50° C.

The PI-specific phospholipase C of SEQ ID NO: 3 was applied in the degumming assay at 50° C. in combination with the PC, PE-specific phospholipase Purifine PLC and the PLC of SEQ ID NO: 22 applying crude oil 3 pretreated with 0.05% phosphoric acid/1.5 eqv. NaOH. The diglyceride content after enzymatic degumming for 1, 2, 3 and 5 hours, were measured as well as the metal content. The results are shown in Tables 15A+B.

TABLE 15A

Increase of diglyceride after enzyme treatment of 0.05% phosphoric acid/1.5 eqv. NaOH pretreated soybean oil measured by HPLC-ELSD.

| ENZ | Enz. Dosage (mg EP/kg oil) | Enz. Reaction time (hours) | | | |
|---|---|---|---|---|---|
| | | 1 | 2 | 3 | 5 |
| PurifinePLC | 4 | 0.23 | 0.30 | 0.36 | 0.43 |
| SEQ ID NO: 3 | 4 | 0.09 | 0.06 | 0.08 | 0.07 |
| SEQ ID NO: 22 | 4 | 0.04 | 0.12 | 0.06 | 0.20 |
| SEQ ID NO: 3 + SEQ ID NO: 22 | 4 + 4 | 0.19 | 0.27 | 0.32 | 0.47 |
| SEQ ID NO: 3 + + Purifine | 4 + 4 | 0.45 | 0.59 | 0.69 | 0.68 |
| SEQ ID NO: 3 + SEQ ID NO: 22 | 4 + 10 | 0.29 | 0.44 | 0.61 | 0.80 |

TABLE 15B

Ca, Mg, P composition (mg/kg oil) measured by ICP-OES after 5 hours enzyme treatment.

| | Enzyme Dosage (mg EP/kg oil) | Ca | Mg | P |
|---|---|---|---|---|
| Crude oil 3 | | 71 | 74 | 998 |
| Purifine | 4 | 7 | 5 | 5.3 |
| SEQ ID NO: 3 | 4 | 5 | 5 | 5.5 |
| SEQ ID NO: 22 | 4 | 6 | 5 | 3.8 |
| SEQ ID NO: 3 + SEQ ID NO: 22 | 4 + 4 | 6 | 5 | 7 |
| SEQ ID NO: 3 + SEQ ID NO: 22 | 4 + 10 | 5 | 5 | 4.3 |
| SEQ ID NO: 3 + Purifine | 4 + 4 | 6 | 5 | 4.7 |

Degumming with the PI-specific phospholipase C of SEQ ID NO: 3 combined with PC, PE specific PLC (purifine PLC or SEQ ID NO: 22) resulted in significant diglyceride formation at 50° C. The blends resulted in a combined effect compared to the individual solutions seen by a greater DG increase. Phosphorus content in degummed oil was reduced to a desirable end level below 5 mg/kg and is equal to 'full' conversion.

Example 11 PI-Specific PLC in Combination with PC, PE Specific PLC at 60° C.

The PI-specific phospholipase C of SEQ ID NO: 3 was applied in the degumming assay at 60° C. alone or in combination with the PC, PE-specific PLC of SEQ ID NO: 22 in crude oil 3 pretreated with 0.05% phosphoric acid/1.5 eqv. NaOH. The diglyceride content after enzymatic degumming for 1, 2, 3 and 5 hours, were measured. The results are shown in table 16.

TABLE 16

Increase of diglyceride after enzyme treatment of 0.05% phosphoric acid/1.5 eqv. NaOH pretreated crude soybean oil measured by HPLC-ELSD.

| ENZ | Enz. Dosage (mg EP/kg oil) | Enz. Reaction time (hours) | | | |
|---|---|---|---|---|---|
| | | 1 | 2 | 3 | 5 |
| SEQ ID NO: 3 | 4 | 0.22 | 0.29 | 0.29 | 0.35 |
| SEQ ID NO: 22 | 4 | 0.20 | 0.40 | 0.47 | 0.82 |
| SEQ ID NO: 3 + SEQ ID NO: 22 | 4 + 4 | 0.48 | 0.84 | 0.96 | 1.18 |
| SEQ ID NO: 3 + SEQ ID NO: 22 | 4 + 10 | 0.66 | 0.93 | 1.09 | 1.21 |

Degumming with the PI-specific phospholipase C of SEQ ID NO: 3 combined with the PC, PE-specific PLC of SEQ ID NO: 22 at 60° C. resulted in a combined effect compared to the effect of the individual enzymes, and converted major parts of phospholipids (up to 87% at conditions tested (60° C., 5 hours). Calculation is based on the assumption that 864 ppm P total measured by LC/MS is equal to 2.15 wt % phospholipid (Average Mw~772 g/mol) equal to max 1.72% DG increase obtainable (80% of phospholipid molecule). LCMS results shows less than 4 ppm P from PI, PC, PE in degummed oil sample and confirms that the blend attack PC; PE; PI phospholipid species.

Example 12: PI-Specific PLC in Combination with PC, PE Specific PLC at 60° C.

The PI-specific phospholipase C of SEQ ID NO: 3 was applied in the degumming assay at 60° C. alone and in combination with Purifine PLC or SEQ ID NO: 20 in crude oil 2 pretreated with 0.05% phosphoric acid/1.5 eqv. NaOH. The diglyceride content after enzymatic degumming for 3 and 5 hours was measured. The results are shown in Table 17.

TABLE 17

Increase of diglyceride after enzyme treatment of 0.05% phosphoric acid/1.5 eqv. NaOH pretreated crude soybean oil measured by HPLC-ELSD.

| ENZ | Enz. Dosage (mg EP/kg oil) | Enz. Reaction time (hours) | |
|---|---|---|---|
| | | 3 h | 5 h |
| SEQ ID NO: 3 | 4 | 0.16 | 0.17 |
| PurifinePLC | 4 | 0.62 | 0.65 |
| SEQ ID NO: 20 | 4 | 0.15 | 0.27 |
| SEQ ID NO: 20 | 10 | 0.32 | 0.48 |
| SEQ ID NO: 3 + Purifine | 4 + 4 | 0.67 | 0.75 |
| SEQ ID NO: 3 + SEQ ID NO: 20 | 4 + 4 | 0.30 | 0.43 |
| SEQ ID NO: 3 + SEQ ID NO: 20 | 4 + 10 | 0.48 | 0.63 |

The phospholipid species PI, PE and PC which are the species hydrolyzed by the applied enzymes make up 60% of the total 732 ppm phospholipid in the used crude oil determined by LC/MS, equaling to max 0.86% DG increase upon full hydrolysis. Degumming with the PI-specific phospholipase C of SEQ ID NO: 3 combined with the PC, PE-specific PLC of SEQ ID NO: 20 or Purifine PLC results in a combined effect compared to the effect of the individual enzymes and converts up to 51% of the total phospholipids at 60° C., 5 hours. This corresponds to hydrolysis of majority of the PI, PE and PC in the crude oil sample. Calculations are based on phospholipid average MW 772 g/mol.

Example 13: Degumming Using PI-Specific PLC in Combination with PC, PE Specific PLC at 60° C.

The PC, PE-specific phospholipase C (SEQ ID NO: 22 (amino acids 25-283)), SEQ ID NO: 25 and SEQ ID NO:27 was applied in the degumming assay at 60° C. alone and in combination with PI-specific phospholipase C of SEQ ID NO: 3 in crude oil 5. The phospholipases were dosed as volume filtered fermentation broth (2 or 4 ml) per 50 g crude oil apart from Purifine dosed as 4 mg enzyme protein per kg oil. The diglyceride increase after enzymatic degumming for 2 and 5 hours are shown in table 18. The water degummed oil was post-treated with 0.09% phosphoric/0.5 eqv. NaOH before the phosphorous content was measured by ICP-method.

TABLE 18

Increase of diglyceride after enzyme treatment measured by HPLC-Corona Veo and phosphorous content measured by ICP after oil post-treatment with of 0.09% phosphoric acid/0.5 eqv. NaOH.

| ENZ | Enzyme dosing per 50 g oil | Speci-ficity | DG increase (wt %) as function of reaction time (hours) | | Total P by ICP (mg/kg oil) |
|---|---|---|---|---|---|
| | | | 2 | 5 | 5 h |
| Purifine | 4 mg EP/ kg oil | PC, PE | 0.19 | 0.13 | 14 |
| SEQ ID 22 (a.a. 25-283) | 2 ml | PC, PE | 0.37 | 0.27 | 13 |
| Seq ID NO: 25 | 2 ml | PC, PE | 0.11 | 0.10 | 16 |
| SEQ ID 27 | 2 ml | PC, PE | 0.14 | 0.21 | 22 |
| SEQ ID NO: 2 (a.a. 25-283) & 3 and 22 | 2 + 4 ml | PI; PC; PE | 0.18 | 0.60 | 21 |
| SEQ ID NO: 2 (a.a. 25-283) & 3 and 24&25 | 2 + 2 ml | PI; PC; PE | 0.16 | 0.60 | 18 |
| SEQ ID NO: 2 (a.a. 25-283) & 3 and 27 | 2 + 2 ml | PI; PC; PE | 0.22 | 0.66 | 30 |

The phospholipid species PI, PE and PC which are the species hydrolyzed by the applied enzymes make up 81% of the total 583 ppm phospholipid in the used crude oil determined by LC/MS, equaling to max 0.95% DG increase upon full hydrolysis. Calculations are based on conversion factor from phosphorous to phospholipids of 0.0025 and that diglycerides constitute 80% of the phospholipid molecule. Degumming with the PI-specific phospholipase C of SEQ ID NO: 3 combined with the PC, PE-specific PLC of SEQ ID NO: 22 (amino adds 25-283), SEQ ID NO: 25 or SEQ ID NO: 27 results in a combined effect compared to the effect of the individual enzymes and converts up to 70% of the total accessible phospholipids at 60° C., 5 hours.

Example 14: Degumming Using PI-Specific PLC in Combination with PC, PE Specific PLC at 60° C.

The PC, PE-specific phospholipase C of SEQ ID NO: 22 (amino adds 25-283) was applied in the degumming assay at 60° C. alone and in combination with PI-specific phospholipase C (SEQ ID NO: 9 and SEQ ID NO: 15) using crude oil 5. The PI-specific phospholipase Cs were dosed as volume filtered fermentation broth (2 ml) per 50 g crude oil while the PC; PE-specific phospholipase Cs were dosed as purified mg enzyme protein per kg oil (4 mg EP/kg oil). The diglyceride increase after enzymatic degumming for 2 and 5 hours are shown in table 19. The water degummed oil was post-treated with 0.09% phosphoric/0.5 eqv. NaOH before the phosphorous content was measured by ICP-method.

TABLE 19

Increase of diglyceride after enzyme treatment measured by HPLC-Corona Veo and phosphorous content measured by ICP after oil post-treatment with of 0.09% phosphoric acid/0.5 eqv. NaOH.

| Enzyme | Dosing per 50 g oil | Speci-ficity | DG increase (wt %) as function of reaction time (hours) | | Total P by ICP (mg/kg oil) |
|---|---|---|---|---|---|
| | | | 2 | 5 | 5 h |
| Blank | | | 0.23 | 0.12 | 16 |
| Purifine | 4 mg EP | PC, PE | 0.56 | 0.48 | 16 |
| SEQ ID NO: 22 (a.a. 25-283) | 4 mg EP | PC; PE | 0.54 | 0.43 | 16 |
| SEQ ID NO: 9 | 2 ml | PI | 0.39 | 0.22 | 13 |
| SEQ ID NO: 15 | 2 ml | PI | 0.40 | 0.27 | 17 |
| SEQ ID NO: 22 (a.a. 25-283) + 15 | 4 mg EP + 2 ml | PC; PE; PI | 0.66 | 0.55 | 13 |
| SEQ ID NO: 22 (a.a. 25-283) + 9 | 4 mg EP + 2 ml | PC; PE; PI | 0.47 | 0.51 | 12 |

The phospholipid species PI, PE and PC which are the species hydrolyzed by the applied enzymes make up 81% of the total 583 ppm phospholipid in the used crude oil determined by LC/MS, equaling to max 0.95% DG increase upon full hydrolysis. Degumming with the PC; PE-specific phospholipase C of SEQ ID NO: 22 (amino adds 25-283) combined with the PI-specific PLC of SEQ ID NO: 9 and 15 results in a combined effect compared to the effect of the individual enzymes and converts up to 70% of the total accessible phospholipids at 60° C., 2 hours.

Example 15: Water Degumming Using PI-Specific PLC in Combination with PC, PE Specific PLC at 60° C.

The PI-specific phospholipase C of SEQ ID NO: 3 was applied in the degumming assay at 60° C. alone and in combination with PC, PE-specific phospholipase C (SEQ ID NO: 22 (amino adds 25-283), SEQ ID NO: 25 and SEQ ID NO: 27 (amino adds 25-283)) in crude oil 4. Purifine and SEQ ID NO: 22 (amino adds 25-283) were dosed as mg purified enzyme protein per kg oil while the rest were dosed as volume filtered fermentation broth per 40 g crude oil. The diglyceride increase after enzymatic water degumming (no acid/base oil treatment) for 2 and 5 hours as well as and phosphorous content measured by ICP are shown in Table 20.

TABLE 20

Increase of diglyceride after enzyme treatment measured by HPLC-Corona Veo and phosphorous content measured by ICP.

| Enzyme | Enzyme Dosing | Speci-ficity | DG increase (wt %) as function of reaction time (hours) | | Total P by ICP (mg/kg oil) |
|---|---|---|---|---|---|
| | | | 2 | 5 | 5 hours |
| Purifine | 4 mg EP/ kg oil | PC; PE | 0.96 | 0.88 | 1.4 |

TABLE 20-continued

Increase of diglyceride after enzyme treatment measured by HPLC-Corona Veo and phosphorous content measured by ICP.

| Enzyme | Enzyme Dosing | Speci-ficity | DG increase (wt %) as function of reaction time (hours) 2 | 5 | Total P by ICP (mg/kg oil) 5 hours |
|---|---|---|---|---|---|
| SEQ ID NO: 22 (a.a. 25-283) | 4 mg EP/ kg oil | PC; PE | 0.82 | 0.89 | 1.6 |
| SEQ ID NO: 25 | 1.6 ml/ 40 g oil | PC; PE | 0.48 | 0.75 | 1.5 |
| SEQ ID NO: 27 (a.a. 25-283) | 1.6 ml/ 40 g oil | PC; PE | 0.52 | 0.88 | 0.7 |
| SEQ ID NO: 3 | 1.6 ml/ 40 g oil | PI | 0.25 | 0.27 | 0.8 |
| SEQ ID NO: 3 + 22 (a.a. 24-283) | 1.6 ml + 4 mg EP | PC; PE; PI | 1.00 | 1.18 | 1.3 |
| SEQ ID NO: 3 + 25 | 1.6 ml + 1.6 ml | PC; PE; PI | 0.91 | 1.16 | 1.3 |
| SEQ ID NO: 3 + 27 (a.a. 25-283) | 1.6 ml + 1.6 ml | PC; PE; PI | 0.93 | 1.24 | 1.3 |

Degumming with the PI-specific phospholipase C of SEQ ID NO: 3 combined with PC, PE specific PLC (SEQ ID NO: 22 (amino acids 25-283), SEQ ID NO: 25 and SEQ ID NO: 27 (amino adds 25-283)) resulted in significant diglyceride formation. The phospholipid species PI, PE and PC which are the species hydrolyzed by the applied enzymes make up 98% of the total 974 ppm phospholipid in the used crude oil determined by LC/MS, equaling to max 1.91% DG increase upon full hydrolysis. Calculations are based on conversion factor from phosphorous to phospholipids of 0.0025 and that diglycerides constitute 80% of the phospholipid molecule. Degumming with the PI-specific phospholipase C of SEQ ID NO: 3 combined with the PC, PE-specific PLC of SEQ ID NO: 27 results in a combined effect compared to the effect of the individual enzymes and converts up to 65% of the total accessible phospholipids at 60° C., 5 hours. Phosphorus content in degummed oil was reduced to below 5 mg/kg.

Example 16: Water Degumming Using PI-Specific PLC in Combination with PC, PE Specific PLC at 60° C.

The PC, PE-specific phospholipase C of SEQ ID NO: 22 (amino adds 25-283) was applied in the degumming assay at 60° C. alone and in combination with PI-specific phospholipase C (SEQ ID NO: 9 and SEQ ID NO: 15) using crude oil 4. The PI-specific phospholipase Cs were dosed as 2 ml filtered fermentation broth per 50 g crude oil while the PC; PE-specific phospholipase Cs were dosed as 4 mg enzyme protein per kg oil. The diglyceride increase after enzymatic water degumming (no acid/base oil treatment) for 2 and 5 hours as well as and phosphorous content measured by ICP are shown in Table 21.

TABLE 21

Increase of diglyceride after enzyme treatment measured by HPLC-Corona Veo and phosphorous content measured by ICP.

| Enzyme | Dosing | Speci-ficity | DG increase (wt %) as function of reaction time (hours) 2 | 5 | Total P by ICP (mg/kg oil) 5 hours |
|---|---|---|---|---|---|
| Blank | | | 0.05 | 0.04 | 5.3 |
| Purifine | 4 mg EP/ kg oil | PC; PE | 0.90 | 0.98 | 0.9 |
| SEQ ID NO: 22 (a.a. 24-283) | 4 mg EP/ kg oil | PC; PE | 0.89 | 0.93 | 1.0 |
| SEQ ID NO: 9 | 2 ml/ 50 g oil | PI | 0.27 | 0.33 | 1.2 |
| SEQ ID NO: 15 | 2 ml/ 50 g oil | PI | 0.30 | 0.35 | 2.1 |
| SEQ ID NO: 22 (a.a. 25-283) + 15 | 4 mg EP + 2 ml | PC; PE; PI | 1.18 | 1.28 | 1.3 |
| SEQ ID NO: 22 (a.a. 25-283) + 9 | 4 mg EP + 2 ml | PC; PE; PI | 1.15 | 1.32 | 1.5 |

Degumming with the PC, PE-specific phospholipase C of SEQ ID NO: 22 (amino adds 25-283) combined with PI-specific phospholipase C of SEQ ID NOS: 9 and 15 resulted in significant diglyceride formation. The phospholipid species PI, PE and PC which are the species hydrolyzed by the applied enzymes make up 98% of the total 974 ppm phospholipid in the used crude oil determined by LC/MS, equaling to max 1.91% DG increase upon full hydrolysis. Degumming with the with the PC, PE-specific PLC of SEQ ID NO: 22 (amino adds 25-283) combined with PI-specific phospholipase C of SEQ ID NO: 9 and 15 combined results in a combined effect compared to the effect of the individual enzymes and converts up to 69% of the total accessible phospholipids at 60° C., 5 hours. Phosphorus content in degummed oil was reduced to below 5 mg/kg.

Example 17: Water Degumming Using PI-Specific PLC in Combination with PC, PE Specific PLC at 60° C.

The PC, PE-specific phospholipase C of SEQ ID NO: 22 (amino acids. 25-283) was applied in the degumming assay at 60° C. alone and in combination with PI-specific phospholipase C (SEQ ID NO: 3 and SEQ ID NO: 6) using crude oil 4. The phospholipases were dosed as 4 ml filtered fermentation broth per 50 g crude oil. The diglyceride increase after enzymatic water degumming (no acid/base oil treatment) for 2 and 5 hours as well as the phosphorous content measured by ICP after 5 hours are shown in Table 22.

TABLE 22

Increase of diglyceride after enzyme treatment measured by HPLC-Corona Veo and phosphorous content measured by ICP.

| Enzyme | Dosing per 50 g oil | Speci-ficity | DG increase (wt %) as function of reaction time (hours) 2 | 5 | Total P by ICP (mg/kg oil) (5 h) |
|---|---|---|---|---|---|
| SEQ ID NO: 22 (a.a. 25-283) | 4 ml | PC, PE | 0.72 | 0.93 | 0.8 |
| SEQ ID NO: 23 + 22 (a.a. 25-283) | 4 + 4 ml | PC; PE; PI | 0.93 | 1.24 | 1.7 |

TABLE 22-continued

Increase of diglyceride after enzyme treatment measured by
HPLC-Corona Veo and phosphorous content measured by ICP.

| Enzyme | Dosing per 50 g oil | Specificity | DG increase (wt %) as function of reaction time (hours) 2 | 5 | Total P by ICP (mg/kg oil) (5 h) |
|---|---|---|---|---|---|
| SEQ ID NO: 6 + 22 (a.a. 25-283) | 4 + 4 ml | PC; PE; PI | 0.96 | 1.24 | 1 |

Degumming with the PC, PE-specific phospholipase C of SEQ ID NO: 22 (amino adds 25-283) combined with PI-specific phospholipase C of SEQ ID NOS: 3 and 6 resulted in combined effect compared to the effect of the individual enzymes and converts up to 65% of the total accessible PI; PC; PE phospholipids at 60° C., 5 hours. Phosphorus content in degummed oil was reduced to a desirable end level below 5 mg/kg equal to 'full' P removal/reduction.

Example 18: Degumming Using PI-Specific PLC
(SEQ ID NO: 38 Amino Acids 25-280) in
Degumming Assay at 60° C.

The PC, PE-specific phospholipase C of SEQ ID NO: 38 (amino acids 25-280) was applied in the degumming assay at 60° C. using crude oil 5 (diff oil). The crude oil 5 was pre-treated with 0.09% phosphoric acid and 1.5 molar equivalents of NaOH prior to incubation with enzymes. The phospholipase was dosed as 30 mg enzyme protein per kg oil. The diglyceride increase after enzymatic degumming for 2, 4, 6 and 24 hours was measured by HPLC-Corona Veo as well as the phosphorous content measured by ICP after 24 hours are shown in Table 23.

TABLE 23

Increase of diglyceride after enzyme treatment measured by HPLC-Corona Veo and
phosphorous content measured by ICP.

| Enzyme | Enz dosing mg EP/kg oil | DG increase (wt %) as function of reaction time (hours) 2 | 4 | 6 | 24 | Total P by ICP as function of reaction time (hours) (mg/kg oil) 2 | 24 |
|---|---|---|---|---|---|---|---|
| Blank |  | 0.08 | 0.07 | 0.06 | 0.14 | 34 | 32 |
| SEQ ID NO: 38 (a.a. 25-280) | 30 | 0.43 | 0.43 | 0.41 | 0.60 | 40 | 39 |

The phospholipid species PC and PE which are the species hydrolyzed by the applied enzymes make up 70% of the total 583 ppm phospholipid in the used crude oil determined by LC/MS, equaling to max 0.82% DG increase upon full hydrolysis. Calculations are based on conversion factor from phosphorous to phospholipids of 0.0025 and that diglycerides constitute 80% of the phospholipid molecule. Degumming with the phospholipase C of SEQ ID NO: 38 (amino acids 25-280) converts up to 53% of the total accessible phospholipids at 60° C., 2 hours.

Example 19: SEQ ID NO: 22 (Amino Acids
39-283) and SEQ ID NO: 38 (Amino Acids
36-280) Tested in Degumming Assay at 60° C.
Citric Acid/Base Pretreatment The PC, PE-specific phospholipase C of SEQ ID NO: 22 (amino acids 39-283) and the PC, PE-specific phospholipase C of SEQ ID NO: 38 (amino acids 36-280) were applied in the degumming assay at 60° C. using crude oil 5 (diff oil). The crude oil 5 was pre-treated with 0.065% citric acid and 1.5 molar equivalents of NaOH prior to incubation with enzymes. The phospholipase was dosed as 4 ml filtered fermentation broth per 50 g crude oil. The diglyceride increase after enzymatic degumming for 2 and 5 hours as well as the phosphorous content measured by ICP after 2 hours are shown in Table 24.

TABLE 24

Increase of diglyceride after enzyme treatment measured by
HPLC-Corona Veo and phosphorous content measured by ICP.

| Enz/SEQ ID NO: | Enz dosing per 50 g oil | DG increase (wt %) as function of reaction time (hours) 2 | 5 | Total P by ICP (2 h WDG) 2 hours |
|---|---|---|---|---|
| Blank | 4 ml | 0.02 | 0.04 | 12 |
| SEQ ID NO: 38 (a.a. 36-280) | 4 ml | 0.50 | 0.63 | 12 |
| SEQ ID NO: 22 (a.a. 39-283) | 4 ml | 0.46 | 0.49 | 15 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method for reducing the content of phospholipids in an oil composition, the method comprising
   a) contacting an oil composition containing a quantity of phospholipids with a phosphatidylinositol phospholipase C and a phosphatidylcholine and phosphatidylethanolamine-specific phospholipase C polypeptide ("a PC and PE-specific phospholipase C") under conditions sufficient to hydrolyze the phospholipids to diglyceride and phosphate ester, wherein
      i) the phosphatidylinositol phospholipase C has at least 90% sequence identity to amino acid residues 26-322 of SEQ ID NO: 2 or amino acid residues 1-298 of SEQ ID NO: 3, and
      (ii) the PC and PE-specific phospholipase C has at least 90% sequence identity to amino acid residues 34-278 of SEQ ID NO: 19 or amino acid residues 1-246 of SEQ ID NO: 20; and
   b) separating the phosphate ester from the oil composition.

2. The method of claim 1, wherein the oil is an edible oil.

3. The method of claim 1, wherein the oil is selected from the group consisting of crude oil, water degummed oil, caustic refined oil and acid degummed oil.

4. The method of claim 1, wherein the oil comprises phosphatidylcholine (PC), phosphatidylethanolamine (PE) and phosphatidyl inositol (PI).

5. The method of claim 4, wherein the oil comprises at least 50 ppm phosphorus originating from phosphatidyl inositol (PI).

6. The method of claim 1, wherein
   (a) the phosphatidylinositol phospholipase C has at least 95% sequence identity to amino acid residues 26-322 of SEQ ID NO: 2 or amino acid residues 1-298 of SEQ ID NO: 3; and
   (b) the PC and PE-specific phospholipase C polypeptide has at least 95% sequence identity to amino acid residues 34-278 of SEQ ID NO: 19 or amino acid residues 1-246 of SEQ ID NO: 20.

7. The method of claim 1, wherein
   (a) the phosphatidylinositol phospholipase C has at least 98% sequence identity to amino acid residues 26-322 of SEQ ID NO: 2 or amino acid residues 1-298 of SEQ ID NO: 3; and
   (b) the PC and PE-specific phospholipase C polypeptide has at least 98% sequence identity to amino acid residues 34-278 of SEQ ID NO: 19 or amino acid residues 1-246 of SEQ ID NO: 20.

8. The method of claim 1, wherein
   (a) the phosphatidylinositol phospholipase C comprises amino acid residues 26-322 of SEQ ID NO: 2 or amino acid residues 1-298 of SEQ ID NO: 3; and
   (b) the PC and PE-specific phospholipase C polypeptide comprises amino acid residues 34-278 of SEQ ID NO: 19 or amino acid residues 1-246 of SEQ ID NO: 20.

9. The method of claim 1, wherein
   (a) the phosphatidylinositol phospholipase C is a fragment of amino acid residues 26-322 of SEQ ID NO: 2 or amino acid residues 1-298 of SEQ ID NO: 3; and
   (b) the PC and PE-specific phospholipase C polypeptide is a fragment of amino acid residues 34-278 of SEQ ID NO: 19 or amino acid residues 1-246 of SEQ ID NO: 20.

10. The method of claim 1, wherein the oil is contacted with 0.5-200 mg enzyme protein (EP)/Kg oil of the phosphatidylinositol phospholipase C and with 0.5-200 mg enzyme protein (EP)/Kg oil of the PC and PE-specific phospholipase C.

11. The method of claim 1, wherein the oil is contacted with 1-25 mg enzyme protein (EP)/Kg oil of the phosphatidylinositol phospholipase C and with 1-25 mg enzyme protein (EP)/Kg oil of the PC and PE-specific phospholipase C.

12. The method of claim 1, wherein the oil is contacted with 2-15 mg enzyme protein (EP)/Kg oil of the phosphatidylinositol phospholipase C and with 2-15 mg enzyme protein (EP)/Kg oil of the PC and PE-specific phospholipase C.

* * * * *